US010077426B2

(12) United States Patent
Mevorach et al.

(10) Patent No.: US 10,077,426 B2
(45) Date of Patent: Sep. 18, 2018

(54) THERAPEUTIC APOPTOTIC CELL PREPARATIONS, METHOD FOR PRODUCING SAME AND USES THEREOF

(71) Applicant: Enlivex Therapeutics Ltd., Jerusalem (IL)

(72) Inventors: Dror Mevorach, Jerusalem (IL); Inna Reiner, Jerusalem (IL)

(73) Assignee: Enlivex Therapeutics Ltd, Jerusalem (IL)

( * ) Notice: Subject to any disclaimer, the term of this patent is extended or adjusted under 35 U.S.C. 154(b) by 0 days.

(21) Appl. No.: 14/401,524

(22) PCT Filed: Dec. 5, 2013

(86) PCT No.: PCT/IL2013/051001
§ 371 (c)(1),
(2) Date: Nov. 16, 2014

(87) PCT Pub. No.: WO2014/087408
PCT Pub. Date: Jun. 12, 2014

(65) Prior Publication Data
US 2015/0275175 A1    Oct. 1, 2015

Related U.S. Application Data

(60) Provisional application No. 61/733,936, filed on Dec. 6, 2012, provisional application No. 61/778,497, filed on Mar. 13, 2013, provisional application No. 61/872,884, filed on Sep. 3, 2013.

(51) Int. Cl.
| | |
|---|---|
| *A61K 31/727* | (2006.01) |
| *C12N 5/00* | (2006.01) |
| *C12N 5/078* | (2010.01) |
| *A61K 35/17* | (2015.01) |
| *A61K 45/06* | (2006.01) |
| *A61K 31/194* | (2006.01) |
| *A61K 31/573* | (2006.01) |
| *A61K 31/7004* | (2006.01) |

(52) U.S. Cl.
CPC .......... *C12N 5/0634* (2013.01); *A61K 31/194* (2013.01); *A61K 31/573* (2013.01); *A61K 31/7004* (2013.01); *A61K 31/727* (2013.01); *A61K 35/17* (2013.01); *A61K 45/06* (2013.01)

(58) Field of Classification Search
CPC .. C12N 5/0634; C12N 5/0635; C12N 5/0636; C12N 5/0645; C12N 5/0646
See application file for complete search history.

(56) References Cited

U.S. PATENT DOCUMENTS

| 5,667,963 A | 9/1997 | Smith et al. |
| 6,489,311 B1 | 12/2002 | Kennedy |
| 6,524,865 B1 | 2/2003 | Martin |
| 6,607,722 B2 | 8/2003 | Edelson |
| 7,109,031 B2 | 9/2006 | Edelson |
| 7,544,355 B2 * | 6/2009 | Velardi ............... C12N 5/0646 424/93.1 |
| 7,988,951 B2 | 8/2011 | Edelson |
| 8,524,495 B2 | 9/2013 | Edelson |
| 2005/0163778 A1 | 7/2005 | Peritt et al. |
| 2005/0202098 A1 * | 9/2005 | Mevorach ............ A61K 35/15 424/533 |
| 2007/0098686 A1 | 5/2007 | Peritt et al. |
| 2010/0183586 A1 | 7/2010 | Hori et al. |
| 2011/0091433 A1 | 4/2011 | Abuljadayel |
| 2014/0072954 A1 | 3/2014 | Umeda et al. |

FOREIGN PATENT DOCUMENTS

| JP | 2002-179579 A | 6/2002 |
| JP | 2007-326824 A | 12/2007 |
| JP | 2009-178129 A | 8/2009 |
| JP | 2012-077006 A | 4/2012 |
| WO | WO 2001/070273 | 9/2001 |
| WO | WO 2001/089536 A2 | 11/2001 |
| WO | WO 2002/060376 | 8/2002 |
| WO | WO 2003/006691 | 1/2003 |
| WO | WO 2003/045979 A2 | 5/2003 |
| WO | WO 2004/035064 A1 | 4/2004 |
| WO | WO 2006/117786 | 9/2006 |
| WO | WO 2006/123993 A2 | 11/2006 |
| WO | WO 2010/070105 A1 | 6/2010 |

OTHER PUBLICATIONS

Albert; Death-defying immunity: do apoptotic cells influence antigen processing and presentation? Nat Rev Immunol 2004; 4 (3):223-231.
Amarilyo et al.; iC3b-opsonized apoptotic cells mediate a distinct anti-inflammatory response and transcriptional NF-kappaB-dependent blockade. Eur J Immunol., 2010;40:699-709.
Arai et al.; "Management of graft-versus-host disease", Blood Rev, 2000; 14 (4):190-204.
Bauer, Christian, et al. "Colitis Induced in Mice With Dextran Sulfate Sodium (Dss) Is Mediated by the NIrp3 Inflammasome." GUT 2010; 59.9, 1192-1199.
Bittencourt, M. et al. "Intravenous injection of apoptotic leukocytes enhances bone marrow engraftment across major histocompatibility barriers." Blood, 98.1, pp. 224-230, 2001.
Bolanos-Meade ; "Update on the management of acute graft-versus-host disease", Curr Opin Oncol, 2006; 18 (2): 120-125.
Bossard et al.; "Plasmacytoid dendritic cells and Th17 immune response contribution in gastrointestinal acute graft-versus-host disease", Leukemia., 2012;26:1471-4.

(Continued)

*Primary Examiner* — Ruth A Davis
(74) *Attorney, Agent, or Firm* — Mark S. Cohen; Pearl Cohen Zedek Latzer Baratz LLP

(57) ABSTRACT

The present application provides pharmaceutical compositions comprising a population of mononuclear-enriched cells in an early-apoptotic state, methods for the production of said compositions and uses thereof in the treatment of diseases characterized by pathological immune responses. The pharmaceutical compositions may be used in treatment of conditions such as, but not limited to, graft versus host disease (GVHD) and autoimmune diseases including but not limited to inflammatory bowel disease, gout and arthritis.

11 Claims, 27 Drawing Sheets

(56) References Cited

OTHER PUBLICATIONS

Burger et al.; "Concentration of citrate anticoagulant in peripheral blood progenitor cell collections", 1996, Transfusion, 36: 798-801.
Choi et al.; "Change in plasma tumor necrosis factor receptor 1 levels in the first week after myeloablative allogeneic transplantation correlates with severity and incidence of GVHD and survival", Blood., 2008 15;112(4):1539-42.
Copelan; "Hematopoietic stem-cell transplantation", N Engl J Med 2006; 354 (17):1813-1826.
Fadok et al.; "Macrophages that have ingested apoptotic cells in vitro inhibit proinflammatory cytokine production through autocrine/paracrine mechanisms involving TGF-beta, PGE2, and PAF", J Clin Invest, 1998; 101 (4):890-898.
Ferrara; "Pathogenesis of acute graft-versus-host disease: cytokines and cellular effectors", J Hematother Stem Cell Res 2000; 9 (3):299-306.
Ferrara et al.; "The pathophysiology of acute graft-versus-host disease", Int J Hematol 2003; 78 (3):181-187.
Ferrara et al.; "Acute graft versus host disease: pathophysiology, risk factors, and prevention strategies", Clin Adv Hematol Oncol 2005; 3 (5):415-419, 428.
Ferrara; "Novel strategies for the treatment and diagnosis of graft-versus-host-disease", Best Pract Res Clin Haematol., 2007, 20(I):91-7.
Filipovich et al.; "National Institutes of Health Consensus Development Project on Criteria for Clinical Trials in Chronic Graft-versus-Host Disease: I. Diagnosis and Staging Working Group Report", Biol Blood Marrow Transplant, 2005, vol. 11, Issue 12, Dec. 2005, pp. 945-956.
Gooley et al.; "Reduced Mortality after Allogeneic Hematopoietic-Cell Transplantation", N Engl J Med., 2010;363:2091-2101.
Hartmann, G. et al., "Specific Type IV Phosphodiesterase Inhibitor Rolipram Mitigates Experimental Colitis in Mice", The Journal of Pharmacology and Experimental Therapeutics, vol. 29 p. 222-230, 2000.
Horner et al., eds. SEER Cancer Statistics Review, 1975-2006. Bethesda, MD : National Cancer Institute, 2009. http://seer.cancer.gov/csr/1975_2006/.
Horowitz et al.; "Graft-versus-leukemia reactions after bone marrow transplantation. Blood", 1990;75:555-62.
Ichiki et al.; "T cell immunity and graft-versus-host disease (GvHD)", Autoimmun Rev, 2006; 5 (I):1-9.
International Search Report and Written Opinion for PCT/IL2013/051001 dated Mar. 25, 2014.
Izcue; "Special regulatory T-cell review: regulatory T cells and the intestinal tract—patrolling the frontier", 2008, Immunology, 123, 6-10.
Izcue; "Interleukin-23 Restrains Regulatory T Cell Activity to Drive T Cell-Dependent Colitis", 2008, Immunology, 28(4): 559-570.
Kao et al.; "Validation of short-term handling and storage conditions for marrow and peripheral blood stem cell products", 2011, Transfusion, 51: 137-147.
Kleinclauss et al.; "Administration of donor apoptotic cells: an alternative cell-based therapy to induce tolerance?", Transplantation 2003; 75 (9 Suppl):43S-45S.
Koreth et al.; "Current and future approaches for control of graft-versus-host disease", Expert Rev Hematol 2008, 1;(1):111.
Krispin et al., "Apoptotic cell thrombospondin-1 and heparin-binding domain lead to dendritic-cell phagocytic and tolerizing states", Blood. 2006;108:3580-3589.
Lee et al.; "Philadelphia chromosome-positive acute lymphoblastic leukemia: current treatment and future perspectives", Cancer. 2011;117:1583-94.
Li et al.; "Saving death: apoptosis for intervention in transplantation and autoimmunity", Clin Dev Immunol 2006; 13 (2-4):273-282.
Luznik et al.; "High-dose cyclophosphamide as single-agent, short-course prophylaxis of graft-versus-host disease", Blood. 2010;115:3224-30.
Matsumoto et al.; "Successful liquid storage of peripheral blood stem cells at subzero non-freezing temperature", 2002, Bone Marrow Transplantation, 30(11):777-784.
Mevorach et al.; Single Infusion of Donor Mononuclear Early Apoptotic Cells as Prophylaxis for Graft-versus-Host Disease in Myeloablative HLA-Matched Allogeneic Bone Marrow Transplantation: A Phase I/IIa Clinical Trial Biol Blood Marrow Transplant 20 (2014) , pp. 58-65.
Mevorach; "The role of death-associated molecular patterns in the pathogenesis of systemic lupus erythematosus", Rheum Dis Clin North Am 2004; 30 (3):487-504, viii.
Mevorach et al.; "Systemic exposure to irradiated apoptotic cells induces autoantibody production", J Exp Med 1998; 188 (2):387-392.
Mohty et al., "Inflammatory cytokines and acute graft-versus-host disease after reduced-intensity conditioning allogeneic stem cell transplantation", Blood. 2005; 106:4407-4411.
Okamoto et al.; "Increased hepatocyte growth factor in serum in acute graft-versus-host disease", BMT 2001, 28:197-200.
Paczesny et al.; "A biomarker panel for acute graft-versus-host disease", Blood., 2009, 8;113(2):273-8. Epub Oct. 2, 2008.
Peritt; "Potential mechanisms of photopheresis in hematopoietic stem cell transplantation", Biol Blood Marrow Transplant 2006; 12 (1 Suppl 2):7-12.
Perruche et al.; "Intravenous infusion of apoptotic cells simultaneously with allogeneic hematopoietic grafts alters anti-donor humoral immune responses", Am J Transplant, 2004; 4 (8):1361-1365.
Perruche et al.; "A single intravenous infusion of apoptotic cells, an alternative cell-based therapy approach facilitating hematopoietic cell engraftment, did not induce autoimmunity", J Hematother Stem Cell Res 2003; 12 (4):451-459.
Perruche et al.; "B Cell allogeneic responses after hematopoietic cell transplantation: is it time to address this issue?", Transplantation, 2005; 79 (3 Suppl):S37-39.
Przepiorka et al.; "1994 Consensus Conference on Acute GVHD Grading", Bone Marrow Transplant, 1995;15:825-8.
Reddy et al.; "Immunobiology of acute graft-versus-host disease", Blood Rev. 2003;17:187-94.
Saas et al.; "Cell-based therapy approaches using dying cells: from tumour immunotherapy to transplantation tolerance induction", Expert Opin Biol Ther 2002; 2 (3):249-263.
Sakata et al.; "Kinetics of plasma cytokines after hematopoietic stem cell transplantation from unrelated donors: the ratio of plasma IL-10/sTNFR level as a potential prognostic marker in severe acute graft-versus-host disease", Bone Marrow Transplant. 2001 27(11):1153-61.
Savill et al.; "A blast from the past: clearance of apoptotic cells regulates immune responses", Nat Rev Immunol 2002; 2 (12):965-975.
Sauter et al.; "Consequences of cell death: exposure to necrotic tumor cells, but not primary tissue cells or apoptotic cells, induces the maturation of immunostimulatory dendritic cells", J Exp Med 2000; 191 (3):423-434.
Stuart et al.; "Inhibitory effects of apoptotic cell ingestion upon endotoxin-driven myeloid dendritic cell maturation", J Immunol 2002; 168 (4):1627-1635.
Tassiulas et al.; "Apoptotic cells inhibit LPS-induced cytokine and chemokine production and IFN responses in macrophages", Hum Immunol 2007; 68 (3): 156-164.
Thomas et al.; "Marrow Transplantation for Acute Nonlynphoblastic Leukemia in First Remission", NEJM, 1979; pp. 597-599.
Vaux; "Toward an understanding of the molecular mechanisms of physiological cell death", Proc Natl Acad Sci U S A 1993; 90 (3):786-789.
Verbovetski et al.; "Opsonization of apoptotic cells by autologous iC3b facilitates clearance by immature dendritic cells, down-regulates DR and CD86, and up-regulates CC chemokine receptor 7", J Exp Med 2002; 196 (12):1553-1561.
Diaz et al. "Large-volume leukapheresis in pediatric patients: pre-apheresis peripheral blood CD34+ cell count predicts progenitor cell yield", Haematologica. Jan. 1999;84(1):32-5.
Elmas et al. "Activation of coagulation during alimentary lipemia under real-life conditions", Int J Cardiol. Jan. 8, 2007;114(2):172-5.

(56) References Cited

OTHER PUBLICATIONS

Erduran et al. "Apoptotic effects of heparin on lymphoblasts, neutrophils, and mononuclear cells: results of a preliminary in vitro study", Am J Hematol. Jun. 1999;61(2):90-3.

Goldman "A special report: bone marrow transplants using volunteer donors—recommendations and requirements for a standardized practice throughout the world—1994 update. The WMDA Executive Committee", Blood. Nov. 1, 1994;84(9):2833-9.

Kim "Therapeutic pediatric apheresis", J Clin Apher. 2000;15(1-2):129-57.

Larsen et al. "The link between high-fat meals and postprandial activation of blood coagulation factor VII possibly involves kallikrein", Scand J Clin Lab Invest. Feb. 2000;60(1):45-54.

Lee et al. "Anticoagulation techniques in apheresis: from heparin to citrate and beyond", J Clin Apher. 2012;27(3):117-25.

Manaster et al. "Heparin induces apoptosis in human peripheral blood neutrophils", Br J Haematol. Jul. 1996;94(1):48-52.

Saas et al., "Intravenous apoptotic cell infusion as a cell based therapy toward improving hematopoietic cell transplantation outcome", *Ann. N.Y. Acad. Sci.*, 1209, Oct. 2010, pp. 118-126.

Silveira et al. "In vivo demonstration in humans that large postprandial triglyceride-rich lipoproteins activate coagulation factor VII through the intrinsic coagulation pathway", Arterioscler Thromb Vasc Biol. Nov. 1996;16(11):1333-9.

Voak et al. "Guidelines for the collection, processing and storage of human bone marrow and peripheral stem cells for transplantation", Transfusion Medicine vol. 4, Issue 2 Jun. 1994 pp. 165-172.

Wright et al. "Citrate anticoagulation using ACD solution A during long-term haemodialysis", Nephrology (Carlton). May 2011;16(4):396-402.

Zaguri et al. "'Danger' effect of low-density lipoprotein (LDL) and oxidized LDL on human immature dendritic cells", Clin Exp Immunol. Sep. 2007;149(3):543-52.

Mevorach et al. "Early apoptotic cells cellular treatment in allogeneic haematopoietic cell transplantation" Bone Marrow Transplantation. Apr. 1, 2011;46:S312-3.

Erduran et al. "In vitro determination of apoptotic effect of heparin on lymphoblasts by using flow cytometric DNA analysis and measurements of caspase-9 activation and cytochrome C level" Journal of pediatric hematology/oncology. Jan. 1, 2012;34(1):e26-9.

Frabetti et al. "White cell apoptosis in packed red cells" Database BIOSIS [Online] Biosciences Information Service; Nov. 1998; XP002777751, Database accession No. PREV199900041644. Abstract. (Also Transfusion. Nov. 12, 1998;38(11-12):1082-9).

Supplementary European Search Report for European Application No. 13860154.7 dated Feb. 16, 2018.

Vianello et al. "Heparin Induces Apoptosis in Lymphocytes from B-cell Chronic Lymphocytic Leukemia" Hematology. Jan. 1, 1998;3(6):451-63.

* cited by examiner

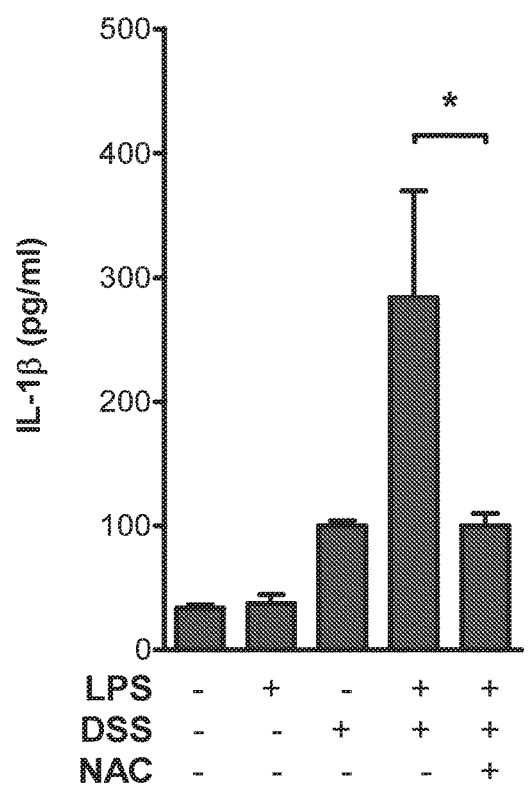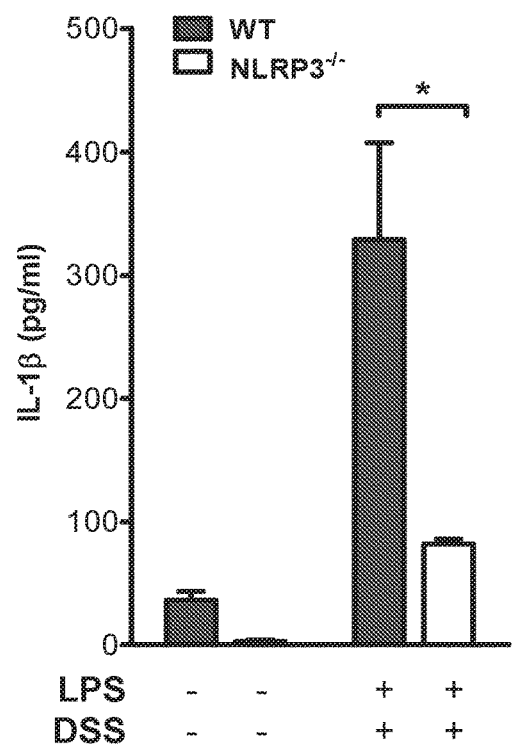
Figure 9C
Figure 9D

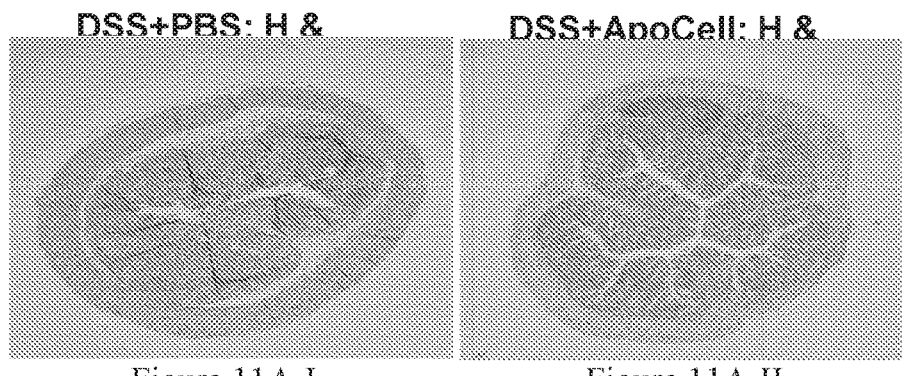
Figure 11A-I    Figure 11A-II
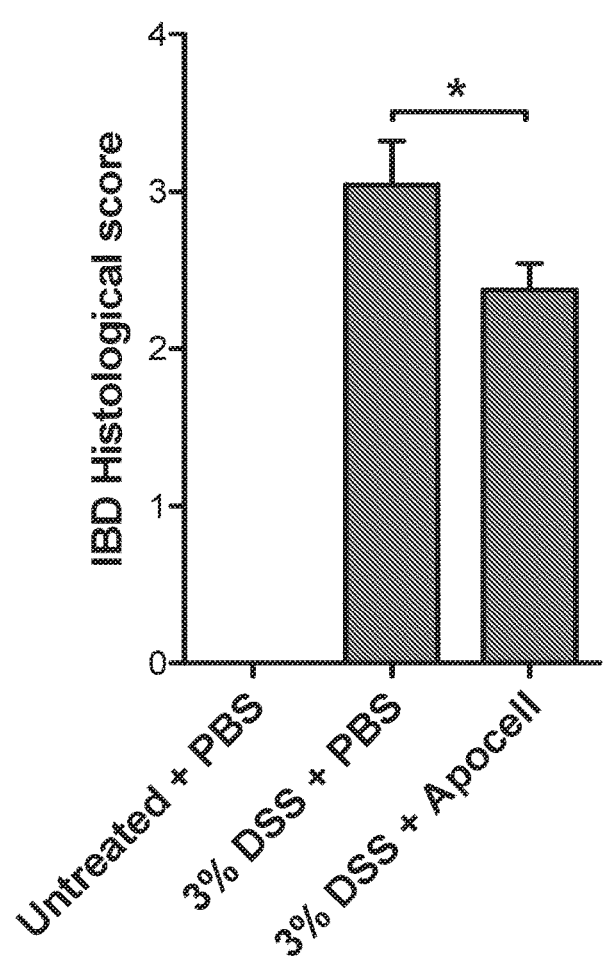
Figure 11A-III

Untreated colon. Control of H and secondary antibody
 Untreated colon. Control of H and MPO staining
 DSS treated colon. H and MPO staining
 ApoCell & DSS treated colon. H & MPO staining

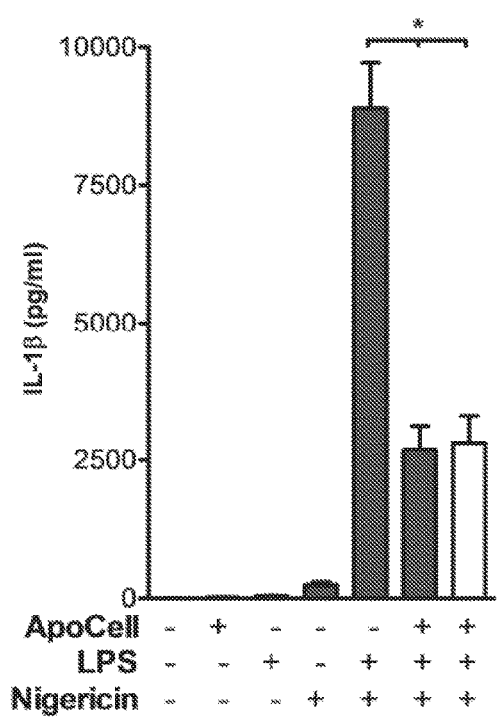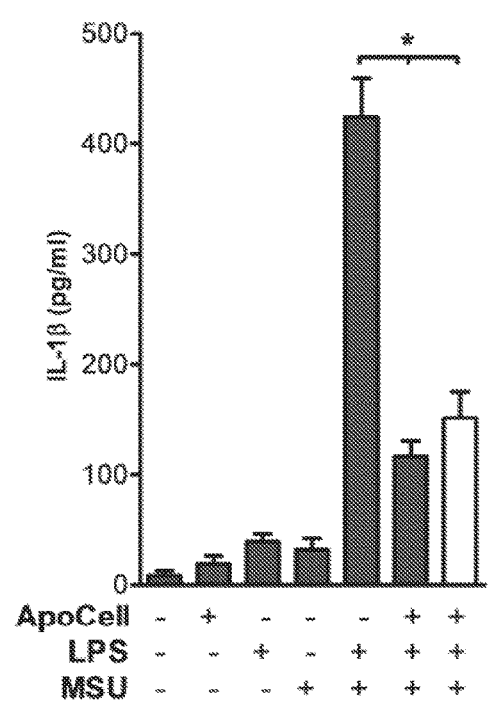
Figure 15C                                    Figure 15D

THERAPEUTIC APOPTOTIC CELL PREPARATIONS, METHOD FOR PRODUCING SAME AND USES THEREOF

CROSS-REFERENCE TO RELATED APPLICATIONS

This application is a National Phase Application of PCT International Application No. PCT/IL2013/051001, International Filing Date Dec. 5, 2013, claiming priority of U.S. Provisional Patent Applications Nos. 61/733,936, filed Dec. 6, 2012; 61/778,497, filed Mar. 13, 2013; and 61/872,884, filed Sep. 3, 2013, which are hereby incorporated by reference in their entirety.

FIELD OF THE INVENTION

The present invention relates to a therapeutic cell population comprising apoptotic cells and, more particularly, to compositions comprising mononuclear enriched cells in an early apoptotic state, methods for the production thereof, and uses thereof in treatment of diseases characterized by pathological immune responses.

BACKGROUND OF THE INVENTION

Diseases characterized by pathological immune responses include many diseases associated with significant mortality and morbidity, particularly autoimmune diseases, such as systemic lupus erythematosus (SLE), and transplantation-related diseases such as graft-versus-host disease (GVHD). Autoimmune diseases may generally be divided into two general types, namely systemic autoimmune diseases (e.g. SLE and scleroderma), and organ specific autoimmune diseases, such as multiple sclerosis, and diabetes.

Immunosuppressive drugs have been used for treatment or prevention of the rejection of transplanted organs and tissues (e.g., bone marrow, heart, kidney, liver); for treatment of autoimmune diseases or diseases that are most likely of autoimmune origin (e.g., rheumatoid arthritis, multiple sclerosis, myasthenia gravis, systemic lupus erythematosus, sarcoidosis, Crohn's disease, Behcet's Disease, pemphigus, uveitis and ulcerative colitis); treatment of some other non-autoimmune inflammatory diseases (e.g., long term allergic asthma control) as well as transplantation-related diseases (e.g. GVHD). However, immunosuppressive drug treatments can lead to many complications, and improved methods for dealing with pathological immune reactions are needed.

Approximately 30,000 patients annually in the U.S. and Europe undergo allogeneic bone marrow transplantation (BMT). In allogeneic bone marrow transplantation (alloBMT), the infusion of donor marrow into the patient's body entails the interaction of cells from two immune systems. Conditioning regimens for patients receiving allogeneic transplants allow the donor stem cells to engraft in the patient by suppressing the immune system. Once the donor's immune cells are established in the patient's body, they may recognize the patient's own tissue and cells, including any residual cancer cells, as being different or foreign. The immune system may then cause damage to certain organs such the liver, gastrointestinal tract or skin; this effect is known as graft-versus-host disease (GVHD).

As of today, GVHD prophylaxis comprises the combination of immunosuppressive drugs including a calcineurin inhibitor (CNI), cyclosporine or tacrolimus, and either methotrexate, mycophenolate mofetil (MMF), or sirolimus. However, acute GVHD still occurs in 35% to 70% of BMT patients who receive transplants from human leukocyte antigen (HLA)-matched siblings, and even more frequently in unrelated donor transplant recipients.

Although calcineurin inhibitors (CNIs) partially inhibit acute GVHD, they may impair immune reconstitution by inhibiting T-cell development and increasing the risk of disease relapse. Thus, patients with hematologic malignancies undergoing allogeneic BMT are in need of GVHD prophylaxis that would minimize the use of CNIs, prevent GVHD, and retain a functional immune system including a beneficial graft-versus-tumor effect.

U.S. Pat. Nos. 6,524,865, 6,607,722 and 7,109,031, and US patent applications 2010/0267137, 2010/01837365 relate to the production of immunosuppressive recipient dendritic cells, and contacting the dendritic cells with necrotic or apoptotic donor leukocytes, intended to reduce immune response to grafts or implants.

WO 2002/060376, to one of the inventors of the present application, discloses a method of treatment of a systemic autoimmune disease in a subject by administration of apoptotic and/or necrotic cells obtained from said subject.

WO 2006/117786, to one of the inventors of the present application, further discloses the use of a cell-preparation comprising dying or dead leukocytes for treatment of a disease characterized by a pathological immune response. The dying or dead leukocytes are obtained by inducing live leukocytes to adhere to a surface, and are capable of suppressing the pathological immune response in the subject.

A study by Mevorach et al., published after the priority date of the present application, examined infusion of donor mononuclear early apoptotic cells as prophylaxis for acute graft-versus-host disease (GVHD) after HLA-matched myeloablative allogeneic hematopoietic stem cell transplantation (HSCT) from a related donor (Mevorach et al., ePub October 2013, Biol Blood Marrow Transplant).

During blood cell collection the use of anticoagulants is routine. During cell storage the use of anticoagulants has been reported to improve cell yield. Matsumoto et al. compared storage of peripheral blood stem cells (PBSC) under various conditions, including storage in University of Wisconsin (UW) solution and hypothermic preservation in autologous serum and the anticoagulant solution acid-citrate-dextrose (ACD) solution A. The survival of colony-forming unit granulocyte-macrophages (CFU-GM) was found to be significantly better in UW solution than the survival achieved with hypothermic preservation in autologous serum and ACD-A solution at 4° C. or cryopreservation at 80° C. (Matsumoto et al., 2002, Bone Marrow Transplantation, 30(11):777-784). Burger et al. disclosed that addition of heparin to plasma collected for cryopreservation of cells or addition of ACD-A prevented gelation of freezing solution (Burger, S. R. et al, 1996, Transfusion, 36: 798-801). WO 2003/006691 discloses a cell cryopreservation medium for CD34+ cells comprising heparin. Kao et. al. discloses storage of bone marrow cell, peripheral blood stem cell or peripheral blood mononuclear cell products at 4° C. or 20° C. in media comprising ACD-A and/or heparin (Kao et al., 2011, Transfusion, 51: 137-147). U.S. Pat. No. 6,489,311 discloses use of anticoagulants to prevent cell apoptosis.

There remains an unmet need for compositions and methods for treating or preventing immune disorders including autoimmune and inflammatory diseases and transplantation related diseases. For instance, GVHD, with an estimated incidence of 30%-70%, remains the main barrier for successful allogeneic blood or marrow transplantation, and the optimal approach for GVHD prophylaxis has not yet been established. In particular it is essential to obtain compositions and methods that prevent or ameliorate GVHD in a safe, reliable, reproducible and effective manner.

SUMMARY OF THE INVENTION

The present invention relates to a therapeutic population of early apoptotic cells. In particular, the present invention provides well defined preparations of therapeutic mononuclear enriched cells at an early-apoptotic state, improved methods for the production thereof, and the use thereof in a clinical setting in treatment of diseases characterized by pathological immune responses. Examples of such diseases include, but are not limited to, graft versus host disease (GVHD), Crohn's disease and ulcerative colitis. In addition, the present invention provides methods to obtain therapeutic compositions comprising mononuclear enriched early stage apoptotic cells with a stable and reproducible cell yield, and uses thereof.

The present invention is based, in part, on the finding that mononuclear-enriched early-state apoptotic cells administered in a separate infusion, in addition to the transplantation of bone marrow cells, have an ameliorative or prophylactic effect on GVHD. In particular, infusion of the apoptotic cell preparation of the invention to subjects suffering from hematological malignancies who receive hematopoietic stem-cell transplantation (HSCT), was effective in reducing the incidence of acute high grade GVHD (e.g., grade II-IV). In addition, the apoptotic cell preparation remarkably reduced the incidence of hepatotoxicity in said subjects and was found in some instances to reduce the time to engraftment of the HSCT.

The present invention is also based, in part, on the finding that a single infusion of the apoptotic cell composition of the invention significantly ameliorated both the clinical score and histological damage in two different animal models of IBD.

During reduction to practice of the present invention in a clinical setting, the inventors encountered a problem in that producing the cell preparation of the invention from blood of certain donors results in a low and/or unstable cell yield between different preparations. In some instances cell yield was adversely affected by formation of cell aggregates in the resulting composition. This problem was especially prevalent in compositions produced using cells from donors having high levels of blood triglycerides. In order to overcome these problems, of low cell yield and/or formation of aggregates, it was found that use of an anticoagulant during one or more stages of induction of apoptosis (in addition to anticoagulant routinely used during cell collection) results in a high and stable cell yield in the composition. Furthermore, addition of anticoagulant during one or more stages of induction of apoptosis enabled maintenance of a high and stable cell yield within different preparations of the composition of the invention, regardless of the protocol used for cell collection. According to some embodiments, as exemplified herein below, addition of anticoagulant during one or more stages of induction of apoptosis enables production of a composition with a high and stable cell yield of at least 30%, preferably at least 40%, typically at least 50% cells of the initial cells subjected to apoptosis induction. Each possibility represents a separate embodiment of the present invention.

As exemplified herein below, such a high and stable cell yield is observed both when producing the cell composition in the presence of high or normal triglyceride levels. According to some embodiments, use of an anticoagulant during one or more stages of production of the cell composition of the invention results in a high and stable cell yield of viable cells in the composition and/or of cells in an early-apoptotic stage in the composition. Each possibility represents a separate embodiment of the present invention. Thus, the present invention provides an early-apoptotic, stable and highly viable mononuclear-enriched cell composition, improved methods of producing said cell composition and use thereof in treating or ameliorating autoimmune and inflammatory diseases.

According to one aspect, the present invention provides a cell preparation comprising mononuclear-enriched cells, wherein the preparation comprises at least 85% mononuclear cells, wherein at least 40% of the cells in the preparation are in an early-apoptotic state, wherein at least 85% of the cells in the preparation are viable cells and wherein the preparation comprises no more than 15% $CD15^{high}$ expressing cells.

According to another aspect, the present invention provides a composition comprising the cell preparation of the invention. According to some embodiments a composition comprising said cell preparation further comprises an anticoagulant. According to some embodiments the anti-coagulant is selected from heparin and ACD Formula A or combinations thereof. Each possibility represents a separate embodiment of the present invention. According to some embodiments, the heparin in the composition comprising the final suspension medium used for administration of said cell preparation to a patient is present at a concentration between 0.005 U/ml and 2.5 U/ml. According to some alternative embodiments, the heparin in the composition comprising the final suspension medium used for administration of said cell preparation to a patient is present at a concentration between 0.01 U/ml and 1 U/ml. According to some embodiments, the ACD Formula A in the composition comprising the final suspension medium used for administration of said cell preparation to a patient is present at a concentration of 0.01%-10% v/v. According to other embodiments, the ACD Formula A in the composition comprising the final suspension medium used for administration of said cell preparation to a patient is present at a concentration of 0.05%-5% v/v.

According to some embodiments, the composition of the invention further comprises residual methylprednisolone at a concentration that does not exceed 30 μg/ml. According to some embodiments, the composition of the invention further comprises no more than 10% $CD15^{high}$ expressing cells.

According to some embodiments, the cells in the cell-preparation of the invention are collected from an allogeneic donor. According to some embodiments, the cells in the cell-preparation of the invention are collected from the same donor as a donor of Hematopoietic Stem Cells (HSCs) used for a Hematopoietic Stem Cell Transplantation (HSCT) procedure. According to a non-limiting example, collection of cells from a donor is effected by leukapheresis. According to certain embodiments the mononuclear enriched cell preparation will contain autologous cells.

It is to be noted that, as known in the art, anti-coagulants are regularly used during cell-collection procedures, such as, but not limited to, leukapheresis. According to some embodiments of the present invention, anticoagulant is further added to at least one medium used during preparation of the composition of the invention. According to some embodiments, the at least one medium used during preparation of the composition of the invention is selected from the group consisting of: the freezing medium, the washing medium, the apoptosis inducing incubation medium and combinations thereof. Each possibility represents a separate embodiment of the present invention. According to some embodiments, the anti-coagulant is selected from the group consisting of: Heparin, ACD Formula A and a combination thereof. Each possibility represents a separate embodiment of the present invention. It is to be noted that other anti-coagulants known in the art may be used according to the present invention, such as, but not limited to Fondaparinaux, Bivalirudin and Argatroban.

According to some embodiments, at least one medium used during preparation of the composition of the invention contains 5% of ACD formula A solution comprising 10 U/ml heparin. According to a typical embodiment, anti-coagulant is not added to the final suspension medium of the cell composition of the invention. As used herein, the terms "final suspension medium" and "administration medium" are used interchangeably.

According to some embodiments, at least one medium used during preparation of the composition of the invention comprises heparin at a concentration of between 0.1-2.5 U/ml. According to some embodiments, at least one medium used during preparation of the composition of the invention comprises ACD Formula A at a concentration of between 1%-15% v/v. According to some embodiments, the freezing medium comprises an anti-coagulant. According to other embodiments, the incubation medium comprises an anti-coagulant. According to preferred embodiments, both the freezing medium and incubation medium comprise an anti-coagulant. According to some embodiments the anti-coagulant is selected from the group consisting of: heparin, ACD Formula A and a combination thereof. Each possibility represents a separate embodiment of the present invention.

According to some embodiments, the heparin in the freezing medium is at a concentration of between 0.1-2.5 U/ml. According to some embodiments, the ACD Formula A in the freezing medium is at a concentration of between 1%-15% v/v. According to some embodiments, the heparin in the incubation medium is at a concentration of between 0.1-2.5 U/ml. According to some embodiments, the ACD Formula A in the incubation medium is at a concentration of between 1%-15% v/v. According to specific embodiments, the anticoagulant is a solution of acid-citrate-dextrose (ACD) formula A. In additional embodiments, exemplified herein below, the anticoagulant added to at least one medium used during preparation of the composition of the invention is ACD Formula A containing heparin at a concentration of 10 U/ml.

In some embodiments, the mononuclear enriched cell preparation of the invention comprises at least 85% mononuclear cells, preferably at least 90% mononuclear cells. Each possibility is a separate embodiment of the invention. According to some embodiments, the cell preparation comprises at least 90% mononuclear cells. According to some embodiments, the cell preparation comprises at least 95% mononuclear cells.

In additional embodiments, the mononuclear enriched cell preparation comprises cell types selected from the group consisting of: lymphocytes, monocytes and natural killer cells. In another embodiment, the mononuclear enriched cell preparation comprises no more than 15%, alternatively no more than 10%, typically no more than 5% polymorphonuclear leukocytes, also known as granulocytes (i.e., neutrophils, basophils and eosinophils). Each possibility represents a separate embodiment of the present invention. In yet another embodiment, the mononuclear enriched cell preparation comprises no more than 15%, alternatively no more than 10%, typically no more than 5% $CD15^{high}$ expressing cells. Each possibility represents a separate embodiment of the present invention.

According to another aspect, the present invention provides a method for producing the composition of the invention, the method comprising:

obtaining a mononuclear-enriched cell preparation from the peripheral blood of a donor, said mononuclear-enriched cell preparation comprising at least 65% mononuclear cells;

freezing the mononuclear-enriched cell preparation in a freezing medium;

thawing the mononuclear-enriched cell preparation;

incubating the mononuclear-enriched cell preparation in an apoptosis inducing incubation medium comprising methylprednisolone at a final concentration of about 10-100 µg/mL;

wherein at least one of the freezing medium and the apoptosis inducing incubation medium comprise an anti-coagulant; and suspending said cell preparation in an administration medium, thereby providing the composition of the invention.

According to some embodiments, the apoptosis inducing incubation medium used in the production method of the invention comprises an anti-coagulant. According to some embodiments, both the freezing medium and apoptosis inducing incubation medium used in the production method of the invention comprise an anti-coagulant. Without wishing to be bound by any theory or mechanism, in order to maintain a high and stable cell yield in different cell compositions, regardless of the cell collection protocol, it is preferable to add anti-coagulants to both the freezing medium and apoptosis inducing incubation medium during production of the composition of the invention. According to some embodiments, a high and stable cell yield within the composition of the invention is a cell yield of at least 30%, preferably at least 40%, typically at least 50% cells of the initial population of cells used for induction of apoptosis. Each possibility represents a separate embodiment of the present invention. As used herein, the terms "incubation medium" and "apoptosis inducing incubation medium" are used interchangeably.

According to some embodiments, the mononuclear-enriched cell composition is frozen for at least about 6 hours. According to some embodiments, the mononuclear-enriched cell composition is frozen for at least about 12 hours. According to some embodiments, the mononuclear-enriched cell composition is frozen for about 12 hours. According to some embodiments, the mononuclear-enriched cell composition is frozen for at least 8, 10, 12, 18, 24 hours. Each possibility represents a separate embodiment of the present invention.

According to some embodiments, incubating the thawed cells according to the method of the invention is over a period of about 2-12 hours, possibly about 4-8 hours, typically for about 6 hours. Each possibility represents a separate embodiment of the present invention. According to some embodiments, incubating according to the method of the invention is incubating for about 6 hours. According to some embodiments, incubating is for at least 6 hours.

According to some embodiments, obtaining a mononuclear-enriched cell preparation is effected by leukapheresis. According to certain embodiments, obtaining a mononuclear-enriched cell preparation according to the production method of the invention refers to obtaining a preparation comprising at the time of collection at least 65%, possibly at least 70%, typically at least 80% mononuclear cells. Each possibility represents a separate embodiment of the present invention.

According to some embodiments, the freezing, according to the production method of the invention, is the first step in inducing the early apoptotic state of the mononuclear cells in the cell preparation of the invention. As used herein, the terms "freezing" and "cryopreservation" are used interchangeably.

According to some embodiments, the apoptosis inducing incubation medium comprises an apoptosis inducing agent, and incubation in such medium presents a second step in inducing the early apoptotic state of the cells in the cell preparation of the invention. According to some embodiments the apoptosis inducing agent is methylprednisolone.

According to some embodiments, the incubation medium comprises methylprednisolone at a final concentration of about 5-100 µg/mL, possibly about 40-60 µg/mL. Each possibility represents a separate embodiment of the present invention. According to some embodiments, the incubation medium comprises methylprednisolone at a final concentration of about 50 µg/ml.

According to some embodiments, the cell concentration during the incubating is in the range of about $0.5 \times 10^6$-$10 \times 10^6$. According to certain embodiments, the cell concentration during incubation is about $5 \times 10^6$ cells/ml.

According to another aspect, the present invention provides a method of preventing or ameliorating an immune disease or an autoimmune disease or an inflammatory disease in a subject in need thereof, comprising administering the pharmaceutical composition of the invention to the subject. Each possibility represents a separate embodiment of the present invention.

According to some embodiments, the immune disease is GVHD. According to some embodiments, the immune disease is high grade GVHD. According to some embodiments, the present invention provides a method of preventing or ameliorating GVHD in a subject in need thereof, comprising administering the pharmaceutical composition of the invention to the subject.

According to some embodiments, the GVHD is ameliorated to prevent the occurrence of high grade GVHD. According to specific embodiments, high grade GVHD is grade II-IV GVHD. According to another specific embodiment, high grade GVHD is grade III-IV GVHD. According to a particular embodiment, the pharmaceutical composition induces a shift from high grade GVHD to grade I GVHD. According to another embodiment, the GVHD is acute GVHD. According to yet another embodiment, the GVHD is chronic GVHD. According to another particular embodiment, the method of administering to the subject a pharmaceutical composition comprising said mononuclear enriched cell preparation prevents high grade GVHD while the subject retains a graft-versus-tumor or graft-versus-leukemia (GVL) effect. According to some embodiments, following the treatment method of the invention the subject retains the graft-versus-leukemia (GVL) effect.

According to another embodiment, the pharmaceutical composition reduces hepatotoxicity associated with GVHD. According to some embodiments, said GVHD is liver GVHD.

According to another embodiment, the subject is undergoing hematopoietic stem-cell transplantation (HSCT). According to some embodiments, the HSCT is allogeneic HSCT. According to some embodiments, the HSCT is allogeneic HSCT and the pharmaceutical composition of the invention comprises cells obtained from the same donor of the hematopoietic stem-cells. According to particular embodiments, said subject is suffering from a hematopoietic malignancy. According to another embodiment, the hematopoietic malignancy is selected from leukemia, myelodysplastic syndrome (MDS), lymphoma, and multiple myeloma (i.e., plasma cell dyscrasia). Each possibility represents a separate embodiment of the present invention. According to exemplary embodiments, said hematopoietic malignancy is selected from the group consisting of acute lymphoblastic leukemia (ALL), acute myeloid leukemia (AML), myelodysplastic syndrome (MDS) and chronic myelogenous leukemia (CML). Each possibility represents a separate embodiment of the present invention.

In other embodiments, the subject is undergoing solid organ transplantation. Solid organ transplantations include but are not limited to an organ selected from lung, heart, kidney, pancreas, liver and small-bowel. Each possibility represents a separate embodiment of the present invention. According to some embodiments, the pharmaceutical composition of the invention comprises cells obtained from the same or a different donor than the organ transplanted. According to some embodiments, the apoptotic cells of the invention are autologous cells.

According to another embodiment, the pharmaceutical composition is administered following a conditioning treatment administered to the transplantation recipient. According to another embodiment, the pharmaceutical composition is administered between one day prior to transplantation and 15 days following the transplantation. According to another embodiment, the administering of the pharmaceutical composition is carried out up to 30 hours prior to the transplantation. According to some embodiments, the administering of the pharmaceutical composition is carried out up to 24 hours prior to the transplantation. According to a particular embodiment, the administering of the pharmaceutical composition is carried out about 24-30 hours prior to the transplantation. According to yet another embodiment, the administering of the pharmaceutical composition is carried out at the same time as the transplantation.

According to some embodiments the pharmaceutical composition is administered intravenously. According to another embodiment, the pharmaceutical composition is administered in a single dose. According to alternative embodiments the pharmaceutical composition is administered in multiple doses. According to some embodiments, the pharmaceutical composition is formulated for intravenous injection.

According to additional embodiments, the inflammatory disease is arthritis, including, but not limited to, rheumatoid arthritis. According to some embodiments, the present invention provides a method of preventing or ameliorating arthritis in a subject in need thereof, comprising administering the pharmaceutical composition of the invention to the subject. According to another embodiment, the inflammatory disease is gout. According to some embodiments, the present invention provides a method of preventing or ameliorating gout in a subject in need thereof, comprising administering the pharmaceutical composition of the invention to the subject.

According to yet another embodiment, the inflammatory disease is inflammatory bowel disease. According to some embodiments, the inflammatory bowel disease is selected from Crohn's Disease, ulcerative colitis and a combination thereof. Each possibility represents a separate embodiment of the present invention. According to some embodiments, the present invention provides a method of preventing or ameliorating an inflammatory disease selected from the group consisting of: Crohn's Disease and ulcerative colitis in a subject in need thereof, comprising administering the pharmaceutical composition of the invention to the subject. Each possibility represents a separate embodiment of the present invention.

According to some embodiments, the present invention provides the pharmaceutical composition of the invention for use in preventing or ameliorating an immune disease or an autoimmune disease or an inflammatory disease in a subject.

According to some embodiments, the present invention provides the pharmaceutical composition of the invention for use in preventing or ameliorating GVHD in a subject. Each possibility represents a separate embodiment of the present invention. According to some embodiments, the present invention provides the pharmaceutical composition of the invention for use in preventing or ameliorating an inflammatory bowel disease selected from the group consisting of: Crohn's Disease and ulcerative colitis in a subject. Each possibility represents a separate embodiment of the present invention.

According to some embodiments, the present invention provides the pharmaceutical composition of the invention for the preparation of a medicament for preventing or ameliorating an immune disease or an autoimmune disease or an inflammatory disease. Each possibility represents a separate embodiment of the present invention.

Other objects, features and advantages of the present invention will become clear from the following description and drawings.

BRIEF DESCRIPTION OF THE DRAWINGS

FIGS. 9A-D are bar graphs comparing IL-1β release by murine primary resident peritoneal macrophages (pMΦ) treated with 3% DSS and/or LPS. The effect on IL-1β release was determined in the supernatant by ELISA following treatment with either (9A) extracellular K$^+$ (130 mM), (9B) bafilomycin A1 (10 nM) or (9C) ROS inhibitor N-acetyl-L-cysteine (NAC) (20 mM). (9D) IL-1β release following treatment with 3% DSS and/or LPS was further determined in pMΦ extracted from wild type (WT) or NLRP3-deficient mice (Nlrp3−/−). Shown are representative data as means±SEM of 3 to 5 independent experiments done in triplicate (*p<0.05, **p<0.01, t test).

FIG. 11A shows the histological appearance and histological colitis severity score of distal colon sections. H&E appearance (11A-I and 11A-II) and histological score (11A-III) of distal colon sections are shown for DSS-treated Balb/c mice (11-AI, 3% DSS+PBS) and DSS- and ApoCell-treated mice (11A-II, 3% DSS+ApoCell). Results from 3 independent experiments (*p<0.05, unpaired t-test).

FIGS. 15A-E are bar graphs comparing the effect of apoptotic cells (ApoCell) on IL-1β release from murine pMΦ macrophages. (15A) Macrophages were treated with LPS and/or 3% DSS or treated with apoptotic cells (1:8) prior to LPS and/or 3% DSS treatment. Shown are representative data as means±SEM of 3 independent experiments done in triplicate (*p<0.01, t-test). (15B) treated with LPS and/or 3% DSS or treated with apoptotic cells (1:8) prior to LPS and/or 3% DSS treatment. In some treatments, cells were incubated with 2 μM cytochalasin D for 45 min before the addition of apoptotic cells and DSS challenge. Shown are representative data as means±SEM of 2 independent experiments done in triplicate (*p<0.01, one way ANOVA). (15C-E) pMΦ cells were incubated either in the presence of apoptotic cells for 2 h followed by LPS priming for 1 h (black bar), or first primed with LPS for 1 h and then incubated with apoptotic cells for 2 h (white bar). According to some treatments, the pMΦ cells were then incubated with various inflammasome inducers: Nigericin 2.5 μM (13C), monosodium urate (MSU) 200 μg/ml (15D) or calcium pyrophosphate dihydrate (CPPD) 200 μg/ml (15E). IL-1β was determined in the supernatant by ELISA. Shown are representative data as means±SEM of 3 independent experiments done in duplicates (*p<0.001, one way ANOVA.

DETAILED DESCRIPTION OF THE INVENTION

The present invention, in some embodiments thereof, relates to an apoptotic cell population and, more particularly, to early-apoptotic mononuclear enriched cell preparations. The present invention further relates to methods for the production of said cell preparation, and the use thereof in the clinical setting, in treatment of diseases characterized by pathological immune responses.

Transplantation-Related Diseases

Results of clinical trials of single-infusion of early-apoptotic mononuclear-enriched cells, produced by ex-vivo induction of apoptosis in donor cells, indicate the safety and efficacy of these apoptotic cell populations for prevention, prophylaxis and/or amelioration of transplantation-related diseases, such as graft versus host disease (GVHD) in bone marrow transplant patients. As detailed herein below, induction of early-apoptosis in enriched mononuclear cells, according to the methods of the present invention, provided a clinical grade population of apoptotic allogeneic donor cells which, when infused with the bone marrow derived cells from the same donor, affected important factors associated with transplantation, and effectively reduced the incidence of GVHD in subjects with hematological malignancies.

Particularly, at 100 days post transplantation, incidence of Grade II-IV GVHD was reduced in HSC transplant recipients treated with the apoptotic donor cells prepared and the non-relapsed survival rate was significantly increased. As demonstrated herein, the incidences of acute grades II through IV and grades III through IV GVHD were very low (23% and 15% respectively) in comparison with control (71% grade II-IV). Remarkably, treatment with higher dosages of the apoptotic cell preparations ($140 \times 10^6$ and $210 \times 10^6$ apoptotic cells) showed 0% acute GVHD grade II-IV (compared to 50% of the matched historical controls).

Further, infusion of the apoptotic donor cells prepared according to the methods of the invention was effective in reducing the time to engraftment of the HSC and remarkably reducing the incidence of hepatotoxicity in HSC transplant recipients.

Figure 1:
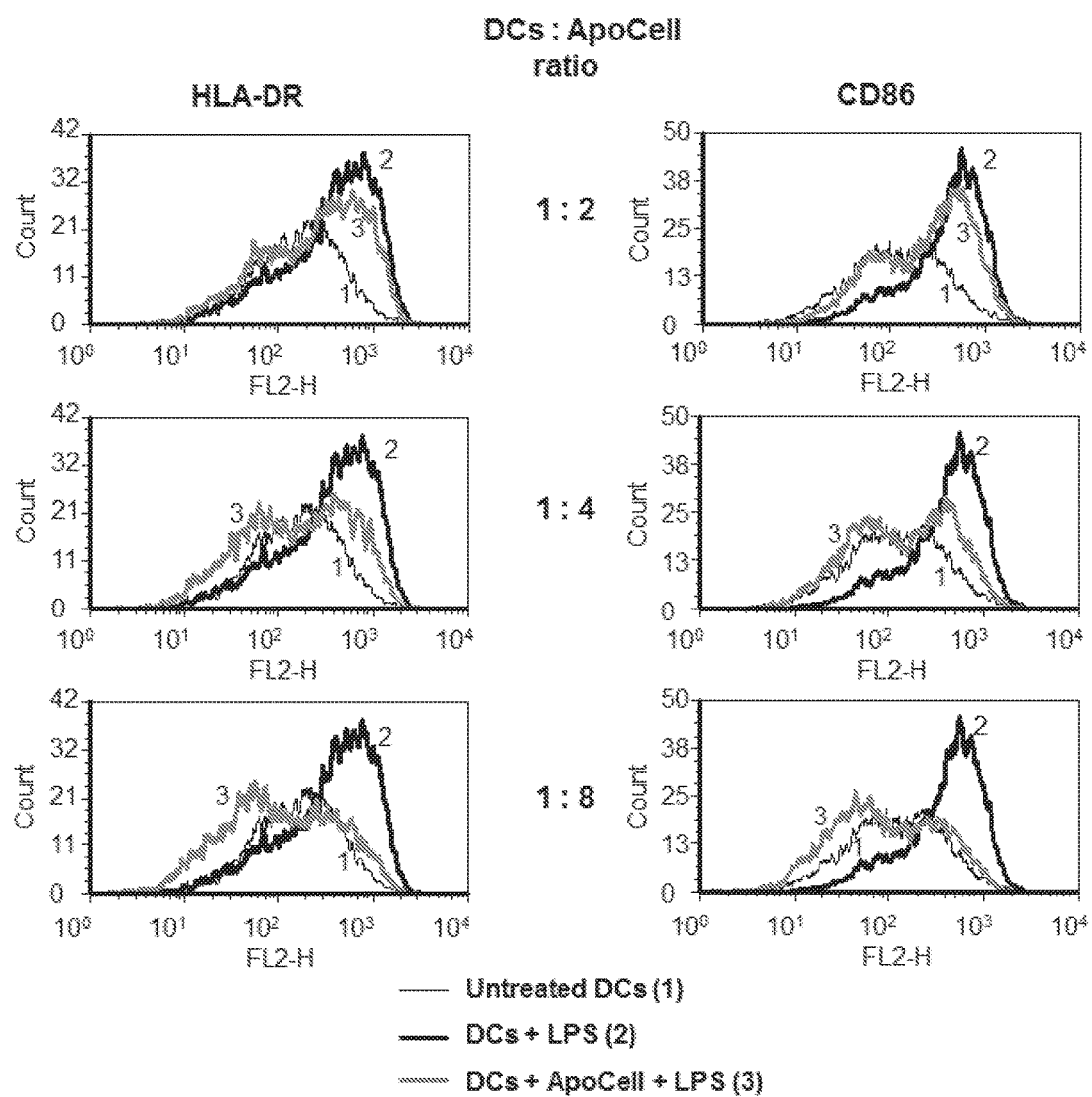
FIG. 1 depicts an in-vitro potency assay indicating inhibition of immature dendritic cell (iDC) maturation following interaction with the ApoCell cell preparation. The tolerogenic effect of the apoptotic cell preparation was examined following interaction with LPS treated iDCs, and detection of HLA-DR and CD86 expression levels. The results are representative of one patient.

While preventing induction of pro-inflammatory cytokines induced by GVHD has been a challenge for clinical application, the results demonstrated herein show reduced serum levels of GVHD-related factors in HSC transplant recipients who received the apoptotic cell compositions of the invention (FIG. 6). In particular, plasma levels of six different biomarkers: TNFRI, IL-2Ra, HGF, IL-8, IL-15 and IL-7, distinguished well between high to low grade or no-GVHD. Additional two control cytokines (IL-1b and IL-6) further emphasized the specificity of findings. Further, in-vitro potency assay clearly showed inhibition of DC maturation following interaction with the apoptotic cell preparations of the invention (FIG. 1).

According to some embodiments, the present invention provides a method of preventing or ameliorating GVHD in a subject undergoing HSCT, comprising administering to the subject the pharmaceutical composition of the invention.

According to some embodiments, the present invention provides a method of preventing or ameliorating GVHD in a subject undergoing HSCT, comprising administering to the subject the pharmaceutical composition of the invention. According to some embodiments, the present invention provides a method of preventing or ameliorating GVHD in a subject undergoing HSCT, comprising administering to the subject the pharmaceutical composition of the invention comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes. According to some embodiments, the present invention provides a method of preventing or ameliorating GVHD in a subject undergoing HSCT, comprising administering to the subject the pharmaceutical composition of the invention comprising a cell preparation comprising mononuclear enriched cells, wherein the preparation comprises at least 85% mononuclear cells, wherein at least 40% of the cells in the preparation are in an early apoptotic state and wherein at least 85% of the cells in the preparation are viable cells.

According to some embodiments, the present invention provides a method of preventing or ameliorating GVHD in a subject undergoing HSCT, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes; and wherein the pharmaceutical composition comprises an anti-coagulant selected from the group consisting of: heparin, ACD Formula A and a combination thereof. Each possibility represents a separate embodiment of the present invention. According to some embodiments, the present invention provides a method of preventing or ameliorating GVHD in a subject undergoing HSCT, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state and wherein at least 85% of the cells in the preparation are viable cells; and wherein the pharmaceutical composition comprises an anti-coagulant selected from the group consisting of: heparin, ACD Formula A and a combination thereof. Each possibility represents a separate embodiment of the present invention.

According to some embodiments, the heparin in the pharmaceutical composition of the invention is present at a concentration between 0.001 U/ml and 3 U/ml, typically between 0.001 U/ml and 2.5 U/ml. According to some embodiments, the heparin in the pharmaceutical composition of the invention is present at a concentration between 0.005 U/ml and 2.5 U/ml. According to other embodiments, the heparin in the pharmaceutical composition is present at a concentration between 0.01 U/ml and 1 U/ml. According to some embodiments, the ACD Formula A in the pharmaceutical composition of the invention is present at a concentration of 0.01%-6% v/v. According to other embodiments, the ACD Formula A in the pharmaceutical composition is present at a concentration of 0.05%-5% v/v. According to other embodiments, the ACD Formula A in the pharmaceutical composition is present at a concentration of 0.01%-10% v/v.

According to some embodiments, the present invention provides a method of preventing or ameliorating GVHD in a subject undergoing HSCT, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells, wherein the preparation comprises no more than 15% polymorphonuclear leukocytes, and wherein the preparation comprises methylprednisolone at a concentration that does not exceed 30 µg/ml. According to some embodiments, the present invention provides a method of preventing or ameliorating GVHD in a subject undergoing HSCT, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells, and wherein the preparation comprises methylprednisolone at a concentration that does not exceed 30 µg/ml.

According to some embodiments, the present invention provides a method of preventing or ameliorating GVHD in a subject undergoing HSCT, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes, wherein the composition comprises an anti-coagulant selected from the group consisting of: heparin, ACD Formula A and a combination thereof, and wherein the composition comprises methylprednisolone at a concentration that does not exceed 30 Each possibility represents a separate embodiment of the present invention. According to some embodiments, the present invention provides a method of preventing or ameliorating GVHD in a subject undergoing HSCT, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells, wherein the composition comprises an anti-coagulant selected from the group consisting of: heparin, ACD Formula A and a combination thereof, and wherein the composition comprises methylprednisolone at a concentration that does not exceed 30 µg/ml. Each possibility represents a separate embodiment of the present invention.

According to some embodiments, the present invention provides a method of preventing or ameliorating GVHD in a subject undergoing HSCT, comprising administering to the subject a pharmaceutical composition comprising the cell preparation of the invention. According to some embodiments, the present invention provides a method of preventing or ameliorating GVHD in a subject undergoing HSCT, comprising administering to the subject the pharmaceutical composition of the invention.

According to some embodiments, the present invention provides the pharmaceutical composition of the invention for use in preventing or ameliorating GVHD in a subject undergoing HSCT. According to some embodiments, the pharmaceutical composition of the invention further comprises residual methylprednisolone. According to some embodiments, the pharmaceutical composition of the invention further comprises methylprednisolone at a concentration that does not exceed 30 µg/ml. According to some embodiments, the pharmaceutical composition of the invention further comprises an anti-coagulant. According to some embodiments, the anti-coagulant is selected from the group consisting of: heparin, ACD Formula A and a combination thereof. Each possibility represents a separate embodiment of the present invention.

According to some embodiments, the GVHD is high grade GVHD. According to specific embodiments, high grade GVHD is grade II-IV GVHD. According to another specific embodiment, high grade GVHD is grade III-IV GVHD. According to a particular embodiment, the pharmaceutical composition of the invention induces a shift from high grade GVHD to grade I GVHD.

According to another embodiment, the GVHD is acute GVHD. According to yet another embodiment, the GVHD is chronic GVHD. According to another particular embodiment, a subject administered with the pharmaceutical composition of the invention retains a graft-versus-tumor (GVTS) or graft-versus-leukemia (GVL) effect. Each possibility represents a separate embodiment of the present invention.

According to some embodiments, the GVHD is GVHD in the liver of the subject. Liver dysfunction in allogeneic HSCT recipients may be due to a variety of factors including toxicity from the preparative regimen and other medications, infection, veno-occlusive disease (VOD), and acute and chronic graft-versus-host disease (GVHD) of the liver.

According to another embodiment, the pharmaceutical composition of the invention reduces hepatotoxicity associated with GVHD. According to some embodiments, the cell preparation of the invention reduces hepatotoxicity associated with GVHD. Common symptoms and complications of Hepatotoxicity include lymphadenitis, fever, red blood cell sedimentation rate increased high bilirubin levels and febrile neutropenia.

According to some embodiments, the present invention provides a method of preventing or ameliorating an immune disease or an autoimmune disease or an inflammatory disease in a subject in need thereof, comprising administering to the subject a pharmaceutical composition comprising the cell preparation of the invention. Each possibility represents a separate embodiment of the present invention. According to some embodiments, the present invention provides a method of preventing or ameliorating an immune disease or an autoimmune disease or an inflammatory disease in a subject in need thereof, comprising administering to the subject the pharmaceutical composition of the invention. Each possibility represents a separate embodiment of the present invention.

According to some embodiments, the present invention provides the cell preparation of the invention for use in preventing or ameliorating an immune disease or an autoimmune disease or an inflammatory disease in a subject in need thereof. Each possibility represents a separate embodiment of the present invention. According to some embodiments, the present invention provides the pharmaceutical composition of the invention for use in preventing or ameliorating an immune disease or an autoimmune disease or an inflammatory disease in a subject in need thereof. Each possibility represents a separate embodiment of the present invention.

According to some embodiments, the immune disease is GVHD. According to some embodiments, the present invention provides the pharmaceutical composition of the invention for use in preventing or ameliorating GVHD in a subject in need thereof.

According to some embodiments, the present invention provides a method of preventing or ameliorating a hematopoietic malignancy comprising administering to a subject in need thereof the pharmaceutical composition of the invention. Each possibility represents a separate embodiment of the present invention. According to particular embodiments, the subject is suffering from a hematopoietic malignancy.

The term "hematopoietic malignancy" as used herein refers to any blood cell cancer, characterized by uncontrolled, abnormal growth of blood cells. The term "hematopoietic malignancy" includes but is not limited to leukemia, myelodysplastic syndrome, lymphoma, and multiple myeloma (plasma cell dyscrasia). The term "leukemia" refers to a disease of the blood forming organs characterized by an abnormal increase in the number of leucocytes in the tissues of the body with or without a corresponding increase of those in the circulating blood (e.g., acute lymphoblastic leukemia, ALL; acute myelogenous leukemia, AML; chronic myelogenous leukemia, CML; etc.). The term "myelodysplastic syndrome" refers to a condition in which the bone marrow shows qualitative and quantitative changes suggestive of a preleukemic process, but having a chronic course that does not necessarily terminate as acute leukemia. The term "lymphoma" refers to a malignant tumor of lymphoblasts derived from B or T lymphocytes (e.g., Hodgkin lymphoma, HL; non-Hodgkin lymphoma, NHL; etc.). The term "plasma cell dyscrasia" refers to plasmacytosis due to plasma cell proliferation (e.g., multiple myeloma, MM; plasma cell leukemia, PCL; etc.)

According to exemplary embodiments, said hematopoietic malignancy is selected from the group consisting of MDS, acute lymphoblastic leukemia (ALL), acute myeloid leukemia (AML) and chronic myelogenous leukemia (CML).

Infusion of certain types of the donor blood cells such as T-lymphocytes can also stimulate a graft-versus-leukemia effect. This effect has been best observed in patients with chronic myeloid leukemia (CML). In CML, 75 percent of patients relapsing after transplant re-enter remission. For other disorders such as acute myeloid leukemia (AML) and myelodysplastic syndrome (MDS), the effect is less pronounced; AML and MDS in approximately 20 percent of patients enter remission. For patients with acute lymphoblastic leukemia (ALL), the presence of graft-vs-leukemia effect is unclear, although small numbers of patients have reportedly benefited, at least transiently, from the effect.

In other ways, the donor immune cells may recognize residual leukemia, lymphoma or cancer cells as being different and destroy them. Retrospective studies have demonstrated that patients in whom acute or chronic GVHD develops have lower disease recurrence rates than patients who do not develop GVHD. This finding is an indirect indication of a graft-versus-tumor effect.

The term "conditioning treatment" refers to preparative treatment of transplant recipient with various conditioning regimens including radiation, immune sera, chemotherapy, and/or immunosuppressive agents, prior to transplantation. Transplantation conditioning is very common before bone marrow transplantation.

As used herein, the terms "subject", "patient" and "subject in need thereof" may be used interchangeably and refer to a subject in need of administration of the pharmaceutical composition of the invention.

According to some embodiments, the pharmaceutical composition of the invention is administered to a subject who has undergone or will undergo HSCT. Each possibility represents a separate embodiment of the present invention. According to some embodiments, a subject in need thereof is a subject undergoing HSCT. According to some embodiments, the Hematopoietic Stem Cells (HSCs) transplanted into a subject in need thereof and the cells of the pharmaceutical composition of the invention are derived from the same donor.

According to another embodiment, administering of the pharmaceutical composition of the invention is carried out up to 24 hours prior to the HSCT. According to some embodiments, administering of the pharmaceutical composition of the invention is carried out about 24-30 hours prior to the HSCT. According to yet another embodiment, the administering of the pharmaceutical composition of the invention is carried out at the same time as the HSCT. According to some embodiments, the administering of the pharmaceutical composition of the invention is carried out up to 15 days following the HSCT. According to additional embodiments, the HSCs used in the HSCT are allogeneic HSCs. According to non-limiting examples, the HSCs used in the HSCT may be derived from bone marrow, peripheral blood, or umbilical cord blood. Each possibility represents a separate embodiment of the present invention. According to another embodiment, the pharmaceutical composition of the invention is administered in a single dose.

Inflammatory Bowel Diseases

Inflammatory bowel diseases (IBD) are characterized by chronic intestinal inflammation with dysregulation of the mucosal immune system in the gastrointestinal tract manifested as Crohn's disease and ulcerative colitis. As used herein, the term IBD refers to Crohn's disease, ulcerative colitis or a combination thereof. Each possibility represents a separate embodiment of the present invention. Genetic factors and environmental factors that include both intestinal microflora and danger signals such as dextran sodium sulfate (DSS) were all shown to induce intestinal inflammation. TNFα and IFNγ blockade and anti-IL-1β strategies, as well as antibiotic treatment were able to ameliorate colitis induction, suggesting a role for nuclear factor-kappa B (NF-κB) and inflammasome inhibition of macrophages and dendritic cells in the lamina propria.

The therapeutic effect of the cell preparation and pharmaceutical composition of the invention disclosed herein was further demonstrated in inflammatory bowel disease (IBD). As exemplified herein below, a single infusion of the pharmaceutical composition of the invention significantly ameliorated both the clinical score and histological appearance of two different models of IBD: adoptive T cell transfer (TCT) of naïve CD4 cells and dextran sulfate sodium (DSS)-induced colitis.

The dextran sulfate sodium (DSS) model is generally viewed as an epithelial damage model suited to investigate wound-healing processes and innate immune responses. It has been suggested that DSS uptake by lamina propria macrophages initiates an inflammatory process. Macrophages primed with LPS and subsequently exposed to DSS secrete high levels of IL-1β and IL-18 in an NLRP3-, ASC-, and caspase-1-dependent manner. This effect was completely abrogated when the endocytosis of DSS was experimentally blocked.

Caspases are cysteine proteases first shown to be involved in the induction and execution of programmed cell death, and later in inflammation, leading to their categorization as proapoptotic or proinflammatory. Caspase-1 is one of three proinflammatory caspases that have been well studied and characterized. Its catalytic activity is regulated by autoactivation within multiprotein complexes called "inflammasomes" that mediate caspase-1-dependent processing of cytokines, most notably IL-1β. Proinflammatory stimuli induce expression of the IL-1β preform, but cytokine maturation and release are controlled by the inflammasome.

A number of node-like receptors (NLR) family members have been reported, but their physiological functions in vivo have been elucidated in only a few cases. NLRP1, NLRP3, and IPAF are danger sentinels that self-oligomerize via homotypic NACHT domain interactions to form high molecular weight complexes that induce caspase-1 autoactivation. NLRP3 inflammasome consists of the NLRP3 scaffold, the ASC (PYCARD) adaptor, and caspase-1. As part of immune defense, NLRP3 is activated upon exposure to whole pathogens such as the fungi *Candida albicans* and *Saccharomyces cerevisiae*, pore-forming toxins, and viruses, as well as diverse microbial components. Interestingly, NLRP3 is also activated by host-derived molecules leading to inflammatory disorders and perhaps autoimmune diseases. Extracellular ATP and hyaloronan, released by injured cells, monosodium urate crystals, and fibrillar amyloid-b peptides, are some examples.

The present invention demonstrates, for the first time, that the apoptotic cell composition of the invention negatively regulates the NLRP3 inflammasome, both in vitro and in vivo, and is able to downregulate the pro-inflammatory response induced via NLRP3 inflammasome in hematopoietic cells.

The inflammasome triggering is a two-hit model requiring both Toll-Like-Receptor (TLR) and inflammasome triggering. Indeed, the apoptotic cells of the invention were shown to inhibit TLRs and the NF-κB pathway. TLR triggering is important for enhanced transcription of pro-IL-1β and pro-IL-18, and is in fact needed for the DSS effect. It is now demonstrated herein that the apoptotic cell preparation of the invention inhibited the secretion of activated IL-1β at both pre- and post-transcription levels and had distinct inhibition effects on NF-κB and NLRP3.

It is further demonstrated herein below, that the apoptotic cell composition of the invention affects all three molecular mechanisms described in the regulation of inflammasome activation. Apoptotic cells, as comprised in the composition of the invention, were shown to be capable of reducing and inhibiting the formation of ROS, at rates similar to those shown for the chemical inhibitor NAC. It is well established that macrophages make use of toxic ROS to control microbial pathogens as part of the innate immune response and ROS were identified as major mediators of inflammatory signals believed to play a role in the development of IBD. Furthermore, generation of ROS was found to induce IL-1β via ERK phosphorylation. On the other hand, IL-1β signals may induce ROS generation. While it has been shown that DSS induces formation of ROS, a marked reduction in ROS generation, and consequently less IL-1β secretion, was observed when macrophages were pretreated with apoptotic cells as comprised in the preparation of the invention.

The second mechanism involves the lysosome. It was shown that lysosomal damage or leakage may serve as an endogenous danger signal and is sensed by the NLRP3 inflammasome. The involvement of the lysosome vacuole was analyzed since apoptotic cell clearances are mediated via the phagolysosomal pathway. As exemplified herein, lysosomes from peritoneal macrophages that had engulfed apoptotic cells were more stable to DSS challenge, and were not affected or damaged. This may point to the notion that engulfed apoptotic cells desensitize lysosome for at least 24 h after apoptotic ingestion. Taken together, these results demonstrate a mechanism of inflammasome inhibition and resolution of inflammation stemming from apoptotic cell clearance.

Inflammasomes were also suggested to be activated in response to signaling pathways that deplete intracellular potassium, such as the potassium ionophore nigericin. When macrophages were pretreated with apoptotic cells, nigericin-induced IL-1β secretion was significantly inhibited. The means by which apoptotic cells inhibit nigericin-induced IL-1β secretion in not clear, but supporting evidence might illustrate a direct inflammasome upstream inhibitory mechanism that is perhaps best mediated via NF-κB signaling. This observation illustrates a mechanism of regulation of inflammation that could take place in both infectious and non-infectious inflammatory conditions. Failure to clear apoptotic cells will trigger persistence inflammasome-dependent inflammation as perhaps is seen in failure to clear intracellular organelles.

In summary, infusion of the cell preparation of the invention is beneficial in mice models of IBD and inhibits both inflammasome- and NF-κB-dependent inflammation via three mechanisms.

According to some embodiments, the present invention provides a method of preventing or ameliorating IBD in a subject in need thereof, comprising administering to the subject the pharmaceutical composition of the invention. According to some embodiments, the present invention provides the pharmaceutical composition of the invention for use in preventing or ameliorating IBD in a subject in need thereof. Each possibility represents a separate embodiment of the present invention.

According to some embodiments, the present invention provides a method of preventing or ameliorating IBD in a subject in need thereof, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes; and wherein the pharmaceutical composition comprises an anti-coagulant selected from the group consisting of: heparin, ACD Formula A and a combination thereof. Each possibility represents a separate embodiment of the present invention.

According to some embodiments, the present invention provides a method of preventing or ameliorating IBD in a subject in need thereof, comprising administering to the subject a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes, wherein the composition comprises an anti-coagulant selected from the group consisting of: heparin, ACD Formula A and a combination thereof, and wherein the preparation comprises methylprednisolone at a concentration that does not exceed 30 Each possibility represents a separate embodiment of the present invention.

Apoptotic Cell Preparations

According to some embodiments, the preparation of the invention refers to a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes. According to certain embodiments, the preparation of the invention refers to a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% $CD15^{high}$ expressing cells. As used herein, the terms "the preparation", "the preparation of the invention", "the apoptotic cell preparation of the invention", "the cell preparation of the invention", "the cell preparation" and "the mononuclear enriched preparation" are used interchangeably.

According to some embodiments, the present invention provides a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes.

As used herein, the terms "the composition of the invention", "the pharmaceutical composition of the invention", "the pharmaceutical composition", "the composition", "apoptotic cell composition" and "composition comprising the cell preparation of the invention" are used interchangeably and refer to a composition comprising the cell preparation of the invention. According to some embodiments, the pharmaceutical composition of the invention refers to a composition comprising the cell preparation of the invention and further comprising an anticoagulant. According to some embodiments, the term "the composition of the invention" refers to a composition comprising the cell preparation of the invention and a final suspension medium used for administration of the cell preparation to a patient. According to some embodiments, the terms "final suspension medium" and "administration medium", as used herein, are used interchangeably and refer to the medium used for administration of the cell preparation of the invention to a subject. According to some embodiments, a pharmaceutical composition comprising the cell-preparation of the invention is referred to herein as "ApoCell". According to some embodiments, the pharmaceutical composition of the invention is referred to herein as "ApoCell".

In some embodiments, the mononuclear enriched cell preparation of the invention comprises at least 85% mononuclear cells, at least 85% mononuclear cells, alternatively at least 90% mononuclear cells or at least 95% mononuclear cells, wherein each possibility is a separate embodiment of the invention. According to some embodiments, the mononuclear enriched cell preparation of the invention comprises at least 80% mononuclear cells. According to some embodiments, the mononuclear enriched cell preparation of the invention comprises at least 90% mononuclear cells. According to some embodiments, the mononuclear enriched cell preparation of the invention comprises at least 95% mononuclear cells. According to some embodiments, the cell preparation of the invention comprises at least one cell type selected from the group consisting of: lymphocytes, monocytes and natural killer cells. According to some embodiments, mononuclear cells comprise lymphocytes and monocytes. As used herein and in the claims, mononuclear cells are leukocytes having a one lobed nucleus.

According to some embodiments, at least 40% of the cell preparation of the invention are in an early apoptotic state. According to other embodiments, at least 40%, preferably around 50% of the cell preparation of the invention are in an early apoptotic state. Each possibility represents a separate embodiment of the present invention. According to some embodiments, between 40-65%, preferably between 55-60% of the cell preparation of the invention are in an early apoptotic state. Each possibility represents a separate embodiment of the present invention.

It should be appreciated that, according to some embodiments, the high percentage of mononuclear cells in the cell preparation disclosed herein is achieved following the multistep manufacturing protocol, as described herein below (including leukapheresis, early-apoptosis induction using cryopreservation and incubation with methylprednisolone and various washing steps).

According to some embodiments, the mononuclear-enriched cell preparation of the invention comprises low concentrations of non-mononuclear leukocytes such as, but not limited to, polymorphonuclear leukocytes and neutrophils. Preferably, said mononuclear enriched cell preparation is devoid of granulocytes.

According to some embodiments, granulocytes disintegrate during various steps of the production method of the invention. According to some embodiments, the composition of the invention comprises no more than 15%, alternatively no more than 10%, typically no more than 5% granulocytes. Each possibility represents a separate embodiment of the present invention. According to some embodiments, granulocytes disintegrate to a significant degree following the freezing and thawing steps of the production method of the invention. According to some embodiments, granulocytes disintegrate to a significant degree following the freezing and thawing steps of the production method of the invention, and are washed from the preparation of the invention during wash steps after the freezing and/or thawing steps. Each possibility represents a separate embodiment of the present invention. According to some embodiments, disintegrated granulocytes are washed from the cell preparation of the invention during various washing steps of the production method of the invention.

According to some embodiments, the composition of the invention comprises no more than 15%, possibly no more than 10%, typically no more than 5% polymorphonuclear leukocytes. Each possibility represents a separate embodiment of the present invention. According to some embodiments, the composition of the invention comprises no more than 5% polymorphonuclear leukocytes.

According to some embodiments, the composition of the invention comprises no more than 15%, alternatively no more than 10%, typically no more than 5% $CD15^{high}$ expressing cells. Each possibility represents a separate embodiment of the present invention. According to some embodiments, the composition of the invention comprises no more than 5% CD15$^{high}$ expressing cells. According to some embodiments, as exemplified herein below, the composition of the invention comprises no more than 1% CD15$^{high}$ expressing cells. As used herein and in the claims, CD15$^{high}$ expressing cells are granulocytes.

An early feature of apoptosis is a morphological change in the plasma membrane. This change involves the translocation of the membrane phospholipid phosphatidylserine (PS) from the internal layer to the external layer of the cell membrane. In the presence of calcium ions, Annexin V has a high specificity and affinity for PS. Thus, the binding of Annexin V to cells with exposed PS provides a very sensitive method for detecting early cellular apoptosis. Thus, an "early apoptotic state" of a cell or "early apoptotic cells", as used herein, refers to a cell population which still have intact cell membranes, but have started to undergo DNA cleavage and have started to undergo translocation of phosphatidylserine. As used herein, early apoptotic cells, or cells at an early apoptotic state, are cells which are stained positively using Annexin V and are stained negatively with propidium iodide (PI). Methods for detection of early apoptosis are known in the art, such as early apoptotic cell detection of annexin V positive and propidium iodide (PI) negative, by flow cytometry. According to some embodiments, cells which are in a late apoptotic state may be detected by a positive staining using annexin V and a positive staining using PI as may be evidenced using flow cytometry. It is to be noted that PI is membrane impermeable and thus is only able to enter cells in which the intactness of the cell membrane has been compromised, such as in late apoptotic or necrotic cells. According to some embodiments, necrotic cells show strong staining for PI, as may be evidenced using flow cytometry.

According to some embodiments, at least 40% of the cells in the cell preparation of the invention are in an early-apoptotic state. According to other embodiments, at least 50% or alternatively at least 60% of the cells in the cell preparation of the invention are in an early-apoptotic state. Each possibility represents a separate embodiment of the present invention. In some embodiments, the cell preparation of the invention comprises cells in suspension. In another embodiment, the cell preparation of the invention is not prepared by inducing cells to adhere to a surface.

As used herein, "viability" of the cells refers to cells not undergoing necrosis or late apoptosis. Accordingly, the term "viable cells", as used herein, refers to cells not undergoing necrosis or cells which are not in a late apoptotic state. According to some embodiments, the term "viable cells" refers to cells having an intact plasma membrane. Assays for determining cell viability are known in the art, such as using propidium iodide (PI) staining which may be detected by flow cytometry. Accordingly, according to some embodiments, viable cells are cells which do not show propidium iodide intake. Necrosis can be further identified, by using light, fluorescence or electron microscopy techniques, or via uptake of the dye trypan blue.

Apoptosis, which is a distinct cell death process from necrosis, is the programmed and orderly physiological elimination of cells, occurring, for example, during normal cell and tissue development, T-lymphocyte killing of pathogen-infected cells, and self-elimination of mutationally damaged cells. Apoptotic cells are characterized by distinct morphologic alterations in the cytoplasm and nucleus, chromatin cleavage at regularly spaced sites, and endonucleolytic cleavage of genomic DNA at internucleosomal sites. Assays for determining cell apoptosis are known in the art, such as using AnnexinV. Necrosis, on the other hand, is an inherently pathological and pro-inflammatory process of cell death caused, typically but not exclusively, by the uncontrolled, progressive degradative action of enzymes following lethal cellular injury. Necrotic cells are typically characterized by mitochondrial swelling, nuclear flocculation, cell lysis, loss of membrane integrity, and ultimately cell death.

According to some embodiments, the cell preparation of the invention comprises at least 85%, 90% 95% viable cells, alternatively at least 97% viable cells. Each possibility represents a separate embodiment of the present invention. In another embodiments, the cell preparation of the invention comprises at-most 15%, 10%, 5% necrotic cells or cells in a late apoptotic state, alternatively at most 3% necrotic cells or cells in a late apoptotic state. Each possibility represents a separate embodiment of the present invention. In additional embodiments, the high percentage of viable cells in the cell preparation of the invention remains for at least 24 hours following preparation. According to some embodiments, necrotic cells and/or cells in a late apoptotic state disintegrate and are thus substantially eliminated from the final cell-preparation of the invention during washing steps of the production method of the invention. Each possibility represents a separate embodiment of the present invention.

According to some embodiments of the present invention, in order to induce therapeutic immune tolerance in autoimmune diseases, such as GVHD, the therapeutic mononuclear enriched cells in the cell preparation of the invention are preferably derived from an allogeneic individual. Allogeneic mononuclear enriched cells are preferably haplotype-matched with the subject receiving said cells. Haplotype-matching of human subjects is routinely practiced in the art in the context of therapeutic transplantation, and usually involves matching of HLA-A, HLA-B, and HLA-DR alleles. In some embodiments, the source of the mononuclear enriched cell preparation is derived from an allogeneic donor that is HLA-matched at least a 7/8 at the HLA A, B, C, and DR loci. In some embodiments, the source of the mononuclear enriched cell preparation is autologous.

According to some embodiments, the pharmaceutical composition of the invention comprises the cell preparation of the invention and further comprises an anti-coagulant. According to some embodiments, the pharmaceutical composition of the invention comprises the cell preparation of the invention and further comprises residual methylprednisolone. According to other embodiments, the pharmaceutical composition of the invention comprises the cell preparation of the invention and further comprises an anti-coagulant and residual methylprednisolone. According to some embodiments, residual methylprednisolone refers to methylprednisolone remaining in the composition of the invention following use of the production method of the invention.

According to some embodiments, the composition of the invention comprises an anti-coagulant. As known in the art, an anti-coagulant, as used herein, refers to a substance which prevents or decreases blood clotting. According to some embodiments, the anti-coagulant is heparin. According to other embodiments, the anti-coagulant is Acid-Citrate-Dextrose (ACD), formula A. According to some embodiments, the anti-coagulant is a composition comprising ACD formula A and heparin. According to some embodiments, the anti-coagulant is ACD formula A containing heparin at a concentration of about 10 U/ml. According to some embodiments, the anti-coagulant is selected from the group consisting of: heparin, ACD Formula A and a combination thereof. Each possibility represents a separate embodiment of the present invention. According to some embodiments, the presence of an anti-coagulant in the composition of the invention is due to addition of the anti-coagulant during the freezing and/or incubation and/or washing stages of the composition's production process. Each possibility represents a separate embodiment of the present invention. According to some embodiments, the presence of an anti-coagulant during production of the composition of the invention does not adversely affect apoptosis induction as described herein.

According to some embodiments, the composition of the invention comprises heparin. According to some embodiments, heparin is selected from the group consisting of: sulfated heteropolysaccharide heparin, unfractionated heparin (UFH), low molecular weight heparin (LMWH) and a combination thereof. Each possibility represents a separate embodiment of the present invention. According to other embodiments, heparin is a synthetic heparin, such as, but not limited to, Fondaparinaux.

According to some embodiments, the composition of the invention comprises heparin at a concentration between 0.001 U/ml and 3 U/ml, alternatively between 0.005 U/ml and 2.5 U/ml, typically between 0.01 U/ml and 1 U/ml. Each possibility represents a separate embodiment of the present invention. According to other embodiments, the composition of the invention comprises heparin at a concentration between 0.001-2.5 U/ml, alternatively between 0.001-1 U/ml, possibly between 0.001-0.5 U/ml. Each possibility represents a separate embodiment of the present invention.

According to other embodiments, the composition of the invention comprises heparin at a concentration between 0.005-1 U/ml, alternatively between 0.005-0.6 U/ml, possibly between 0.005-0.5 U/ml. Each possibility represents a separate embodiment of the present invention. According to other embodiments, the composition of the invention comprises heparin at a concentration between 0.01-3 U/ml, alternatively between 0.01-2 U/ml or between 0.01-0.6 U/ml. Each possibility represents a separate embodiment of the present invention. According to some embodiments, the composition of the invention comprises heparin at a concentration between 0.01-0.5 U/ml. According to some embodiments, the composition of the invention comprises heparin at a concentration between 0.05 U/ml and 0.25 U/ml. According to certain embodiments, the composition of the invention comprises heparin at a concentration between 0.01 U/ml and 0.6 U/ml.

According to some embodiments, the composition of the invention comprises up to 3 U/ml heparin, typically up to 2.5 U/ml heparin, possibly up to 1 U/ml heparin, alternatively up to 0.5 U/ml heparin. According to some embodiments, the composition of the invention comprises at least 0.001 U/ml heparin, alternatively at least 0.005 U/ml heparin, possibly at least 0.01 heparin. Each possibility represents a separate embodiment of the present invention. According to some embodiments, the composition of the invention comprises up to 300 U, alternatively up to 150 U, possibly up to 75 U of Heparin. Each possibility represents a separate embodiment of the present invention. According to certain embodiments, the composition of the invention comprises up to 180 U of heparin.

According to some embodiments, heparin comprised in the composition of the invention refers to heparin in the composition comprising the cell preparation of the invention and the final suspension medium used for administration of the cell preparation to a patient. According to some embodiments, ACD Formula A comprised in the composition of the invention refers to heparin in the composition comprising the cell preparation of the invention and the final suspension medium used for administration of the cell preparation to a patient.

According to some embodiments, the composition of the invention comprises between 0.5-500 U of heparin, possibly between 0.5-500 U of heparin, alternatively between 7-180 U of heparin. Each possibility represents a separate embodiment of the present invention.

According to some embodiments, the composition of the invention comprises ACD Formula A. According to some embodiments, ACD Formula A comprises citric acid, dextrose and sodium citrate. According to some embodiments, ACD Formula A comprises anhydrous citric acid at a concentration of 0.73 gr/100 ml, dextrose monohydrate at a concentration of 2.45 gr/100 ml and sodium citrate dehydrate at a concentration of 2.20 gr/100 ml.

According to some embodiments, the composition of the invention comprises ACD formula A at a concentration between 0.01%-10% v/v, alternatively between 0.05%-6% v/v, possibly between 0.1%-5% v/v. Each possibility represents a separate embodiment of the present invention. According to other embodiments, the composition of the invention comprises ACD formula A at a concentration between 0.05%-10% v/v, possibly 0.05%-6% v/v, alternatively between 0.05%-5% v/v. Each possibility represents a separate embodiment of the present invention.

According to alternate embodiments, the composition of the invention comprises ACD formula A at a concentration between 0.1%-10% v/v, alternatively between 0.1%-6%, possibly between 0.1%-5% v/v. Each possibility represents a separate embodiment of the present invention. According to some embodiments, the composition of the invention comprises ACD formula A at a concentration between 0.5%-2.5% v/v. According to certain embodiments, the composition of the invention comprises ACD formula A at a concentration between 0.05%-6% v/v, typically between 0.1%-6% v/v. Each possibility represents a separate embodiment of the present invention.

According to some embodiments, the composition of the invention comprises up to 15 ml, alternatively up to 9 ml, possibly up to 7.5 ml of ACD formula A. Each possibility represents a separate embodiment of the present invention. According to certain embodiments, the composition of the invention comprises up to 18 ml of ACD formula A.

According to some embodiments, the composition of the invention comprises between 0.05-40 ml of ACD formula A, possibly between 0.1-25 ml of ACD formula A, alternatively between 0.7-18 ml of ACD formula A. Each possibility represents a separate embodiment of the present invention.

According to some embodiments, the composition of the invention further comprises methylprednisolone. According to some embodiments, the presence of residual methylprednisolone in the composition of the invention is due to use of methylprednisolone during the incubation stage of the cell preparation's production process. According to some embodiments, methylprednisolone is used in the present invention during production of the cell preparation of the invention, as part of the procedure in which the cells are induced to enter an early-apoptotic state.

According to some embodiments, the composition of the invention further comprises methylprednisolone at a concentration between 0.5-30 µg/ml, possibly 1-25 µg/ml, typically between 3-22 µg/ml. Each possibility represents a separate embodiment of the present invention. According to some embodiments, the composition of the invention comprises methylprednisolone at a concentration between 3.7-21.9 µg/ml.

According to some embodiments, the composition of the invention further comprises methylprednisolone at a concentration that does not exceed 30 µg/ml. According to some embodiments, the composition of the invention further comprises methylprednisolone at a concentration that does not exceed 30 µg/ml, possibly does not exceed 25 µg/ml, typically does not exceed 21.9 µg/ml. Each possibility represents a separate embodiment of the present invention.

According to some embodiments, the composition of the invention further comprises methylprednisolone at a concentration between 0.5-60 µg/ml, possibly 1.12-60 µg/ml. Each possibility represents a separate embodiment of the present invention. According to some embodiments, the composition of the invention further comprises methylprednisolone at a concentration that does not exceed 60 µg/ml.

According to some embodiments, the composition of the invention comprises at least 0.5 µg/ml, possibly at least 1 µg/ml, alternatively at least 3 µg/ml methylprednisolone. Each possibility represents a separate embodiment of the present invention. According to some embodiments, the composition of the invention comprises at least 3.5 µg/ml methylprednisolone. According to some embodiments, the composition of the invention comprises at least 3.7 µm/ml methylprednisolone.

According to some embodiments, the composition of the invention further comprises between 0.1-25 mg methylprednisolone, possibly between 0.4-20 mg methylprednisolone, alternatively between 0.67-18 mg methylprednisolone. Each possibility represents a separate embodiment of the present invention. According to some embodiments, the composition of the invention further comprises methylprednisolone in an amount that does not exceed 25 mg, typically 20 mg, alternatively 18 mg. Each possibility represents a separate embodiment of the present invention. According to certain embodiments, the composition of the invention further comprises methylprednisolone in an amount that does not exceed 15 mg.

According to some embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes. According to certain embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state and wherein at least 85% of the cells in the preparation are viable cells.

According to some embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the pharmaceutical composition comprises an anti-coagulant. According to some embodiments, the anti-coagulant is selected from the group consisting of: heparin, ACD Formula A and a combination thereof. Each possibility represents a separate embodiment of the present invention.

According to some embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells, wherein the preparation comprises no more than 15% polymorphonuclear leukocytes and wherein the pharmaceutical composition comprises an anti-coagulant. According to some embodiments, the anti-coagulant is selected from the group consisting of: heparin, ACD Formula A and a combination thereof. Each possibility represents a separate embodiment of the present invention.

According to some embodiments, the heparin in the pharmaceutical composition is present at a concentration between 0.005 U/ml and 2.5 U/ml. According to other embodiments, the ACD Formula A in the pharmaceutical composition is present at a concentration of 0.01%-10% v/v, alternatively 0.05%-5% v/v. Each possibility represents a separate embodiment of the present invention.

According to some embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells, wherein the preparation comprises no more than 15% polymorphonuclear leukocytes and wherein the preparation comprises methylprednisolone at a concentration which does not exceed 30 µg/ml. According to certain embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises methylprednisolone at a concentration which does not exceed 30 µg/ml.

According to some embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells, wherein the preparation comprises no more than 15% polymorphonuclear leukocytes and wherein the preparation comprises an anti-coagulant and methylprednisolone. According to some embodiment, the concentration of methylprednisolone in the pharmaceutical composition of the invention does not exceed 30 µg/ml. According to certain embodiments, the pharmaceutical composition of the invention comprises a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises an anti-coagulant and methylprednisolone. According to some embodiment, the concentration of methylprednisolone in the pharmaceutical composition of the invention does not exceed 30 µg/ml.

In particular embodiments, the pharmaceutical composition of the invention is administered at a dosage of about $30 \times 10^6$-$300 \times 10^6$ cells per kg body weight, $100 \times 10^6$-$300 \times 10^6$ cells per kg body weight, alternatively about $120 \times 10^6$-$250 \times 10^6$ cells per kg body weight. Each possibility represents a separate embodiment of the present invention. In particular embodiments, the pharmaceutical composition of the invention is administered at a dosage of about $35 \times 10^6$ cells per kg body weight. According to some embodiments, the pharmaceutical composition of the invention is administered at a dosage of about $140 \times 10^6$-$210 \times 10^6$ cells per kg body weight. According to a particular embodiment, the pharmaceutical composition of the invention is administered at a dosage of about $140 \times 10^6$ cells per kg body weight. According to another particular embodiment, the pharmaceutical composition of the invention is administered at a dosage of about $210 \times 10^6$ cells per kg body weight. According to another particular embodiment, the pharmaceutical composition of the invention is administered at a dosage of about $35 \times 10^6$-$210 \times 10^6$ cells per kg body weight. According to another particular embodiment, the pharmaceutical composition of the invention is administered at a dosage of about $250 \times 10^6$ cells per kg body weight. In other embodiments, the pharmaceutical composition of the invention is administered at a dosage of about $5 \times 10^6$ cells per kg body weight. It should be appreciated that said low dosage is suitable for local injection of the compositions disclosed herein, such as local injection to a joint for treating arthritis.

According to some embodiments, the therapeutic mononuclear-enriched cell preparation of the invention is administered to the subject systemically, preferably via the intravenous route. Each possibility represents a separate embodiment of the present invention. Alternately, the therapeutic mononuclear enriched cell may be administered to the subject according to various other routes, including, but not limited to, the parenteral, intraperitoneal, intra-articular, intramuscular and subcutaneous routes. Each possibility represents a separate embodiment of the present invention. Preferably, the therapeutic mononuclear enriched cells are administered to the subject suspended in a suitable physiological buffer, such as, but not limited to, saline solution, PBS, HBSS, and the like. In addition the suspension medium may further comprise supplements conducive to maintaining the viability of the cells.

Methods of Producing Apoptotic Cell Preparations

According to another aspect, the present invention provides a method for producing the pharmaceutical composition of the invention (referred to herein as "the production method of the invention"), wherein the method comprises: obtaining a mononuclear-enriched cell composition from the peripheral blood of a donor, the mononuclear-enriched cell composition comprising at least 65% mononuclear cells;
freezing the mononuclear-enriched cell composition in a freezing medium;
thawing the mononuclear-enriched cell composition;
incubating the mononuclear-enriched cell composition in an incubation medium comprising methylprednisolone at a final concentration of about 10-100 μg/mL;
wherein at least one of the freezing medium and the incubation medium comprise an anti-coagulant; and
suspending said cell composition in an administration medium, thereby providing the pharmaceutical composition of the invention. Each possibility represents a separate embodiment of the present invention.

According to some embodiments, the pharmaceutical composition obtained according to the production method of the invention comprises at least 85% mononuclear cells. In further embodiments, the pharmaceutical composition contains at least 85% mononuclear cells, 90% mononuclear cells or alternatively over 90% mononuclear cells. Each possibility is a separate embodiment of the invention. According to some embodiments, the pharmaceutical composition comprises at least 90% mononuclear cells. According to some embodiments, the pharmaceutical composition comprises at least 95% mononuclear cells.

According to some embodiments, obtaining a mononuclear-enriched cell composition according to the production method of the invention is effected by leukapheresis. As used herein, the term "leukapheresis" refers to an apheresis procedure in which leukocytes are separated from the blood of a donor. According to some embodiments, the blood of a donor undergoes leukapheresis and thus a mononuclear-enriched cell composition is obtained according to the production method of the invention. It is to be noted, that the use of at least one anticoagulant during leukapheresis is required, as is known in the art, in order to prevent clotting of the collected cells.

According to some embodiments, the leukapheresis procedure is configured to allow collection of mononuclear-enriched cell composition according to the production method of the invention. According to some embodiments, cell collections obtained by leukapheresis comprise at least 65%, preferably at least 70%, most preferably at least 80% mononuclear cells. Each possibility represents a separate embodiment of the present invention. According to some embodiments, blood plasma from the cell-donor is collected in parallel to obtaining of the mononuclear-enriched cell composition according to the production method of the invention. According to some embodiments, about 300-600 ml of blood plasma from the cell-donor are collected in parallel to obtaining the mononuclear-enriched cell composition according to the production method of the invention. According to some embodiments, blood plasma collected in parallel to obtaining the mononuclear-enriched cell composition according to the production method of the invention is used as part of the freezing and/or incubation medium. Each possibility represents a separate embodiment of the present invention.

It is to be noted that, according to some embodiments, while the mononuclear-enriched cell preparation at cell collection comprises at least 65%, preferably at least 70%, most preferably at least 80% mononuclear cells, the final pharmaceutical composition of the invention, following the production method of the invention, comprises at least 85%, preferably at least 90%, most preferably at least 95% mononuclear cells. Each possibility represents a separate embodiment of the present invention.

According to certain embodiments, the mononuclear-enriched cell preparation used for production of the composition of the invention comprises at least 50% mononuclear cells at cell collection. According to certain embodiments, the present invention provides a method for producing the pharmaceutical composition of the invention wherein the method comprises obtaining a mononuclear-enriched cell preparation from the peripheral blood of a donor, the mononuclear-enriched cell preparation comprising at least 50% mononuclear cells. According to certain embodiments, the present invention provides a method for producing the pharmaceutical composition of the invention wherein the method comprises freezing a mononuclear-enriched cell preparation comprising at least 50% mononuclear cells.

According to some embodiments, the mononuclear-enriched cell composition obtained according to the production method of the invention undergoes freezing in a freezing medium. According to some embodiments, the freezing is gradual. According to some embodiments, following collection the cells are maintained at room temperature until frozen. According to some embodiments, the cell-preparation undergoes at least one washing step in washing medium following cell-collection and prior to freezing. As used herein, the terms "obtaining cells" and "cell collection" are used interchangeably. According to some embodiments, the cells of the cell preparation of the invention are frozen within 3-6 hours of collection. According to some embodiments, the cell preparation of the invention is frozen within up to 6 hours of cell collection. According to some embodiments, the cells of the cell preparation of the invention are frozen within 1, 2, 3, 4, 5, 6, 7, 8 hours of collection. Each possibility represents a separate embodiment of the present invention. According to other embodiments, the cells of the cell preparation of the invention are frozen up to 8, 12, 24, 48, 72 hours of collection. Each possibility represents a separate embodiment of the present invention. According to other embodiments, following collection the cells are maintained at 2-8° C. until frozen.

According to some embodiments, freezing according to the production method of the invention comprises: freezing the cell preparation at about −18° C. to −25° C. followed by freezing the cell preparation at about −80° C. and finally freezing the cell preparation in liquid nitrogen until thawing. According to some embodiments, the freezing according to the production method of the invention comprises: freezing the cell preparation at about −18° C. to −25° C. for at least 2 hours, freezing the cell preparation at about −80° C. for at least 2 hours and finally freezing the cell preparation in liquid nitrogen until thawing. According to some embodiments, the cells are kept in liquid nitrogen for at least 8, 10 or 12 hours prior to thawing. Each possibility represents a separate embodiment of the present invention. According to some embodiments, the cells of the cell preparation are kept in liquid nitrogen until thawing and incubation with apoptosis-inducing incubation medium. According to some embodiments, the cells of the cell preparation are kept in liquid nitrogen until the day of hematopoietic stem cell transplantation. According to non-limiting examples, the time from cell collection and freezing to preparation of the final composition of the invention may be between 1-50 days, alternatively between 6-30 days. Each possibility represents a separate embodiment of the present invention. According to alternative embodiments, the cell preparation may be kept in liquid nitrogen for longer time periods, such as at least several months.

According to some embodiments, the freezing according to the production method of the invention comprises freezing the cell preparation at about −18° C. to −25° C. for at least 0.5, 1, 2, 4 hours. Each possibility represents a separate embodiment of the present invention. According to some embodiments, the freezing according to the production method of the invention comprises freezing the cell preparation at about −18° C. to −25° C. for about 2 hours. According to some embodiments, the freezing according to the production method of the invention comprises freezing the cell preparation at about −80° C. for at least 0.5, 1, 2, 4, 12 hours. Each possibility represents a separate embodiment of the present invention.

According to some embodiments, the mononuclear-enriched cell composition may remain frozen at least 1, 2, 3, 4, 5, 6, 7, 8, 9, 10, 11, 12, 20 months. Each possibility represents a separate embodiment of the present invention. According to some embodiments, the mononuclear-enriched cell composition may remain frozen at least 0.5, 1, 2, 3, 4, 5 years. Each possibility represents a separate embodiment of the present invention. According to certain embodiments, the mononuclear-enriched cell composition may remain frozen for at least 20 months.

According to some embodiments, the mononuclear-enriched cell composition is frozen for at least 8, 10, 12, 18, 24 hours. Each possibility represents a separate embodiment of the present invention. According to certain embodiments, freezing the mononuclear-enriched cell composition is for a period of at least 8 hours. According to some embodiments, the mononuclear-enriched cell composition is frozen for at least about 10 hours. According to some embodiments, the mononuclear-enriched cell composition is frozen for at least about 12 hours. According to some embodiments, the mononuclear-enriched cell composition is frozen for about 12 hours. According to some embodiments, the total freezing time of the mononuclear-enriched cell composition (at about −18° C. to −25° C., at about −80° C. and in liquid nitrogen) is at least 8, 10, 12, 18, 24 hours. Each possibility represents a separate embodiment of the present invention.

According to some embodiments, the freezing at least partly induces the early-apoptotic state in the cells of the mononuclear-enriched cell composition. According to some embodiments, the freezing medium comprises RPMI 1640 medium comprising L-glutamine, Hepes, Hes, dimethyl sulfoxide (DMSO) and plasma. According to some embodiments, the plasma in the freezing medium is an autologous plasma of the donor which donated the mononuclear-enriched cells of the composition of the invention. According to some embodiments, the freezing medium comprises RPMI 1640 medium comprising 2 mM L-glutamine, 10 mM Hepes, 5% Hes, 10% dimethyl sulfoxide and 20% v/v plasma.

According to some embodiments, the freezing medium comprises an anti-coagulant. According to certain embodiments, at least some of the media used during the production method of the invention, including the freezing medium, the incubation medium and the washing media comprise an anti-coagulant. According to certain embodiments, all media used during the production method of the invention which comprise an anti-coagulant comprise the same concentration of anti-coagulant. According to some embodiments, anti-coagulant is not added to the final suspension medium of the cell composition of the invention.

According to some embodiments, addition of an anti-coagulant at least to the freezing medium improves the yield of the cell-preparation of the invention. According to other embodiments, addition of an anti-coagulant to the freezing medium improves the yield of the cell-preparation in the presence of a high triglyceride level. As used herein, improvement in the yield of the cell-preparation of the invention relates to improvement in at least one of: the percentage of viable cells out of cells frozen, the percentage of early-state apoptotic cells out of viable cells and a combination thereof. Each possibility represents a separate embodiment of the present invention.

According to some embodiments, cell yield in the composition of the invention relates to cell number in the composition out of the initial number of cells subjected to apoptosis induction according to the present invention. As used herein, the terms "induction of early apoptotic state" and "induction of apoptosis" are used interchangeably.

According to some embodiments, improvement in the yield of the cell-preparation of the invention relates to improvement in the number of the early-apoptotic viable cells of the preparation out of the number of frozen cells from which the preparation was produced.

According to some embodiments, addition of an anti-coagulant to the freezing medium contributes to a high and stable yield between different preparations of the pharmaceutical composition of the invention. According to preferable embodiments, addition of an anti-coagulant at least to the freezing medium and incubation medium results in a high and stable yield between different preparations of the pharmaceutical composition, regardless to the cell collection protocol used.

According to some embodiments, the freezing medium comprises an anti-coagulant selected from the group consisting of: heparin, ACD Formula A and a combination thereof. Each possibility represents a separate embodiment of the present invention. According to some embodiments, the anti-coagulant used in the freezing medium is ACD Formula A containing heparin at a concentration of 10 U/ml. According to some embodiments, the freezing medium comprises 5% v/v of ACD Formula A solution comprising heparin at a concentration of 10 U/ml.

According to some embodiments, the freezing medium comprises heparin. According to some embodiments, the heparin in the freezing medium is at a concentration of between 0.1-2.5 U/ml. According to some embodiments, the heparin in the freezing medium is at a concentration of between 0.1-2.5 U/ml, possibly between 0.3-0.7 U/ml, typically about 0.5 U/ml. Each possibility represents a separate embodiment of the present invention. According to certain embodiments, the heparin in the freezing medium is at a concentration of about 0.5 U/ml.

According to some embodiments, the freezing medium comprises ACD Formula A. According to some embodiments, the ACD Formula A in the freezing medium is at a concentration of between 1%-15% v/v. According to some embodiments, the ACD Formula A in the freezing medium is at a concentration of between 1%-15% v/v, possibly between 4%-7% v/v, typically about 5% v/v. Each possibility represents a separate embodiment of the present invention. According to some embodiments, the ACD Formula A in the freezing medium is at a concentration of about 5% v/v.

According to some embodiments, the mononuclear-enriched cell composition undergoes at least one washing step following cell collection and prior to being re-suspended in the freezing medium and frozen. According to some embodiments, the mononuclear-enriched cell composition undergoes at least one washing step following freezing and thawing. According to some embodiments, washing steps comprise centrifugation of the mononuclear-enriched cell composition followed by supernatant extraction and re-suspension in washing medium.

According to some embodiments, cell collection refers to obtaining a mononuclear-enriched cell composition. According to some embodiments, washing steps performed during the production method of the invention are performed in a washing medium. According to certain embodiments, washing steps performed up until the incubation step of the production method of the invention are performed in a washing medium. According to some embodiments, the washing medium comprises RPMI 1640 medium supplemented with L-glutamine and Hepes. According to some embodiments, the washing medium comprises RPMI 1640 medium supplemented with 2 mM L-glutamine and 10 mM Hepes.

According to some embodiments, the washing medium comprises an anti-coagulant. According to some embodiments, the washing medium comprises an anti-coagulant selected from the group consisting of: heparin, ACD Formula A and a combination thereof. Each possibility represents a separate embodiment of the present invention. According to some embodiments, the concentration of the anti-coagulant in the washing medium is the same concentration as in the freezing medium. According to some embodiments, the concentration of the anti-coagulant in the washing medium is the same concentration as in the incubation medium. According to some embodiments, the anti-coagulant used in the washing medium is ACD Formula A containing heparin at a concentration of 10 U/ml.

According to some embodiments, the washing medium comprises heparin. According to some embodiments, the heparin in the washing medium is at a concentration of between 0.1-2.5 U/ml. According to some embodiments, the heparin in the washing medium is at a concentration of between 0.1-2.5 U/ml, possibly between 0.3-0.7 U/ml, typically about 0.5 U/ml. Each possibility represents a separate embodiment of the present invention. According to certain embodiments, the heparin in the washing medium is at a concentration of about 0.5 U/ml.

According to some embodiments, the washing medium comprises ACD Formula A. According to some embodiments, the ACD Formula A in the washing medium is at a concentration of between 1%-15% v/v. According to some embodiments, the ACD Formula A in the washing medium is at a concentration of between 1%-15% v/v, possibly between 4%-7% v/v, typically about 5% v/v. Each possibility represents a separate embodiment of the present invention. According to some embodiments, the ACD Formula A in the washing medium is at a concentration of about 5% v/v.

According to some embodiments, the mononuclear-enriched cell composition is thawed several hours prior to the intended administration of the composition of the invention to a subject. According to some embodiments, the mononuclear-enriched cell composition is thawed at about 33° C.-39° C. According to some embodiments, the mononuclear-enriched cell composition is thawed for about 30-240 seconds, preferably 40-180 seconds, most preferably 50-120 seconds. Each possibility represents a separate embodiment of the present invention.

According to some embodiments, the mononuclear-enriched cell composition is thawed at least 10 hours prior to the intended administration of the composition of the invention, alternatively at least 20, 30, 40 or 50 hours prior to the intended administration of the composition of the invention. Each possibility represents a separate embodiment of the present invention. According to some embodiments, the mononuclear-enriched cell composition is thawed at least 15-24 hours prior to the intended administration of the composition of the invention. According to some embodiments, the mononuclear-enriched cell composition is thawed at least about 24 hours prior to the intended administration of the composition of the invention. According to some embodiments, the mononuclear-enriched cell composition is thawed at least 20 hours prior to the intended administration of the composition of the invention. According to some embodiments, the mononuclear-enriched cell composition is thawed 30 hours prior to the intended administration of the composition of the invention. According to some embodiments, the mononuclear-enriched cell composition is thawed at least 24 hours prior to the intended administration of the composition of the invention. According to some embodiments, the mononuclear-enriched cell composition undergoes at least one step of washing in the washing medium before and/or after thawing. Each possibility represents a separate embodiment of the present invention.

According to some embodiments, the mononuclear-enriched cell composition is incubated in incubation medium following freezing and thawing. According to some embodiments, there is at least one washing step between thawing and incubation. As used herein, the terms "incubation medium" and "apoptosis inducing incubation medium" are used interchangeably. According to some embodiments, the incubation medium comprises RPMI 1640 medium supplemented with L-glutamine, Hepes methylprednisolone and plasma. According to some embodiments, the washing medium comprises 2 mM L-glutamine, 10 mM Hepes and 10% v/v blood plasma. According to some embodiments, the blood plasma in the incubation medium is derived from the same donor from whom the cells of the cell preparation of the invention are derived. According to some embodiments, the blood plasma is added to the incubation medium on the day of incubation. According to some embodiments, incubation is performed at 37° C. and 5% $CO_2$.

According to some embodiments, the incubation medium comprises methylprednisolone. According to some embodiments, the methylprednisolone within the incubation medium further induces the cells in the mononuclear-enriched cell composition to enter an early-apoptotic state. According to some embodiments, the cells in the mononuclear-enriched cell composition are induced to enter an early-apoptotic state both by freezing and incubating in the presence of methylprednisolone. According to some embodiments, the production method of the invention advantageously allows induction of an early-apoptosis state substantially without induction of necrosis, wherein the cells remain stable at said early-apoptotic state for about 24 hours following preparation.

According to some embodiments, the incubation medium comprises methylprednisolone at a concentration of about 10-100 µg/ml. According to some embodiments, the incubation medium comprises methylprednisolone at a concentration of about 40-60 µg/ml, alternatively about 45-55 µg/ml. Each possibility represents a separate embodiment of the present invention. According to some embodiments, the incubation medium comprises methylprednisolone at a concentration of 50 µg/ml.

According to some embodiments, the incubation is for about 2-12 hours, possibly 4-8 hours, typically for about 5-7 hours. Each possibility represents a separate embodiment of the present invention. According to some embodiments, the incubation is for about 6 hours. According to some embodiments, the incubation is for at least 6 hours. According to a preferred embodiment, the incubation is for 6 hours.

According to some embodiments, the incubation medium comprises an anti-coagulant. According to some embodiments, addition of an anti-coagulant to the incubation medium improves the yield of the cell-preparation of the invention. According to some embodiments, the anti-coagulant in the incubation medium is of the same concentration as within the freezing medium. According to some embodiments, the incubation medium comprises an anti-coagulant selected from the group consisting of: heparin, ACD Formula A and a combination thereof. Each possibility represents a separate embodiment of the present invention. According to some embodiments, the anti-coagulant used in the incubation medium is ACD Formula A containing heparin at a concentration of 10 U/ml.

According to some embodiments, the incubation medium comprises heparin. According to some embodiments, the heparin in the incubation medium is at a concentration of between 0.1-2.5 U/ml. According to some embodiments, the heparin in the incubation medium is at a concentration of between 0.1-2.5 U/ml, possibly between 0.3-0.7 U/ml, typically about 0.5 U/ml. Each possibility represents a separate embodiment of the present invention. According to certain embodiments, the heparin in the incubation medium is at a concentration of about 0.5 U/ml.

According to some embodiments, the incubation medium comprises ACD Formula A. According to some embodiments, the ACD Formula A in the incubation medium is at a concentration of between 1%-15% v/v. According to some embodiments, the ACD Formula A in the incubation medium is at a concentration of between 1%-15% v/v, possibly between 4%-7% v/v, typically about 5% v/v. Each possibility represents a separate embodiment of the present invention. According to some embodiments, the ACD Formula A in the incubation medium is at a concentration of about 5% v/v.

According to some embodiments, both the freezing medium and the incubation medium comprise an anti-coagulant. According to some embodiments, addition of an anti-coagulant both to the incubation medium and freezing medium results in a high and stable cell-yield between different preparations of the composition of the invention regardless of cell-collection conditions, such as, but not limited to, the timing and/or type of anti-coagulant added during cell collection. According to some embodiments, addition of an anti-coagulant both to the incubation medium and freezing medium results in a high and stable yield of the cell-preparation of the invention regardless of the timing and/or type of anti-coagulant added during leukapheresis. According to some embodiments, production of the cell-preparation of the invention in the presence of a high triglyceride level results in a low and/or unstable cell-yield between different preparations. Each possibility represents a separate embodiment of the present invention. According to some embodiments, producing the cell-preparation from the blood of a donor having a high triglyceride level results in a low and/or unstable cell-yield of the cell preparation. Each possibility represents a separate embodiment of the present invention. According to some embodiments, the term "high triglyceride level" refers to a triglyceride level which is above the normal level of a healthy subject of the same sex and age. According to some embodiments, the term "high triglyceride level" refers to a triglyceride level above about 1.7 milimole/liter. As used herein, a high and stable yield refers to a cell yield in the composition of the invention which is high enough to enable preparation of a dose which will demonstrate therapeutic efficiency when administered to a subject. According to some embodiments, therapeutic efficiency refers to the ability to treat, prevent or ameliorate an immune disease, an autoimmune disease or an inflammatory disease in a subject. Each possibility represents a separate embodiment of the present invention. According to some embodiments, a high and stable cell yield is a cell yield of at least 30%, possibly at least 40%, typically at least 50% of cells in the composition of the invention out of cells initially frozen. Each possibility represents a separate embodiment of the present invention.

According to some embodiments, in case the cell-preparation of the invention is obtained from a donor having a high triglyceride level, the donor will take at least one measure selected from the group consisting of: taking triglyceride-lowering medication prior to donation, such as, but not limited to: statins and/or bezafibrate, fasting for a period of at least 8, 10, 12 hours prior to donation, eating an appropriate diet to reduce blood triglyceride level at least 24, 48, 72 hours prior to donating and any combination thereof. Each possibility represents a separate embodiment of the present invention.

According to some embodiments, addition of an anti-coagulant to the incubation medium and/or freezing medium results in a high and stable cell yield within the composition of the invention regardless of the triglyceride level in the blood of the donor. According to some embodiments, addition of an anti-coagulant to the incubation medium and/or freezing medium results in a high and stable cell yield within the composition the invention when obtained from the blood of a donor having normal or high triglyceride level. According to some embodiments, addition of an anti-coagulant at least to the incubation medium, results in a high and stable cell yield within the composition of the invention regardless of the triglyceride level in the blood of the donor. According to some embodiments, addition of an anti-coagulant to the freezing medium and incubation medium results in a high and stable cell yield within the composition of the invention regardless of the triglyceride level in the blood of the donor.

According to some embodiments, the freezing medium and/or incubation medium and/or washing medium comprise heparin at a concentration of at least 0.1 U/ml, possibly at least 0.3 U/ml, typically at least 0.5 U/ml. Each possibility represents a separate embodiment of the present invention. According to some embodiments, the freezing medium and/or incubation medium and/or washing medium comprise ACD Formula A at a concentration of at least 1% v/v, possibly at least 3% v/v, typically at least 5% v/v. Each possibility represents a separate embodiment of the present invention.

According to some embodiments, the mononuclear-enriched cell composition undergoes at least one washing step between each stage of the production method of the invention. According to some embodiments, anti-coagulant is added to washing media during washing steps throughout the production method of the invention. According to some embodiments, the mononuclear-enriched cell composition undergoes at least one washing step following incubation. According to some embodiments, the mononuclear-enriched cell composition undergoes at least one washing step following incubation using PBS. According to some embodiments, anti-coagulant is not added to the final washing step prior to re-suspension of the cell-preparation in the administration medium. According to some embodiments, anti-coagulant is not added to the PBS used in the final washing step prior to re-suspension of the cell-preparation in the administration medium. According to certain embodiments, anti-coagulant is not added to the administration medium.

According to some embodiments, the cell concentration during incubating is about $5 \times 10^6$ cells/ml.

According to some embodiments, the mononuclear-enriched cell composition is suspended in an administration medium following freezing, thawing and incubating, thereby resulting in the pharmaceutical composition of the invention. According to some embodiments, the administration medium comprises a suitable physiological buffer. Non-limiting examples of a suitable physiological buffer are: saline solution, Phosphate Buffered Saline (PBS), Hank's Balanced Salt Solution (HBSS), and the like. According to some embodiments, the administration medium comprises PBS. According to some embodiments, the administration medium comprises supplements conducive to maintaining the viability of the cells. According to some embodiments, the mononuclear-enriched cell composition is filtered prior to administration. According to some embodiments, the mononuclear-enriched cell composition is filtered prior to administration using a filter of at least 200 µm.

According to some embodiments, the mononuclear-enriched cell composition is re-suspended in an administration medium such that the final volume of the resulting cell-preparation is between 100-1000 ml, possibly between 200-800 ml, typically between 300-600 ml. Each possibility represents a separate embodiment of the present invention.

According to some embodiments, the present invention provides a method for producing the pharmaceutical composition of the invention, wherein the method comprises:
freezing a mononuclear-enriched cell composition comprising at least 65% mononuclear cells in a freezing medium;
thawing the mononuclear-enriched cell composition;
incubating the mononuclear-enriched cell composition in an incubation medium comprising methylprednisolone at a final concentration of about 10-100 µg/mL;
wherein at least one of the freezing medium and the incubation medium comprise an anti-coagulant; and
reconstituting said cell composition in an administration medium, thereby providing the pharmaceutical composition of the invention. Each possibility represents a separate embodiment of the present invention.

According to some embodiments, the method for producing the pharmaceutical composition of the invention further comprises obtaining the mononuclear-enriched cell composition. According to some embodiments, obtaining a mononuclear-enriched cell composition is from the peripheral blood of a donor. According to some embodiments, obtaining a mononuclear-enriched cell composition is from the peripheral blood of the same donor used for transplantation. According to some embodiments, obtaining a mononuclear-enriched cell composition is from the peripheral blood of the same donor donating cells for HSCT. According to some embodiments, obtaining a mononuclear-enriched cell composition for the production method of the invention is from a donor which is not undergoing hematopoietic stem-cells mobilization at the time of obtaining According to some embodiments, obtaining a mononuclear-enriched cell composition for the production method of the invention is from a donor which is not undergoing treatment with Granulocyte Colony Stimulating Factor (G-CSF) at the time of obtaining.

According to some embodiments, the present invention provides a method for producing the pharmaceutical composition of the invention, wherein the method comprises:
obtaining a mononuclear-enriched cell composition from the peripheral blood of a donor, said mononuclear-enriched cell composition comprising at least 65% mononuclear cells;
freezing the mononuclear-enriched cell composition in a freezing medium, wherein said freezing medium comprises an anti-coagulant;
thawing the mononuclear-enriched cell composition;
incubating the mononuclear-enriched cell composition in an incubation medium, wherein said incubation medium comprises an anti-coagulant and methylprednisolone at a final concentration of about 50 µg/mL;
and
suspending said cell composition in an administration medium, thereby providing the pharmaceutical composition of the invention.

According to some embodiments, the present invention provides the cell-preparation of the invention, wherein the cell-preparation is produced by the production method of the invention.

According to some embodiments, the present invention provides a pharmaceutical composition comprising a cell preparation comprising mononuclear enriched cells, wherein the preparation comprises at least 85% mononuclear cells, wherein at least 40% of the cells in the preparation are in an early apoptotic state and wherein at least 85% of the cells in the preparation are viable cells; wherein said pharmaceutical composition is produced by a method comprising:

obtaining a mononuclear-enriched cell composition from the peripheral blood of a donor, said mononuclear-enriched cell composition comprising at least 65% mononuclear cells;
freezing the mononuclear-enriched cell composition in a freezing medium;
thawing the mononuclear-enriched cell composition;
incubating the mononuclear-enriched cell composition in an incubation medium comprising methylprednisolone at a final concentration of about 10-100 µg/mL;
wherein at least one of the freezing medium and the incubation medium comprise an anti-coagulant; and
suspending said cell composition in an administration medium, thereby providing the composition of the invention. Each possibility represents a separate embodiment of the present invention.

According to some embodiments, the present invention provides a pharmaceutical composition comprising a cell preparation comprising mononuclear enriched cells, wherein the preparation comprises at least 85% mononuclear cells, wherein at least 40% of the cells in the preparation are in an early apoptotic state and wherein at least 85% of the cells in the preparation are viable cells; wherein said pharmaceutical composition is produced by a method comprising:
obtaining a mononuclear-enriched cell composition from the peripheral blood of a donor, said mononuclear-enriched cell composition comprising at least 65% mononuclear cells;
freezing the mononuclear-enriched cell composition in a freezing medium comprising an anti-coagulant;
thawing the mononuclear-enriched cell composition;
incubating the mononuclear-enriched cell composition in an incubation medium comprising an anti-coagulant and methylprednisolone at a final concentration of about 50 µg/mL; and
suspending said cell composition in an administration medium, thereby providing the composition of the invention. Each possibility represents a separate embodiment of the present invention.

According to some embodiments, the present invention provides a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes; wherein said pharmaceutical composition is produced by a method comprising:
obtaining a mononuclear-enriched cell composition from the peripheral blood of a donor, said mononuclear-enriched cell composition comprising at least 65% mononuclear cells;
freezing the mononuclear-enriched cell composition in a freezing medium;
thawing the mononuclear-enriched cell composition;
incubating the mononuclear-enriched cell composition in an incubation medium comprising methylprednisolone at a final concentration of about 10-100 µg/mL;
wherein at least one of the freezing medium and the incubation medium comprise an anti-coagulant; and
suspending said cell composition in an administration medium, thereby providing the composition of the invention. Each possibility represents a separate embodiment of the present invention.

According to some embodiments, the present invention provides a pharmaceutical composition comprising a cell preparation comprising mononuclear enriched cells, wherein the preparation comprises at least 85% mononuclear cells, wherein at least 40% of the cells in the preparation are in an early apoptotic state, wherein at least 85% of the cells in the preparation are viable cells and wherein the preparation comprises no more than 15% polymorphonuclear leukocytes; wherein said pharmaceutical composition is produced by a method comprising:
obtaining a mononuclear-enriched cell composition from the peripheral blood of a donor, said mononuclear-enriched cell composition comprising at least 65% mononuclear cells;
freezing the mononuclear-enriched cell composition in a freezing medium comprising an anti-coagulant;
thawing the mononuclear-enriched cell composition;
incubating the mononuclear-enriched cell composition in an incubation medium comprising an anti-coagulant and methylprednisolone at a final concentration of about 50 µg/mL; and suspending said cell composition in an administration medium, thereby providing the composition of the invention. Each possibility represents a separate embodiment of the present invention.

DEFINITIONS

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the terms "v/v" and "vol/vol" are used interchangeably and refer to volume/volume concentration.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "about" refers to plus/minus 10% of the value stated.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Preferably, the method of the present invention is used to treat the disease in a mammalian subject, such as a human subject. It will be readily appreciated that the method can be used to treat a human subject in view of its successful clinical trial phase 1/2a as is described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

The following methods were employed in Examples 1-4 disclosed herein.

Analytical Methods and Specifications for ApoCell

ApoCell was tested during several stages of production. Quality control tests, test methods, testing facility, and specifications relating to the collected mononuclear enriched cells prior to apoptosis induction and the final ApoCell product preparation are described in Table 3 below.

TABLE 3

Specifications for collected mononuclear-enriched cell fraction prior to freezing

| Specification | Test Method | Test |
|---|---|---|
| At least $10^9$ total cells | SYSMEX Hematology Analyzer | Cell Count |
| At least 85% PI negative cells | Flow cytometric analysis of propidium iodide stained cells | Cell viability |
| At least 30% mononuclear cells | SYSMEX Hematology Analyzer | Identity/purity |
| Negative growth at 5 and 14 days | Direct sterility test or equivalent Hy Laboratories | Sterility |
| Less than 1 EU/mL | End safe | Endotoxin |

ApoCell was further tested prior to release for clinical administration. Quality control tests, test methods, testing facility, and specifications for product release are presented in Table 4 below. Sterility and potency were performed after product release.

TABLE 4

Quality Control Test for Release of Product

| Specification | Test Method | Test |
|---|---|---|
| Per protocol | Micros 60 Analyzer | Cell number |
| At least 85% viable | Flow cytometric analysis of propidium iodide stained cells | Cell viability |
| At least 40% apoptotic cells | Flow cytometric analysis of annexin V-propidium iodide | Identity: Apoptosis |
| Negative | Hy Laboratories | Gram Stain |
| Less than 1 EU/mL | Endosafe | Endotoxin |
| $CD15^{high} < 10\%$ | Flow cytometric analysis of CD15 | Identity/Purity |
| Negative growth at 14 days | Direct sterility test Hy Laboratories or equivalent SOP # 10-004-006 | Sterility |
| Inhibition of LPS upregulation of CD86 or MHC class II | Dendritic cell assay or equivalent BR-PT01&PT02 | Potency |

Cell Count

Cell count number is derived from the white blood cell (WBC) count.

Cell Viability Cell viability is determined by propidium iodide staining by flow cytometry.

Identity/Purity

Identity and purity of the collected mononuclear enriched cells was determined from the differential count performed on the SYSMEX hematology analyzer. The identity/purity was calculated by the sum of lymphocyte and monocyte percentage of WBC count. If mononuclear percentage is less that 30% by hematology analyzer, an additional evaluation method can be used—Flow Cytometry with specific identifying antibodies: Double staining for CD15 and CD14 will be performed and the percentage of granulocytes will be determined as a percentage of CD15highCD14low-neg cells. If CD15highCD14low-neg cells portion will be less than 70% the collection will be allowed for further processing. If it is higher than 70%, the specific collection will be discarded. Alternatively equivalent test for granulocyte percentage determination can be used.

Identity/Purity prior to release of the ApoCell product was determined by flow cytometric analysis to evaluate proportion of granulocytes. Double staining for CD15 and CD14 were performed and the percentage of granulocytes was determined as a percentage of $CD15^{high}CD14^{low-neg}$ cells.

Identity: Apoptotic Phenotype

Apoptosis is determined by two-color flow cytometric assay to evaluate the annexin and propidium iodide staining (An+PI−).

Sterility

Each lot of donor cells is tested for sterility using "direct sterility test method" with compliance to FDA regulation 21 CFR 610.12. Samples are monitored daily, and readout results are documented at 14 post inoculation.

Endotoxin (LAL)

The Endosafe-PTS is an FDA-licensed endotoxin detection system that utilizes an LAL test cartridge along with a handheld spectrophotometer to provide point-of-use results. The PTS provides quantitative LAL test results in about 15 min.

Potency

Immature DC (iDCs) were prepared 6 days prior ApoCell preparation as described in Verbovetski et al. (JEM 2002). Briefly, immature monocyte-derived dendritic cells, derived from a subject other than the donor or recipient of the cell-preparation, were generated from the CD14+ selected fraction of blood buffy coats. PBMCs were isolated using Ficoll (GE Healthcare Life Sciences, Piscataway, N.J., US) and anti-CD14 magnetic beads were used in order to isolate monocytes from PBMCs according to the manufacturer's instructions (BD Biosciences, San Jose, Calif., US). Monocytes were placed in wells at a concentration of $1.25 \times 10^6/1.5$ ml culture media in the presence of 1% autologous plasma, GMCSF (0.1 µg/ml), and IL-4 (0.1 µg/ml) (PeproTech, Rocky Hill, N.J., US). Every 2 days 0.15 ml were removed and 0.25 ml media containing plasma, IL-4 (0.05 µg/ml), and GMCSF (0.1 µg/ml), were added. By day 6, >90% of the cells were CD14−, with low expression of DR, CD-83, and CD-86. ApoCell was introduced to iDC at 1:2, 1:4, and 1:8 DCs:ApoCell ratios overnight (16-24 hours). In some treatments, in order to evaluate the anti-inflammatory effect, 10 ng/ml LPS were added 2 h following interaction. Following the interaction the cells were harvested and stained with both DCsign (for verifying the identity of iDC) and HLA-DR or CD86 (for evaluating the pro-inflammatory immune response). Isotype controls were used as controls. Expression of HLA-DR and CD86 on dendritic cells (DCsign positive cells) was evaluated using flow cytometry (FACSCalibur, Becton Dickenson, San Jose, Calif., USA). Analysis was performed on DCsing positive cells (10000 events) using FCSexpress software.

Significant (Kolmogorov-Smirnov analysis) downregulation in at least one of the markers in at least one ratio are used as a marker for tolerizing phenotype of DC following interaction with ApoCell.

Study Design and Patients

A multicenter phase 1/2a clinical trial of ApoCell (registered with clinicaltrials.gov; NO. NCT00524784) was performed in subjects undergoing allogeneic sibling HLA-matched bone marrow transplantation. The study was performed to assess the safety tolerability and preliminary efficacy of ApoCell administration.

The primary endpoint of the study was to determine the safety profile and tolerability (dose limiting toxicity (DLT)) of ascending doses of ApoCell in subjects undergoing allogeneic sibling HLA-matched bone marrow transplantation within 180 days post-transplantation.

The secondary end points were to determine the success rate for allogeneic BMT (alloBMT) engraftment and time to successful engraftment, describe the rates and grade of acute GVHD following ApoCell infusion and determine the immunological function of the recipient following ApoCell infusion and alloBMT. In order to evaluate the outcomes the following parameters were used: Time to neutrophil and platelet recovery, time to full donor chimerism in neutrophils, proportions of subjects with graft failure, relapse or malignancy, incidence of infections (bacterial, viral and fungal), proportions of subjects with overall survival at Day 45 (46 days after ApoCell infusion), at Day 100 and at day 180, proportions of subjects with acute GvHD-free survival at Day 180, rates and grade of acute GvHD following ApoCell infusion, proportions of subjects who developed acute GvHD grade time to onset of acute GvHD. Additional secondary end points included time to engraftment and time to discharge from the hospital.

The initial ApoCell dose level (cohort 1) was $35 \times 10^6$ apoptotic cells/kg, on day −1 of transplantation started with recruitment of one patient first in order to evaluate preliminary safety profile of ApoCell prior to proceeding with recruitment of additional two subjects to the first cohort. ApoCell infusion in first patient met the protocol-defined safety criteria for day 45 and the study proceeded to the second patient with the same dosage that also met the protocol-defined safety criteria. The study then proceeded to the next phase where an interim analysis of safety data was performed by the Data and Safety Monitoring Board (DSMB) after each of cohort 1-3 completed study day 31 and cohort 4 completed study day 45. All cohorts met the DSMB criteria and the study was authorized to be completed.

The initial plan was to recruit 3 patients for each cohort. However the 7th patient received only $90 \times 10^6$ cells/kg instead of $140 \times 10^6$ cells/kg and therefore was immediately included in the second cohort ($70 \times 10^6$ cells/kg) as an additional patient. In total, 13 patients were treated, three in each cohort one, three, and four, and four patients in cohort two.

Eligibility criteria included the following: Adult male or female subjects, 18-60 years of age, at the time of screening visit weighing at least 40 kg and with life expectancy of at least 6 months at the time of the baseline visit. Subjects were eligible for allogeneic sibling HLA-matched alloBMT for any disease for which transplantation is appropriate except progressive or poorly controlled malignancies. The availability of a genotypically HLA-identical sibling, a phenotypically HLA-matched first-degree relative, with at least a 7/8 HLA match at the HLA A, B, C, and DR loci and a clinician decision of a myeloablative regimen, were required.

Exclusion criteria included: pregnancy, positive serology for HIV, active serious infections, T-cell depleted allograft; Karnofsky performance status less than 80%, or serious organ dysfunction (e.g., left ventricular ejection fraction <40%, pulmonary forced vital capacity <60% of predicted, liver transaminases >2.5× the upper limit of normal, or serum bilirubin >3 mg/dL or creatinine >221 µmol/L (2.5 mg/dL).

Conditioning Regimen and Supportive Care

Conditioning regimen for patients were either Busulfan- or Total Body Irradiation (TBI)-based: for Busulphan: P.O busulphan 16 mg/kg×4 days with cytoxan 120 mg/kg or Flu-Bu2-TT2; Fludarabine 30 mg/kg/d for 5 or 6 days, I.V. Busulfan, 3.2 mg/kg/d for 2 days or 4 days, I.V. Thiotepa 5 mg/kg/d for 2 days (regiment name: FBT). For a TBI-based regimen, Cyclophosphamide 60 mg/kg for 2 days I.V. or etoposide (VP-16) 60 mg/kg were administered as well as Total Body Irradiation with a TBI dose of at least 1200 cGy of fractionated TBI. The order of administration of cyclophosphamide and TBI was at the discretion of the transplant center within each institution, all patients should have received the cyclophosphamide and TBI in the same order. If cyclophosphamide or VP16 (etoposide) were given last, there should be at least a one-day rest period before the peripheral blood stem cell infusion. Fractionated TBI was administered according to the institutional protocol. Mesna is allowed, but not required. However, each participating center could employ conditioning regimen according to their local institution guidelines provided it was myeloablative and was used for all patients included in the study at that center. Conditioning regimen with anti-thymocyte globulin (ATG) was prohibited (exclusion criteria).

All dosing was based on ideal body weight and ApoCell was given intravenously on day −1 before transplantation.

GVHD Prophylaxis

Subjects in the study received GVHD prophylaxis regimen that was prescribed according to the normal standard of care and included IV cyclosporin at a dose of three mg/kg initiated on Day −1 (the dose were adjusted according to plasma levels) and IV methotrexate at the doses of 15 mg/m$^2$, 10 mg/m$^2$, 10 mg/m$^2$ on Days +1, +3 and +6 respectively (three doses of folinic acid were given starting 18 hours after each dose). Cyclosporin was given orally when the patient was able to swallow and continued until Day +90 (in accordance with disease status and chimerism).

Chimerism was assessed by standard cytogenetic analysis in male/female donor-recipient. Residual male cells in female chimera were detected by amelogenine gene method. In sex-matched donor-recipient combinations, the VNTR (Variable number of tandem repeats) PCR assay and later on the STR (short tandem repeats) PCR assay with a 5% sensitivity of detection were used to assess the presence of residual host or donor cells. Additional historical controls representing the last decade were taken from Gooley et al. (Gooley T A, NEJM 2010).

All infection events were recorded and graded with accordance with the National Cancer Institute Common Terminology Criteria for AEs (version 3). Time to infection was evaluated through Day 180. CMV was tested on screening, days 3, 10, 17, 31, 45, 66, 100 and 180 study visits.

There were acute follow-up period (days −1 to 3), short-term follow-up period (visits on days 10, 17, 31, and 45), and long-term follow-up period for acute GVHD (visits on days 66, 100, and 180). The window visit were ±2 days for each weekly visit and ±5 days for biweekly or more visit during the follow up periods.

Regimen-Related Toxicity

Adverse events (AEs) were reported and graded in accordance with CTCAE (version 3). A relationship between the AE and ApoCell versus those typically associated with HSCT and GVHD were carefully assigned in accordance with the guidance in clinical protocol. GVHD severity was determined clinically, however, biopsies of affected organs were strongly encouraged whenever possible.

Also, the timing of the infusion of the ApoCell product at 24 to 30 hours before alloBMT in all cohorts allowed an additional safety evaluation in this 24 to 30 hour period before the stem cell infusion.

Non-Regimen Related Toxicity and Non-Relapse Mortality (NRM)

Morbidity and mortality related to transplantation included reports of serious AE (SAE) and documentation of graft failure, veno-occlusive disease (VOD), sepsis or bacterial infections, noninfectious pneumonia, hemorrhage, refractory GVHD, and multisystem organ failure. Non-fatal toxicity include any SAE or documentation of grade IV ALT, AST, or bilirubin elevation, Grade III serum creatinine, reversible VOD, hemorrhagic cystitis, pericardial effusion, or subdural hematoma.

Diagnosis and Treatment of GVHD

Acute GVHD was graded according to Thomas E D et al. (Thomas E D et al. NEJM 1979) through day 100 of the study. Chronic GVHD (cGHVD) was graded according to Filipovich A H et al. (Biol Blood Marrow Transplant 2005) from day 100 till day 180. The broad category of chronic GVHD includes (1) classic chronic GVHD without features characteristic of acute GVHD and (2) an overlap syndrome in which features of chronic and acute GVHD appear together. In the absence of histologic or clinical signs or symptoms of chronic GVHD, the persistence, recurrence, or new onset of characteristic skin, GI tract, or liver abnormalities should be classified as acute GVHD regardless of the time after transplantation.

Engraftment and Donor Chimerism

Neutrophil engraftment was defined as achieving an absolute neutrophil count (ANC) >0.5×10$^9$/L for three consecutive measurements on different days. The first of the three days was designated the day of neutrophil engraftment. Platelet engraftment was defined as a platelet count >20× 10$^9$/L for three consecutive measurements over three or more days without platelet support. The first of the three days was designated the day of platelet engraftment. Subjects must not have had platelet transfusions during the preceding 3 days or in the following 7 days after the day of engraftment. The time to a platelet count >100×10$^9$/L was collected as well. Chimerism was assessed on days 10, 31, 45, 66, 100 and 180. Primary graft failure was defined as a lack of neutrophil recovery in the absence of progressive malignancy affecting the marrow. Secondary graft failure was defined as loss of donor engraftment (<5% donor chimerism) in the absence of progressive malignancy affecting the marrow.

Time to First Hospital Discharge

Time to first hospital discharge was defined as the time from the day of HSCT (Day 0) to the date of first hospital discharge and was recorded as the length of the initial hospital stay.

Apo Cell Preparation

The ApoCell product contains apoptotic cells produced from a mononuclear enriched cell fraction from a sibling HLA-matched donor. Eligibility criteria for donors included the following: adult male or female donors, 18-65 years of age; the donor and recipient must have at least a 7/8 HLA match at the HLA A, B, C, and DR loci; above 40 kg; willingness to donate hematopoietic blood mononuclear cells for the generation of ApoCell in addition to the donation for the HSCT. Eligible donors returned to the clinic approximately at Day −19 for peripheral blood mononuclear harvesting using leukapheresis procedure (Cobe® Spectra™, Gambro BCT, Lakewood, Colo., USA) according to the local SOPs. During the approximate 2.5 hours of leukapheresis, 7 L of blood was processed and cells were collected at room temperature into a transfer pack. The estimated yield of the enriched mononuclear cell fraction from a donor was 1.0×10$^{10}$ cells in an estimated volume of 100-140 ml. The mean percentage of mononuclear cell fraction in the cell collections resulting from the leukapheresis was 88±8% (ranging between 65-96%). Cell yields varied depending on the donor variability. The collected mononuclear enriched cell fraction from the HLA-matched donors underwent sequential processes for inducing early apoptosis through a multistep procedure including freezing and thawing the cells followed by incubation with methyl-prednisolone. The ApoCell final suspension contained at least 40% of early apoptotic cells. The cell suspension for infusion was prepared under current Good Manufacturing Procedures (cGMP). Infusions were performed 24-30 hours before HSCT and within 8 hours of completion of preparation. Cells were stored at 2-8° C. until administered.

Plasma Biomarkers

Plasma and serum samples were obtained on screening and on study visit days −1 (before ApoCell infusion), day 0 (before HSCT) and days 3, 10, 17, 31, 45, 66, and 100. To ensure optimal recovery, plasma and serum samples were aliquoted within 2-4 hours after collection and stored at −80° C. until measurement of cytokine levels. Following cytokines were measured: TNFR1, IL-2Ra, HGF, IL-8, IL-7, IL-15, IL-6 and IL-1β (for IL-7 measurement highly sensitive kit was used) all from R&D systems (MN, USA). IL-7 and IL-15 were tested from screening till day 31 study visits and all other cytokines till day 100 study visit unless stated otherwise. ELISAs were performed in duplicates. Plates were analyzed with Infinite F50 absorbance reader (Techan, Austria) using Magellan software. The results are presented as median concentration levels.

Statistical Analysis

Descriptive statistics were used to summarize outcome measures and baseline characteristics. In this analysis all available data were presented with no imputation for any missing data. Subjects contributed the data available up to the point of withdrawal or study completion or death. Descriptive statistics including means, median, standard deviation (SD), minimum and maximum values were used to summarize continuous variables. Dichotomous variables were presented as count and percentages. Student-t-test was used to compare mortality and GVHD occurrence to historical controls and previous reports. All subjects who received the ApoCell infusion were included in the safety analysis. Student t test (two tail type 1) was used for potency assay analysis.

Historical Controls

Historical control patients were selected from the computerized registry at the Bone Marrow Transplantation & Cancer Immunotherapy Center, Hadassah University Hospital according to the following rules: underwent allogeneic stem cell transplantation from a matched sibling donor and have similar age, sex, disease, disease status and conditioning regimen to the current study patients. The data was verified from the patients' electronic files prior to analysis. Control group consisted of 25 patients (18 were males and 7 females), with median age of 26 years (range 9-63). All patients were referred to the Hadassah Hospital for BMT between 1982 and 2009. As it was a prerequisite for the patients' selection for this analysis, all patients were transplanted from fully matched HLA class I and II family members (24 siblings and 1 father).

Engraftment data was found for 21 patients. Late rejection occurred in one patient (5%). Engraftment of neutrophils was achieved in all (21 out of 21) patients at a median of 14 days (range 9-22 days). Engraftment of platelets was achieved in 16 out of 18 evaluable patients at a median of 12.5 days (range 9-32 days).

Eighteen of the 25 (72%) control patients were discharged from the initial transplant admission. The median hospital stay was 40.5 days (range 27-79 days).

GVHD: Fifteen of the 25 control patients (60%), developed acute GVHD grade I-IV at a median time of 26 days. The incidence of grade II-IV acute GVHD was 50% (12 of 24 patients and III-IV acute GVHD was 20% (5/25 patients).

Transplant-related mortality (TRM): 7 out of 25 (28%) patients died during the first 100 days due to transplant related complications. None of the surviving patients died between days 100 to 200 from transplant complications, thus TRM was kept at 28% at 200 days. Death was caused due to infection in 3 patients, GVHD in one, GI bleeding in one, rejection in one and cardiac arrest in one.

Transplant-related toxicity (TRT): creatinine—4 of the 18 patients (22%) with available kidney function data had renal failure defined as creatinine >1.5× upper normal levels up to day +200. In 2 of them renal failure was severe and necessitated intervention. Bilirubin—7 of the 18 patients (39%) with available bilirubin level data experienced significant hepatotoxicity defined as bilirubin >2× upper normal levels up to day +200.

The following methods were employed in Examples 5-10 disclosed herein.

Cell Cultures and Reagents.

Cells were cultured in Dulbecco's modified Eagle's medium (DMEM), with high glucose supplementation (Invitrogen-Gibco, Carlsbad, Calif.), and with 1% L-glutamine (Biological Industries, Israel), 10% fetal bovine serum (Biological Industries), and 10 µg/ml ciprofloxacin (Sigma Aldrich, Israel). The caspase-1 inhibitor z-YVAD-fmk, nigericin, and bafilomycin A1 were purchased from Calbiochem (Darmstadt, Germany) N-acetyl-L-cysteine (NAC) and lipopolysaccharide (LPS) were from Sigma Aldrich. DSS reagent was from MP Biomedicals (Illkirch, France). For immunostaining, the following antibodies were used: anti-COX2 (Cayman Chemicals, Ann Arbor Mich., USA), anti-myeloperoxidase (Thermo Scientific, Waltham Mass., USA), anti-phospho-IκBα and anti-phospho-NF-κB p65 (Cell Signaling, Danvers Mass., USA).

Generation of Apoptotic Cells.

A composition containing human apoptotic cells (Apo-Cell) was produced from the mononuclear enriched cell fraction of healthy volunteer donors in a leukapheresis procedure. During leukapheresis, approximately 300 ml of autologous plasma was collected from the donor for subsequent use in the preparation of the apoptotic cells. The plasma was collected in a transfer pack, aliquated and frozen for 2 hours at −80° C. and then stored at −18-(−25°) C. till manufacturing. Collected cells met all specifications for harvested cells as described in Table 3 above. Differential count was performed on the SYSMEX hematology analyzer. Cell viability was determined by propidium iodide staining by flow cytometry. Following collection, cells were washed with RPMI 1640 supplemented with 2 mM L-glutamine, 10 mM Hepes and 5% of ACD formula A containing 10 U/ml Heparin and frozen at $5$-$6.5 \times 10^7$ cells/ml in freezing bags. The final formulation of the freezing medium was RPMI 1640 supplemented with 2 mM L-glutamine, 10 mM Hepes, 5% Hes, and 10% dimethyl sulfoxide (DMSO) containing 20% autologous plasma and 5% of ACD formula A containing 10 U/ml Heparin. Next, cells were thawed and washed with RPMI 1640 supplemented with 2 mM L-glutamine, 10 mM Hepes and 5% of ACD formula A containing 10 U/ml Heparin. Cells were then re-suspended to a final concentration of $5 \times 10^6$/ml in RPMI 1640 supplemented with 10 mM Hepes, 2 mM L-glutamine, with addition of 10% autologous plasma, 5% of ACD formula A containing 10 U/ml Heparin and 50 µg/ml methylprednisolone and incubated for six hours in LifeCell flasks at 37° C., 5% $CO_2$. Following incubation, cells were harvested, washed with PBS and re-suspended at the desired concentration in PBS.

Apoptotic Cell Measurement.

Apoptosis was assessed using Annexin V and propidium iodide (PI) apoptosis detection kit (MBL International, Woburn Mass., USA). Cells were acquired with a FACSCalibur instrument and analyzed using FCS Express software (De Novo, Los Angeles, Calif., USA). Apoptotic cells routinely contained at least 40% AnnexinV and <5% PI-positive cells were used in all experiments.

Isolation of peritoneal macrophages. Primary resident peritoneal macrophages (pMΦ) of WT or Nlrp3−/− mice were generated as described elsewhere (Bauer et al. 2010). Briefly, mice were sacrificed under isoflurane anesthesia by cervical dislocation. Peritoneal lavage was then performed by exposing the parietal peritoneum and injecting intraperitoneally with a transpipette 10 ml of 2% FBS in PBS. The peritoneal lavage fluid was centrifuged and re-suspended at the desired concentration. The adherent pMΦ (F4/80 positive cells) subset consists about 20% of the peritoneal lavage as observed by flow cytometer analysis. Cells were then plated into culture dishes overnight. Cells were washed, and adherent cells were used for cytokine assays. Where indicated, experiments were performed after four weeks of co-housing WT and NLRP3-deficient mice to neutralize the microbiota effect.

IL-1β ELISA.

pMΦ were seeded into 96-well plates at a density of $2 \times 10^5$ cells per well. After LPS priming for 1 h, cells were stimulated with different activators for 24 h. Cell culture supernatant was used for ELISA (Biolegend, San Diego Calif., USA), which was performed according to the manufacturer's protocol.

Western Blotting.

The processed IL-1β p17 subunit and activated caspase-1 p10 subunit and their release into the culture supernatant were determined by Western blotting. In brief, 12 hours after indicated activators addition, the supernatant was collected and suspended in SDS-PAGE sample buffer, and heated to 85° C. for 10 min Macrophages were lysed in lysis buffer (50 mM Tris-HCl pH8.0, 5 mM EDTA, 150 mM NaCl, 1% Triton-X 100 and a protease inhibitor cocktail (Roche)) and stored at −80° C. until analyzed. Protein from $1 \times 10^6$ macrophages was loaded per well of a 15% acrylamide gel and transferred to a PVDF (poly(vinylidene difluoride)) membrane by electroblotting. Western blots were performed with anti-mouse IL-1β antibody (clone B122; Biolegend) diluted 1:500 and anti-mouse caspase-1 p10 antibody (Santa Cruz) diluted 1:1000. Appropriate HRP-conjugated secondary antibodies (Jackson ImmunoResearch Laboratories, West Grove, Pa., USA) were used and proteins detected using ECL reagent (Biological Industries). An anti-mouse actin served as a loading control.

Induction of Colitis.

Colitis was induced by oral administration of 3% (w/v) DSS solution (m.w. 36,000-50,000; MP Biomedicals) ad libitum in drinking water for 7-9 days until sacrifice. The control group received distilled water (0% DSS) during the same time. Where apoptotic cell treatment was applied, mice received a single infusion into tail vain containing $25\text{-}30 \times 10^6$ cells/150 μl in PBS. Control mice received 150 μl PBS.

Induction of Colitis by Adoptive T-Cell Transfer.

Naïve $CD4^+CD45RB^{high}$ T cells were isolated from spleens of C57BL/6 mice via FACS sorting as previously described (Izcue, 2008). In brief, after negative enriching for CD4+ lymphocytes, single-cell suspensions were stained with APC-conjugated anti-CD4 and FITC-anti-CD45RB (all obtained from biolegend). Naïve $CD4^+CD45RB^{high}$ T cells were purified (>99%) with a FACSAria cell sorter (BD Biosciences, San Jose, Calif.). The $CD4^+ CD45RB^{low}$ population was also sorted and served as the negative control. Sex-matched $Rag1^{-/-}$ recipient mice received $5 \times 10^5$ $CD4^+ CD45RB^{high}$ or $CD4^+CD45RB^{low}$ T cells by intraperitoneal (i.p.) injection, and development of intestinal inflammation was monitored as described below. Groups receiving apoptotic cell treatment were injected with a dose of $30 \times 10^6$ ApoCell/150 μl PBS per mouse on indicated days via tail vain. Control groups were injected with 150 μl PBS only.

General Assessment of Colitis.

Mice were sacrificed when symptoms of clinical disease became apparent in control groups, usually around 7-9 days in DSS-model and 8 weeks in TCT model. IBD was assessed using a standard IBD Clinical Score by daily measurements of weight change, stool consistency, and hematochezia, as described elsewhere (Hartmann, 2000), with modification. No weight loss was counted as 0, weight loss of 1 to 5% as 1, 5 to 10% as 2, 10 to 20% as 3, and >20% as 4 points. For stool consistency, 0 points were awarded for well-formed pellets, 2 for pasty and semi-formed stools that did not stick to the anus, and 4 for liquid stools that did stick to the anus. Bleeding was scored as 0 points for no blood in hemoccult, 2 for positive hemoccult, and 4 for gross bleeding. These scores were added to form a total clinical score that ranged from 0 (healthy) to 12 (maximal colitis activity). After sacrificing the animals, colons were dissected and fixated in 4% formaldehyde, and embedded in paraffin before staining with hematoxylin and eosin. Histological quantification of mucosal damage, presence and extent of inflammation, crypt damage, and percent involvement, with a range from 0 to 4, was performed on distal colon sections of the specimens. Specimens and treatment groups were blinded before histological quantification.

Measurement of Reactive Oxygen Species (ROS).

Production of ROS by the inflammasome triggering agent DSS was measured with the ROS detection kit (Enzo Life Sciences, Farmingdale N.Y., USA). pMΦ from female B6 mice were seeded onto eight-chamber slides at density $0.1 \times 10^6$ cells/chamber, and cultured at 37° C. overnight. Thereafter, pMΦ were washed twice with PBS, treated for two hours with apoptotic cells at a 1:8 ratio, washed, primed with LPS, and treated with 3% DSS for an additional 30 minutes. Negative control cells were treated with media only. After washing, the cells were suspended in 200 μl of DMEM and stained with the ROS detection reagent (1 μM) for 30 minutes. DSS-induced intracellular ROS was detected by fluorescence microscope examination at 488 nm excitation wavelength with a 525-nm emission filter. (Original magnification ×100). Where flow cytometer detection was applied, MΦ were detached by trypsin-EDTA after treatment, washed, and analyzed using an LSRII instrument (BD Biosciences).

Lysosomal Stability Evaluation.

Lysosomal damage by DSS challenge was evaluated by acridine orange stain as described elsewhere (Bauer et at 2010). Briefly, peritoneal macrophages were plated into 24-well culture dishes overnight, which after non-adherent cells were washed with PBS. The remaining adherent macrophage cells were introduced to apoptotic cells (1:8) for two hours. Macrophages were then washed, primed with LPS during one hour and stimulated for 24 h with DSS. Cells were then washed and incubated with 0.25 μg/ml acridine orange for 15 minutes for lysosome stain. Lysosomal damage was determined as loss of fluorescence intensity emission at 600-650 nm with an LSRII (BD Biosciences).

Immunohistochemistry.

Paraffin-embedded slides from Balb/c mice were deparaffinized and incubated in 3% H2O2. Antigen unmasking was carried out by microwave heating (20 min) in 10 mM Tris buffer containing 1 mM EDTA. Slides were incubated with primary antibodies anti-COX2, anti-MPO, anti-pNF-κB, and anti-pIκBα diluted in CAS-Block (Invitrogen), or with CAS-Block alone as a control. Appropriate secondary antibodies (Nichirei) were then added and slides were incubated at room temperature for 30 min Color was developed using the DAB substrate kit (Thermo Scientific) followed by counterstaining with Mayer's hematoxylin (Sigma Aldrich). Controls without addition of primary antibody showed low or no background staining in all cases.

Animals and Co-Housing.

BALB/c or C57BL/6 mice were obtained from Harlan Inc. (Jerusalem, Israel). Mice were all female and 8-10 weeks of age upon arrival. Where indicated, experiments were performed after 4 weeks of co-housing WT and NLRP3 deficient mice to neutralize the microbiota effect.

Statistical Analysis.

All data are expressed as mean±SEM. The statistical significance of the differences was evaluated by unpaired t-test (two-tailed, except where indicated otherwise) or one way ANOVA with Tukey's multiple comparison tests. P values of 0.05 or less were considered to be statistically significant.

Results

Example 1

Infusion of Allogeneic Apoptotic Cells as Prophylaxis of GVHD in Myeloablative Allogeneic Bone Marrow Transplantation is Safe Patient, Donor, and Graft Characteristics Median total number of cell transplanted and CD34+ cells infused into recipients were $13.6 \times 10^8$/kg (range, 9.3-29.5 $10^8$/kg) and $7.2 \times 10^6$/kg (range, $3.7-22.4 \times 10^6$/kg), respectively (Table 1). Patient, disease, and transplantation characteristics are summarized in Table 1. The most common diagnosis was acute lymphoblastic leukemia (ALL; n=7, 54%), followed by acute myeloid leukemia (AML; n=5, 38%) and one patient with chronic myeloid leukemia (CML; n=1, 7.7%). In patients with AML, one patient presented with disease de novo, and four patients developed AML from an antecedent myelodiplastic syndrome (MDS). A total of five patients with ALL were in first complete remission (CR1), one patient was in second complete remission (CR2) and one patient in second partial remission (PR2). A total of five patients with AML were in CR1. The single patient with CML was in chronic phase and was unresponsive to three tyrosine kinase inhibitor (TKI) before transplantation. All patients received related donor allografts. The median patient age was 37 years (range, 20-59). In addition to HLA match on HLA A, B, C (was evaluated in 8 of 13 patients) and DR loci, DQ was also evaluated in 12 of 13 patients. HLA-matching data is presented at Table 1.

Potency Assay

Tolerogenic DC can be generated upon interaction with apoptotic cells (Verbovetski I J Exp Med 2002) or apoptotic cell products (Krispin A Blood 2006). To each ApoCell preparation, the tolerogenic effect of the prepared ApoCell was specifically examined using in vitro interaction with immature dendritic cells (iDCs). iDCs express low level of HLA-DR and co-stimulatory molecules. Following the exposure to maturation stimuli like LPS, iDCs undergo maturation and upregulate expression levels of HLA-DR and costimulatory molecule CD86.

Potency assay results from 13 ApoCell preparations infused to the patients are summarized in Table 2. The results represent average percentage of inhibition in maturation of LPS treated DCs (inhibition in DR and CD86 expression) following interaction with ApoCell. As shown in Table 2, significant and dose-dependent down regulation was seen. Representative results from one patient potency assay are shown in FIG. 1.

TABLE 2

Potency assays summary from 13 ApoCell preparations

| P-Value | % Inhibition of maturation by LPS ± STD | DCs:ApoCell ratio | Marker |
|---|---|---|---|
| 0.0146 | 30.4 ± 25.8 | 1:2 | DR |
| 0.0002 | 52.1 ± 35.7 | 1:4 | |
| 0.0002 | 67.2 ± 31.8 | 1:8 | |
| 0.0147 | 40.5 ± 25.7 | 1:2 | CD86 |
| 0.0004 | 66.3 ± 26.2 | 1:4 | |
| 0.0000 | 81.0 ± 20.5 | 1:8 | |

TABLE 1

Patient and BMT characteristics

| Infused cell doses Total ($\times 10^8$/kg)/ CD34+ ($\times 10^6$/kg) | Conditioning regimen myeloablative | Disease severity HLA-matching | Diagnosis | Weight | Gender | Age | Patient Cohort |
|---|---|---|---|---|---|---|---|
| 12.5 × $10^8$/kg/ 3.69 × $10^6$/kg | Flud Busflex Thiotepa Cytarasine | CR1; L2 | ALL | 81 | M | 38 | Cohort 1-1 |
| 20.34 × $10^8$/kg/ 22.38 × $10^6$/kg | Cytoxan TBI, ARAC and Methotrexate | PR2; L1 | ALL | 64 | F | 38 | Cohort 1-2 |
| 29.5 × $10^8$/kg/ 7 × $10^6$/kg | Cytoxan, TBI | CR1; T-ALL | ALL | 58 | M | 30 | Cohort 1-3 |
| 10 × $10^8$/kg/ 6.8 × $10^6$/kg | Cytoxan, TBI | CR2; L2 | ALL | 77 | M | 25 | Cohort 2-1 |
| 13.6 × $10^8$/kg/ 15.8 × $10^6$/kg | Flud Busflex Thiotepa | CR1 | MDS, AML | 83 | F | 59 | Cohort 2-2 |
| 24.8 × $10^8$/kg/ 8.1 × $10^6$/kg | Cytoxan, TBI | CR1; L1 | ALL | 40 | M | 24 | Cohort 2-3 |
| 9.3 × $10^8$/kg/ 18.6 × $10^6$/kg | Flud Busflex Thiotepa | CR1; M0 | MDS, AML | 78 | M | 58 | Cohort 2-4 |
| 18 × $10^8$/kg/ 7.2 × $10^6$/kg | Busulphan Cytoxan | CR1 | MDS AML | 100 | M | 49 | Cohort 3-1 |
| 21.6 × $10^8$/kg/ 9.7 × $10^6$/kg | Busulphan Cytoxan | CR1; M1-M2 | MDS, AML | 96 | M | 37 | Cohort 3-2 |
| 19.3 × $10^8$/kg/ 16.6 × $10^6$/kg | Cytoxan TBI | CR1; T-ALL | ALL | 85 | M | 23 | Cohort 3-3 |
| 10.2 × $10^8$/kg/ 6.35 × $10^6$/kg | Cytoxan TBI | CR1; L2 | ALL | 72 | M | 20 | Cohort 4-1 |
| 10.5 × $10^8$/kg/ 7.19 × $10^6$/kg | Busulphan Cytoxan | Chronic phase | CML | 51 | F | 37 | Cohort 4-2 |
| 11 × $10^8$/kg/ 6.55 × $10^6$/kg | Flud Busflex | CR1; M2 | AML de novo | 111 | M | 40 | Cohort 4-3 |

Engraftment

The median time to neutrophil recovery for recipients was 13 days (range, 11-19), and the median time to platelet recovery was 15 days (range, 11-59). Median time to neutrophil and platelets engraftment in the first cohort was 13 days (range 13-14 days) and 17 days (range 11-59) respectively; in the second cohort, 14 (range 11-17) and 14 (range 11-18), respectively; in the third cohort, 14 days (range 12-19) and 15 days (range 13-54) respectively; and in the fourth cohort 12 days (range 11-13) and 15 days (range 13-17) respectively.

Ten of 12 patients (83%) with available data of chimerism on day 31 of the study were donor type. One additional patient had poor technical test that yielded no result on day 31 and was found to be donor type on the following visit (day 45). 100% of patients converted to donor type by day 66. Primary graft failure did not occur. None of the patients with mixed chimerism at day 31, were found to have early disease relapse.

Adverse Events

Ten SAEs were reported with all being not related (seven) or unlikely to be related (three) to ApoCell infusion. Documented SAEs were: two septic shocks, two relapses, one hemorrhagic cystitis, one gastroenteritis due to adenovirus infection, one vomiting, and three incidences of fever. Out of hundreds AE, only three were reported as possibly related to ApoCell infusion (with no definite or probable AE related to ApoCell); one hypotension on the day of the infusion (day −1), one throat irritation on the day of the infusion (day −1) and one relapse on day 131 of the study.

Relapse

The cumulative incidence of relapse at 100 days and 180 days after transplantation was 7.7% (n=1) and 31% (n=4), respectively. Three of four patients with relapse (75%) had ALL. All received cyclosporine.

Survival

Figure 2A:
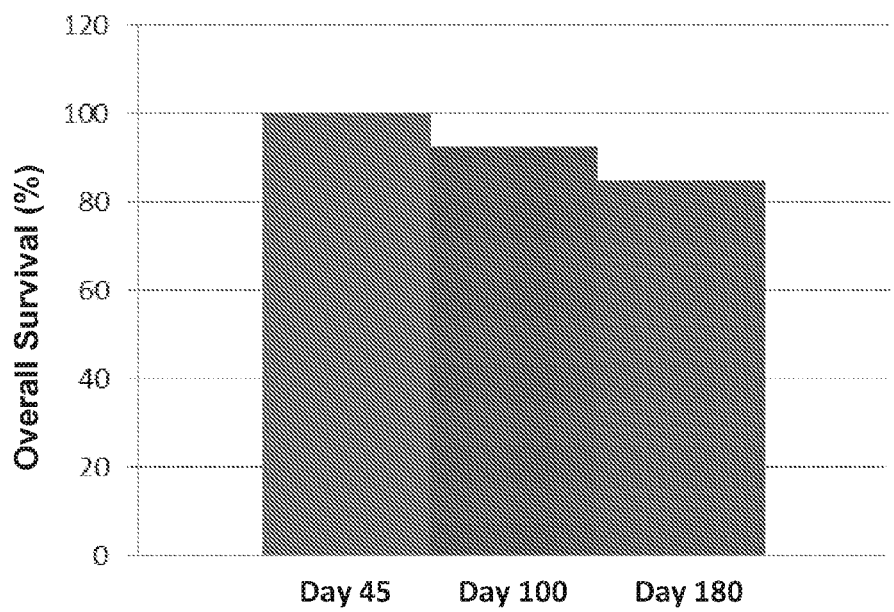
FIGS. 2A and 2B are histograms illustrating the increased rate of overall survival and non-relapsed survival, respectively, in patients receiving a single dose of apoptotic cells. Survival (percent) of transplant patients in all four of cohorts I-IV (n=13), receiving 35-210×10$^6$ apoptotic cells prepared according to the methods disclosed herein is depicted at day 45, day 100 and day 180 of the study.
Figure 2B:
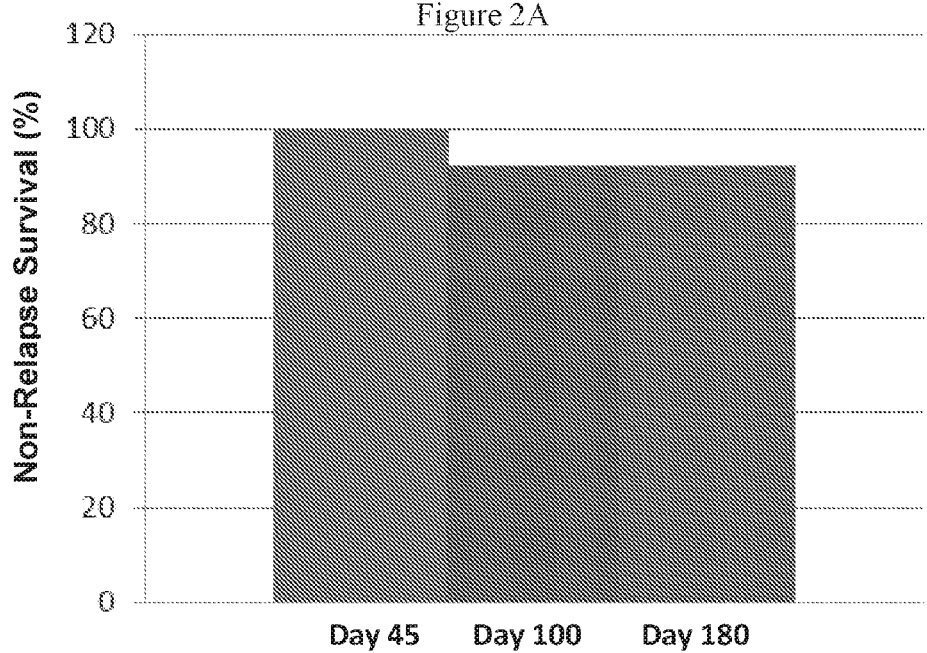
Figure 2C:
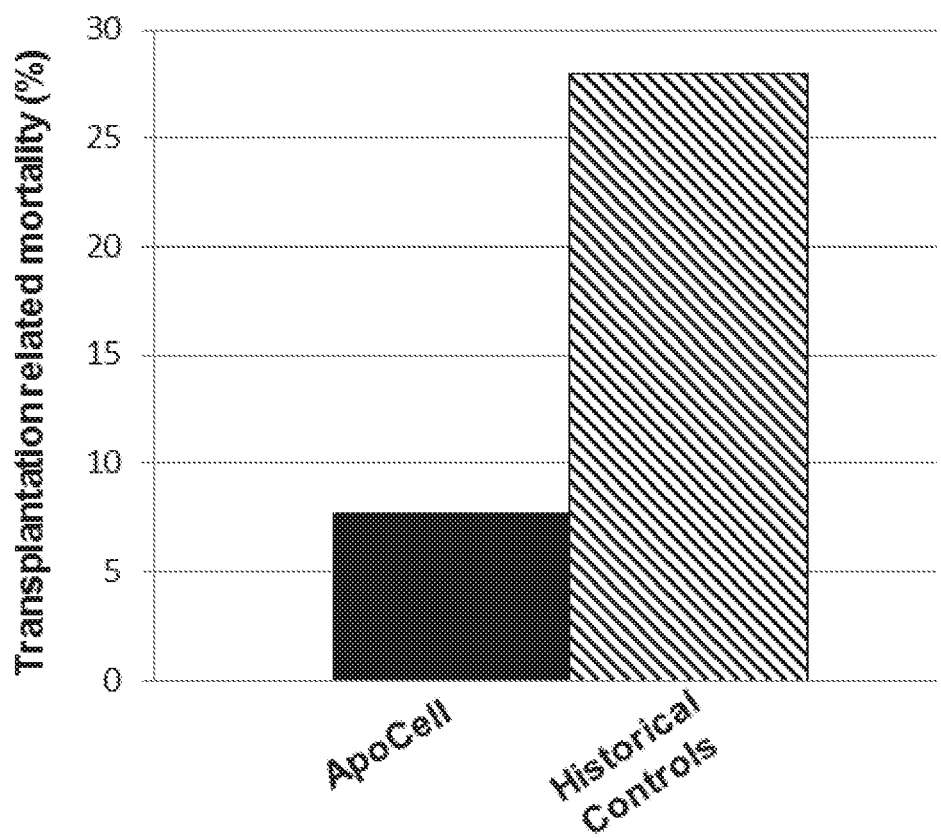
FIG. 2C is a histogram illustrating transplantation related mortality of bone-marrow transplanted patients who received a single infusion of the ApoCell composition (n=13; ApoCell) as compared to the survival rate of matched controls from hospital records (n=25; Historical Controls).

Overall survival on day 45, 100 and 180, was 100%, 92.3% and 84.6%, respectively (FIG. 2A). Survival not related to relapse was 100% on day 45, 92.3% on day 100 and on day 180 (FIG. 2B). Transplantation related mortality (TRM) was 0% on day 45, 7.7% on day 100 and 7.7% on day 180. Only one patient in the treatment group (7.7%) died (FIG. 2C; column 1), compared to 7 (28%) of the matched historical controls from hospital records (FIG. 2C; column 2) and 16% in the retrospective survey (data not shown).

Time to First Hospital Discharge

Figure 3:
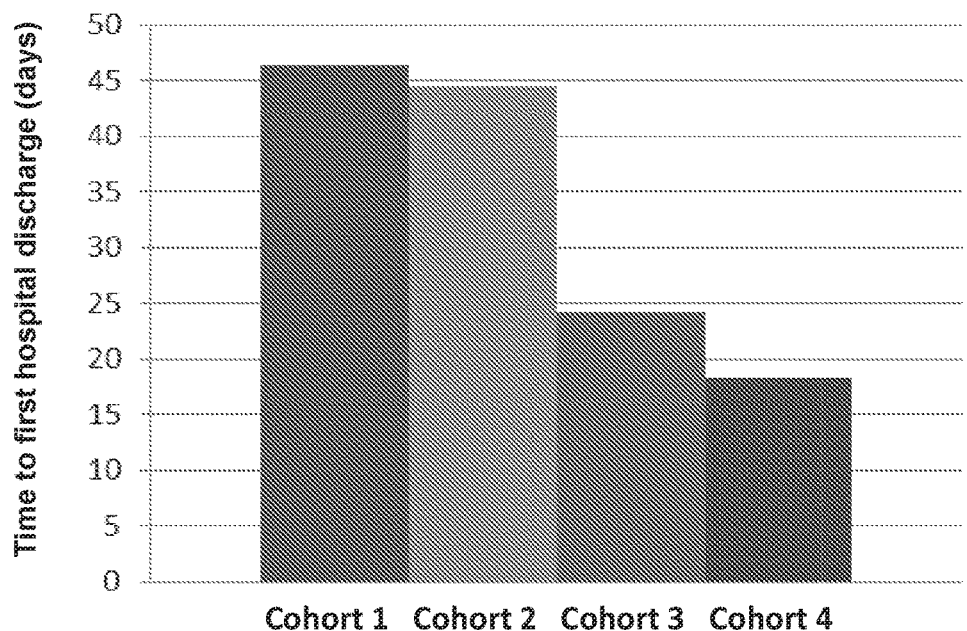
FIG. 3 is a histogram illustrating the time to first hospital discharge for the treated patients in each cohort.

Mean time to first hospital discharge for all 13 patients was 34.2 days (range 15-103 days). Mean time to first hospital discharge for three patients treated in the first cohort dose ($35 \times 10^6$/kg) was 46.3 days (range 15-103 days); mean time to first hospital discharge for four patients treated in the second cohort dose ($70 \times 10^6$/kg) was 33.5 days (range 20-87 days); mean time to first hospital discharge for three patients treated in the third cohort dose ($140 \times 10^6$/kg) was 24.3 days (range 22-28 days) and mean time to first hospital discharge for 3 patients treated in the last cohort dose ($210 \times 10^6$/kg) was 18.3 days (range 17-21 days) (FIG. 3).

The results presented here suggest that single-infusion of donor early apoptotic cells (ApoCell) as prophylaxis of graft-versus-host disease in myeloablative allogeneic bone marrow transplantation is safe. ApoCell was given 24 hours before BMT and no related or possibly related SAEs specific for ApoCell infusion were reported. A total of ten SAE were reported with all being or not related (seven) or unlikely to be related (three) to ApoCell infusion. Out of hundreds AE, only three were reported as possibly related to ApoCell infusion: hypotension on the day of the infusion, throat irritation also on the day of the infusion, and relapse on day 131 of the study. No definite or probable adverse effects related to ApoCell were reported. In addition, no prolonged time to engraftment, duration of hospitalization, chimerism delay, increased rate of mortality, CMV or any serious infections, and relapses, was observed when compared to historical controls and similar patients described in the literature (Gooley ibid.), in all doses examined.

Example 2

Figure 4A:
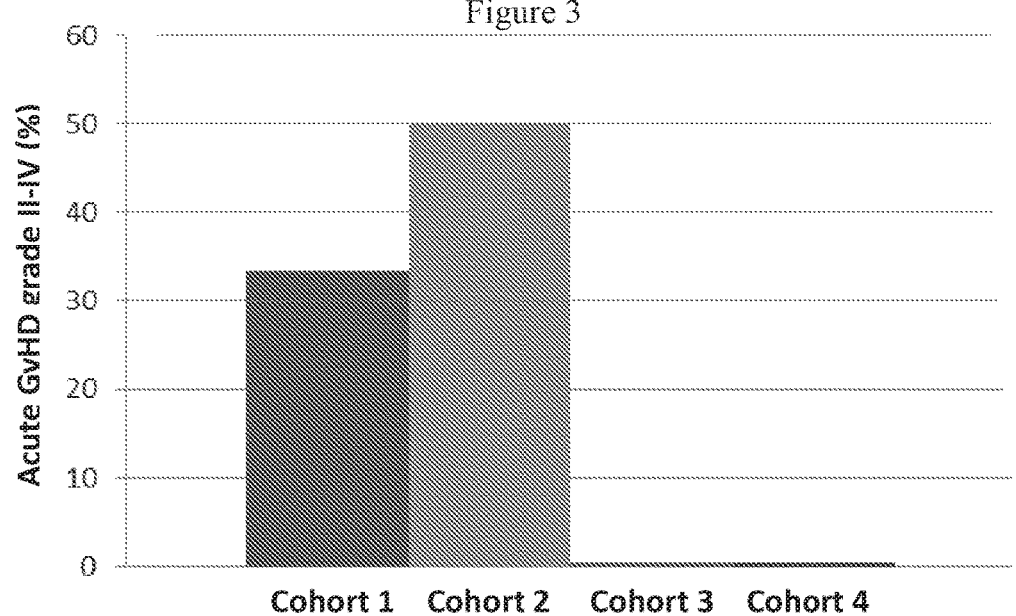
FIG. 4A is a histogram illustrating the reduced incidence of grade II-IV GVHD in transplant patients receiving a single high dose of apoptotic cells. The number (percent) of transplant patients developing acute grade II-IV GVHD in each of four cohorts I (35×10$^6$ apoptotic cells), II (70×10$^6$ apoptotic cells), III (140×10$^6$ apoptotic cells) and IV (210× 10$^6$ apoptotic cells) receiving the apoptotic cell preparations. Notably, no patients in the higher dosage treatment groups (cohorts III and IV) developed acute grade II-IV GVHD.
Figure 4B:
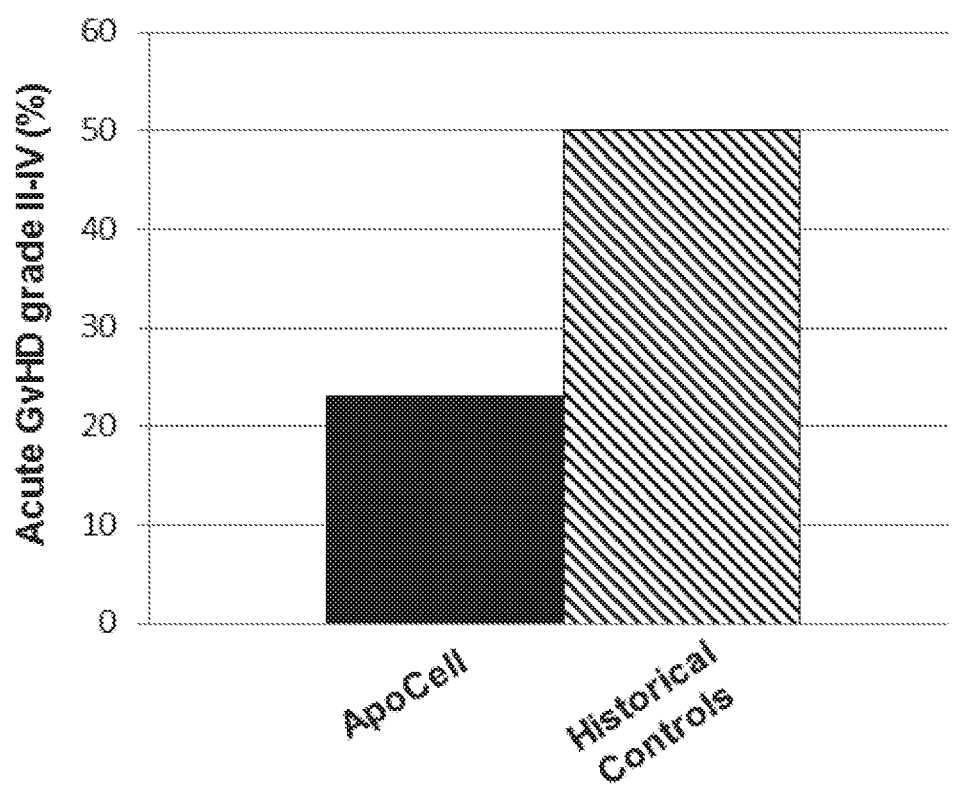
FIG. 4B is a histogram illustrating the reduced incidence of grade II-IV GVHD in 13 transplanted recipients receiving a single infusion of apoptotic cell preparation (35-210×10$^6$ apoptotic cells; ApoCell) as compared to 25 matched historical controls from hospital records (Historical Controls).

Infusion of Allogeneic Apoptotic Cells Reduces High Grade GVHD in Patients Undergoing Myeloablative Allogeneic Bone Marrow Transplantation Acute GVHD was assessed through day 100 of the study in 12 out of 13 patients and in one patient in the second treatment group through day 87. All were included in the day-100 cumulative incidence. The day-100 cumulative incidences of grades II through IV and III through IV acute GVHD (aGVHD) for all patients were 23.1% and 15.4%, respectively (FIG. 4). Acute GVHD was assessed through day 180 of the study in 10 out of 11 patients. The median times to onset of grades II through IV and III through IV acute GVHD were 31 days (range, 31-44 days) and 47 days (range, 31-62 days), respectively. No patient developed acute GVHD beyond day 100 after transplantation. Ten of 11 patients were assessed for aGVHD at day 180. One of 10 patients (10%) was with persistent skin aGVHD grade 1 with overall severity grade 1 on day 180 of the study. Of note is that no high grade GVHD (grade II-IV) was documented in two cohorts treated with the highest dose of ApoCell (FIG. 4A). GVHD grade II-IV incidence in transplanted patients receiving single infusion of apoptotic cell preparation was significantly low (7.7% of 13 subjects, FIG. 4B; column 1) in comparison to historical control from hospital records (50% of 25 subjects, FIG. 4B; column 2) and reports from the literature (71%, data not shown; Gooley, ibid.)

In every successful treatment that potentially avoids high grade aGVHD, there arises a question regarding the possible loss of graft-versus-leukemia (GVL) effect that was found to correlate to the severity of GVHD (Horowitz M M Blood 1990). In the present study the relapse rate was 7.7% at 100 days and 30.8% at 180 days. The relapse rate at 100 days is not different from the reported relapse rate of similar patients undergoing alloBMT. The rate of 30% relapse by day 180 may be considered borderline high, however, 75% of relapse incidences were patients with ALL (3 of 4 patients that tend to relapse in high rates of 70% at similar age group). Furthermore, although, the grade II-IV GVHD was decreased to 0 in the two higher doses, grade I aGVHD was increased to 50% in the same cohorts, indicating that ApoCell treatment, as a physiological modality, reduces high grade GVHD rather than abolishing it.

Chronic GVHD (cGVHD) was assessed from day 100 till day 180 of the study. Ten of 11 patients were assessed for cGVHD at day 180. Five of 10 patients (50%) had mild cGVHD involving skin (four patients) and conjunctiva (one patient).

Example 2 demonstrates that the incidences of acute grades II through IV and grades III through IV GVHD were very low (23% and 15% respectively) in comparison to historical control and reports from the literature (Gooley, ibid.) 71% grade II-IV and 14% grade III-IV in last decade). Remarkably, in the two higher dosages there was 0% aGVHD grade II-IV, suggesting a remarkably effective prophylactic treatment.

Example 3

Reduced Incidence of Hepatotoxicity in Transplant Patients Receiving a Single Dose of Apoptotic Cells The number of transplant patients developing hepatotoxicity in all four of cohorts I-IV (n=13; column 2), receiving from 35-210×10$^6$ apoptotic cells was compared with that of matched controls from hospital records (n=18), and with the long-term documented transplant patients (n=1148; Gooley et al, ibid.).

Figure 5A:
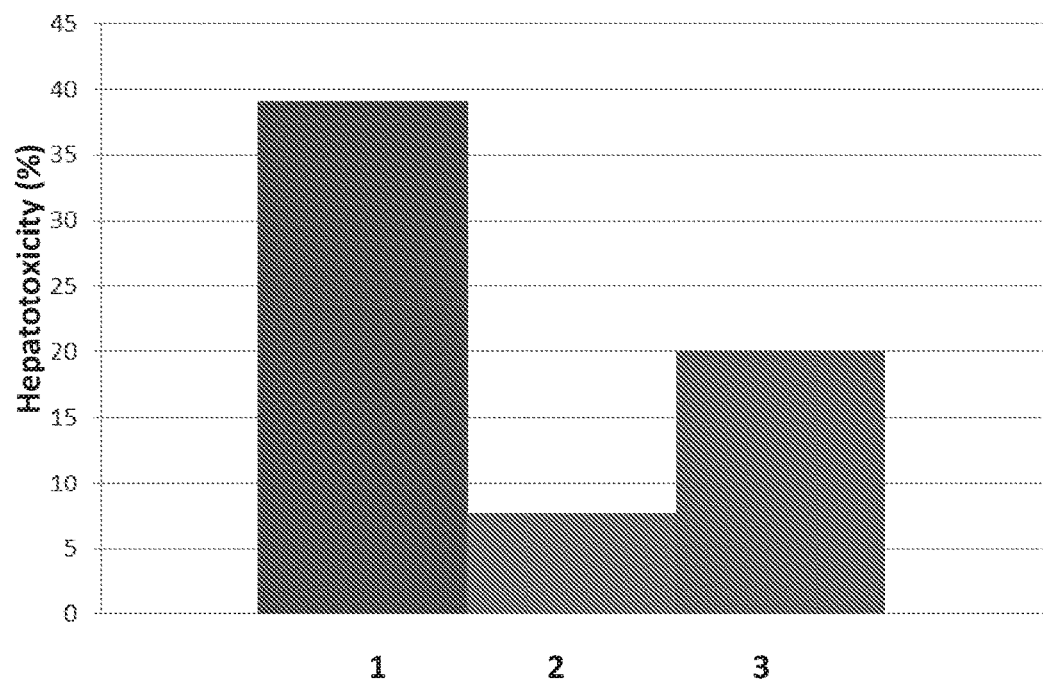
FIG. 5A is a histogram illustrating the reduced incidence of hepatotoxicity in transplant patients receiving a single dose of apoptotic cells. The percentage of transplant patients developing hepatotoxicity in all four of cohorts I-IV (n=13; column 2), receiving from 35-210×10$^6$ apoptotic cells preparations was compared with that of matched controls from hospital records (n=18; column 1), and with the long-term documented transplant patients (n=1148; column 3) (Gooley et al, ibid.).
Figure 5B:
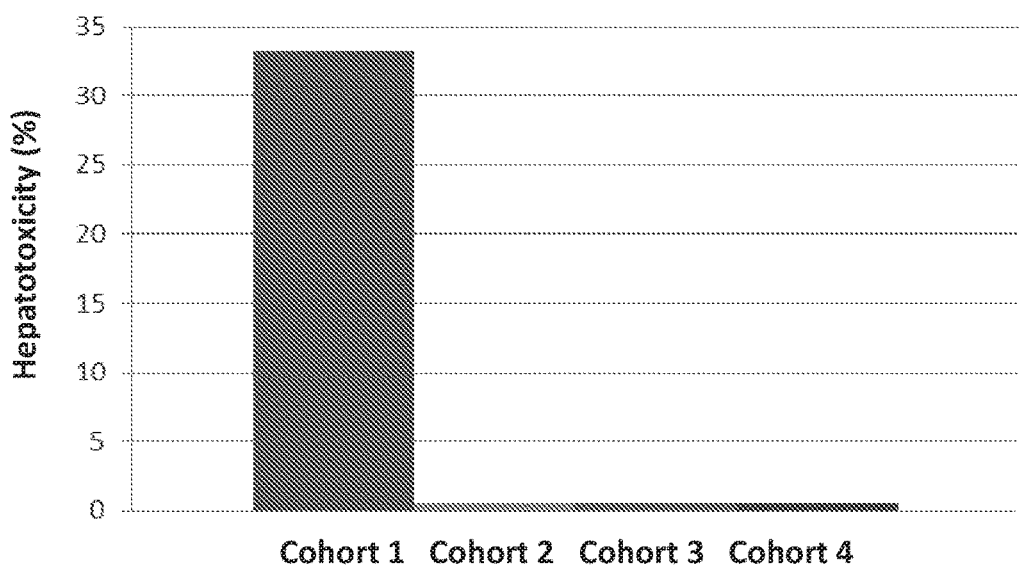
FIG. 5B is a histogram illustrating the reduced incidence of hepatotoxicity in transplant patients receiving a single dose of apoptotic cells. The incidence of hepatotoxicity in transplant patients in each of four cohorts I (35×10$^6$ apoptotic cells) (column 1), II (70×10$^6$ apoptotic cells) (column 2), III (140×10$^6$ apoptotic cells) (column 3) and IV (210×10$^6$ apoptotic cells) (column 4) receiving apoptotic cells.

Only one patient in the treatment group developed hepatotoxicity (7.7%; FIG. 5A, column 2), compared to 39% (FIG. 5A, column 1) of the matched historical controls and 20% (FIG. 5A, column 3) in the long-term documented transplant patients. Of note, no hepatic toxicity of GVHD was documented in the three higher dosages treatment groups (cohorts II-IV) treated with the apoptotic cell preparation of the invention (FIG. 5B), compared to 39% observed among the matched historical controls.

Example 4

Validation of the Clinical Studies Using Acute GVHD (aGVHD) Plasma Biomarkers Plasma biomarkers that were reported as aGVHD discriminators or aGVHD predictors were examined in order to further validate the clinical results. A panel of four plasma biomarkers IL-2Ra, TNFR1, IL-8 and HGF were proposed as markers that can help optimally discriminate patients with and without aGVHD and can confirm the diagnosis of GVHD in patients at the onset of clinical symptoms of GVHD and can also provide prognostic information for survival independent of GVHD severity.

Figure 6A:
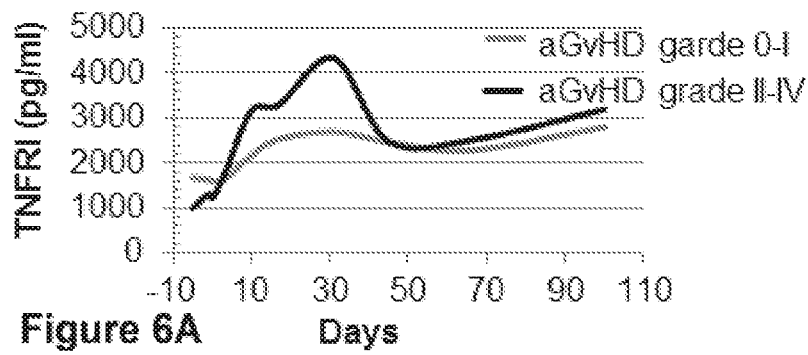
FIGS. 6A-H illustrate the kinetics of plasma biomarkers (TNFR1, IL-2Ra, IL-15, IL-1β, HGF, IL-8, IL-7, and IL-6) in post-transplant patients receiving a single dose of apoptotic cells.
Figure 6B:
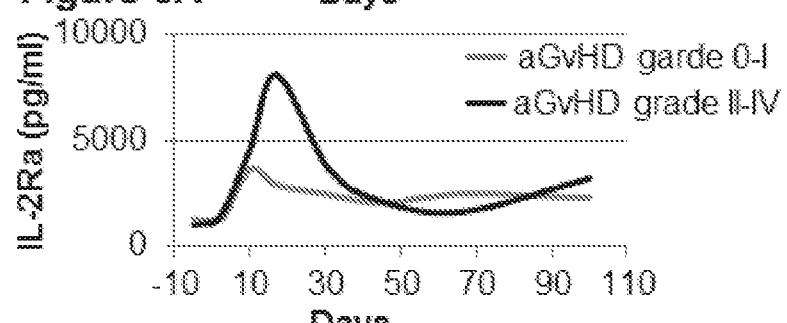

First, plasma levels of TNFR1, IL-2Ra, IL-8 and serum levels of HGF were evaluated. As shown in FIGS. 6A,B,E and F, clearly higher levels were found in aGVHD grade II-IV group in comparison to aGVHD grade 0-I group. Median TNFRI level in aGVHD grade 0-I group at day +10, +17, and +31 were 2172 pg/ml, 2530 pg/ml, and 2698 pg/ml, respectively.

However, in aGVHD grade II-IV group, TNFRI median levels were 3171 pg/ml, 3301 pg/ml and 4342 pg/ml respectively. Similarly, IL-2Ra median levels in aGVHD grade 0-I group were 3650 pg/ml, 2916 pg/ml, and 2455 pg/ml, respectively, in comparison to 4601 pg/ml, 8102 pg/ml and 3624 pg/ml in aGVHD grade II-IV group, respectively. Once again, HGF median levels in aGVHD 0-I group at day +17, +31, and +45 were 1517 pg/ml, 1464 pg/ml, and 1873 pg/ml, respectively in comparison to 2418 pg/ml, 3264 pg/ml and 2326 pg/ml in aGVHD grade II-IV group, respectively. Finally, median levels of IL-8 in aGVHD grade 0-I group at day +10, day 17 and +31 were 48.3 pg/ml, 22.3 pg/ml and 37.1 pg/ml, respectively, in comparison to 90.8 pg/ml, 41.9 pg/ml and 61.8 pg/ml in aGVHD grade II-IV group, respectively (FIGS. 6 A,B,E and F).

As some publications prefer using median concentration ratio rather than cytokine concentration, especially with TNFRI levels (Ferrara J L Best practice & research clinical haematology 2007, Choi S W et al Transplantation 2012). However, when the inventors used TNFRI ratio or other cytokine ratios our results did not change (data not shown).

Figure 6C:
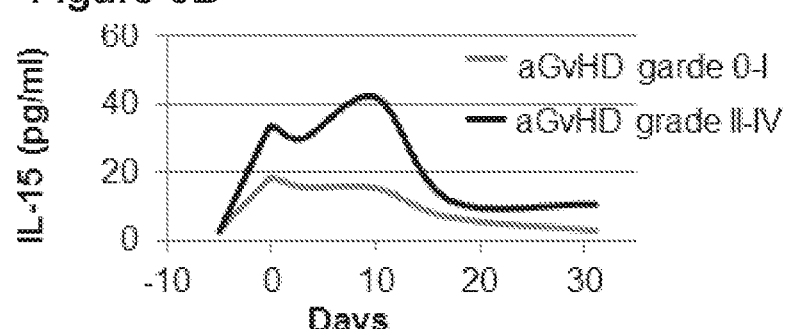
Figure 6D:
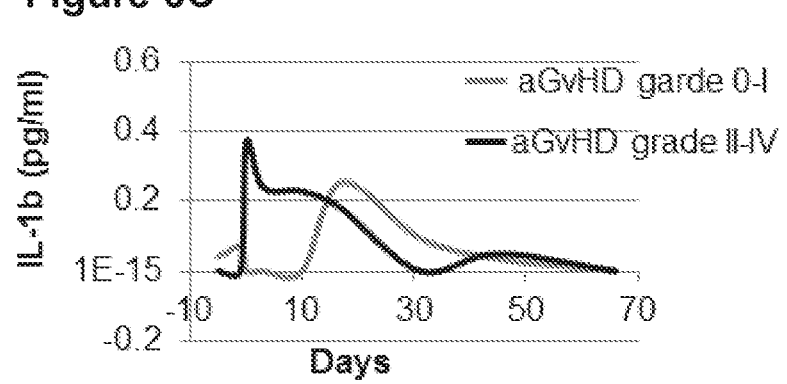
Figure 6E:
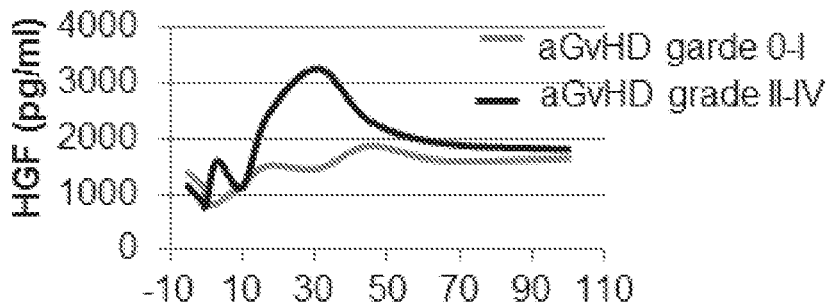
Figure 6F:
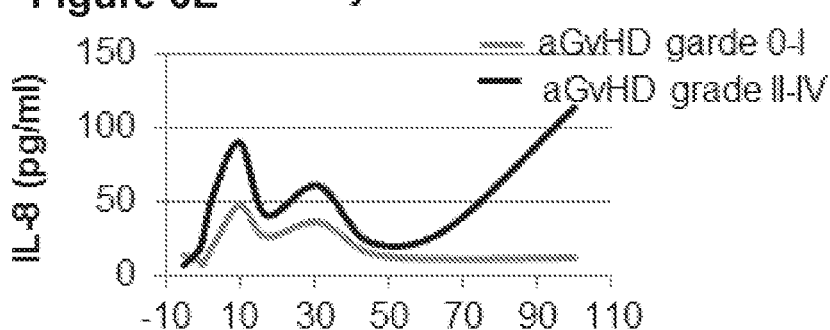
Figure 6G:
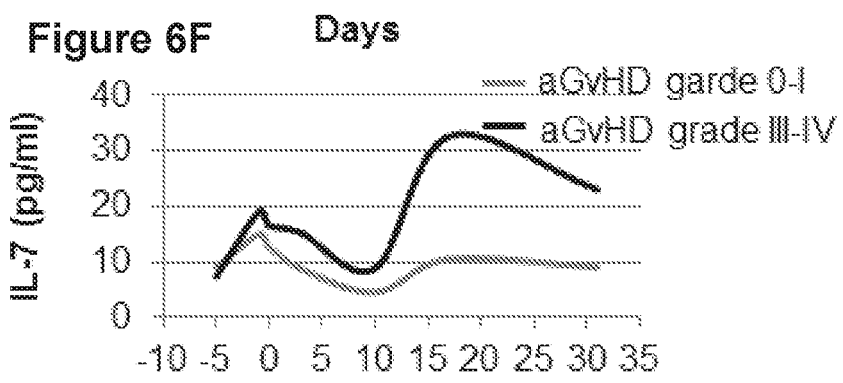
Figure 6H:
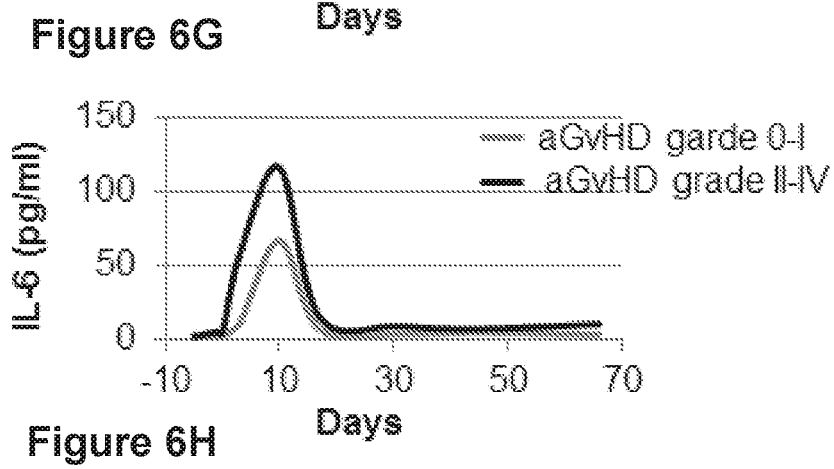

Two additional cytokines, IL-15 and IL-7 were reported to correlate to aGVHD. As shown in FIG. 6C, IL-15 median plasma levels in our study were significantly higher in aGVHD grade II-IV group 33.5 pg/ml, 30 pg/ml, a 42 pg/ml and 12 pg/ml, at days 0, +3, +10, +17, respectively, in comparison to aGVHD grade 0-I group; 18.6 pg/ml, 15.7 pg/ml, 15.5 pg/ml, and 7.0 pg/ml, respectively.

IL-7 was also elevated in high grade GVHD (FIG. 6G), although the main elevation was seen in grade III-IV with 8.9 pg/ml, 32.6 pg/ml and 23.0 pg/ml at days +10, +17 and +31, respectively, versus, 4.5/ml, 10.5 pg/ml and 9.0 pg/ml, respectively in aGVHD 0-I.

As cytokine control, IL-6 and IL-1b were measured. As expected, other cytokines showed elevations that did not distinguish between GVHD grades.

Example 4 demonstrates plasma biomarkers supporting the clinical data presented herein. Although published data is lacking regarding what are the best biomarkers, plasma levels of six different biomarkers: TNFRI, IL-2Ra, HGF, IL-8, IL-15 and IL-7, distinguished well between high to low grade or no-GVHD. Additional two control cytokines (IL-1b and IL-6) further emphasized the specificity of findings.

Example 5

The Ameliorative Effect of the Apoptotic Cell Composition on Inflammatory Colitis The therapeutic effect of a single infusion of the apoptotic cells in ameliorating colitis was examined in two IBD models: adoptive T cell transfer (TCT) of naïve CD4 cells and dextran sulfate sodium (DSS)-induced colitis.

First, CD45RB$^{high}$ Naïve T cells were harvested and sorted from WT C57BL/6 mice and adoptive transferred into immune deficient mice lacking the RAG enzyme. Non naïve (CD45RB$^{low}$) T cells were used as a control for transferred cells. A composition comprising early apoptotic cells within 150 μl of PBS was administered to the mice on the day of the T-cell transfer, while 150 μl of PBS were used as a control.

Figure 7A:
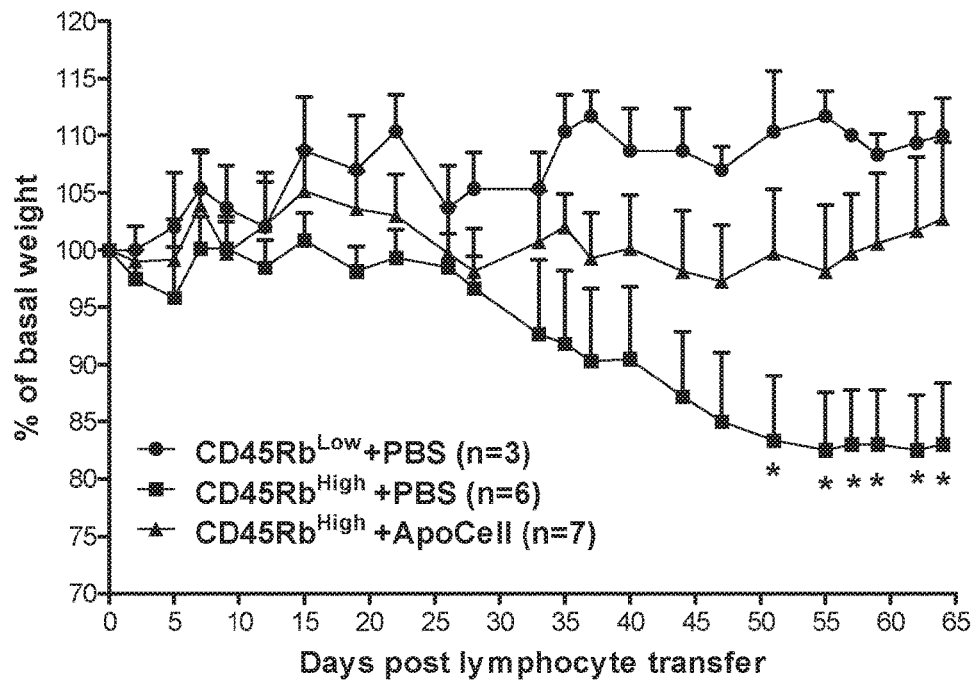
FIGS. 7A-C are graphs illustrating the protective effect of the apoptotic cell preparation from T cell transfer-induced colitis. Rag1−/− mice received WT CD4$^+$CD45RB$^{low}$ (filled circles), or CD4$^+$CD45RB$^{high}$ T cells alone (filled squares) or in combination with apoptotic cells (filled triangles). (7A) Mean weight of indicated animal number per group (*p<0.05, t-test). (7B) IBD Clinical Score. Numbers inside boxes indicate the mean score of each parameter with error bar (*p<0.02, t-test). Data is presented as mean±SEM of 3 independent experiments. Weight change and stool consistency were monitored daily. Of note, no hematochezia was detected in either mice group. (7C) Illustrates increased T regulatory cells in mesenteric lymph nodes following ApoCell treatment compared to non-treated animals and control lymph nodes (popliteal).
Figure 7B:
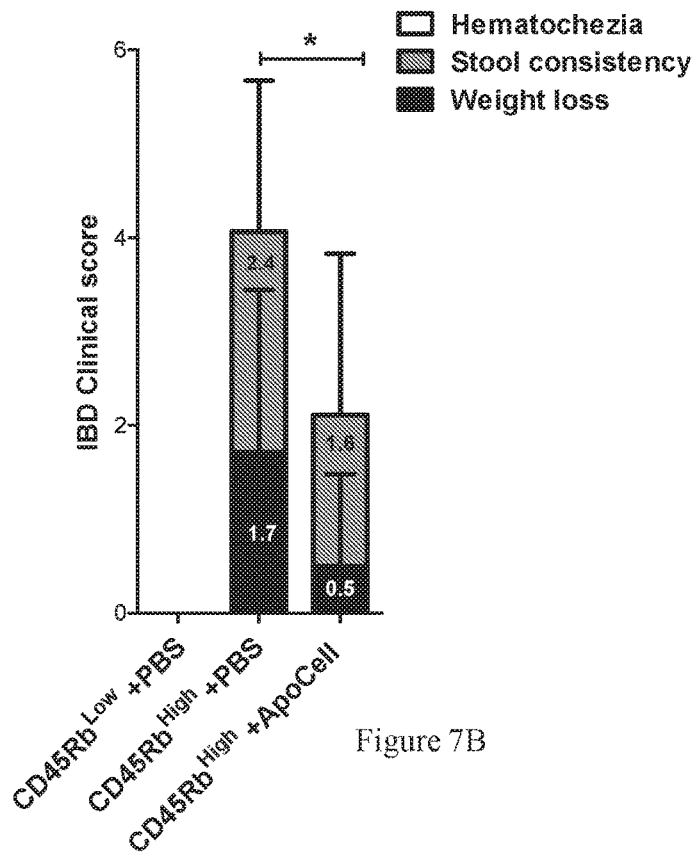
Figure 7C:
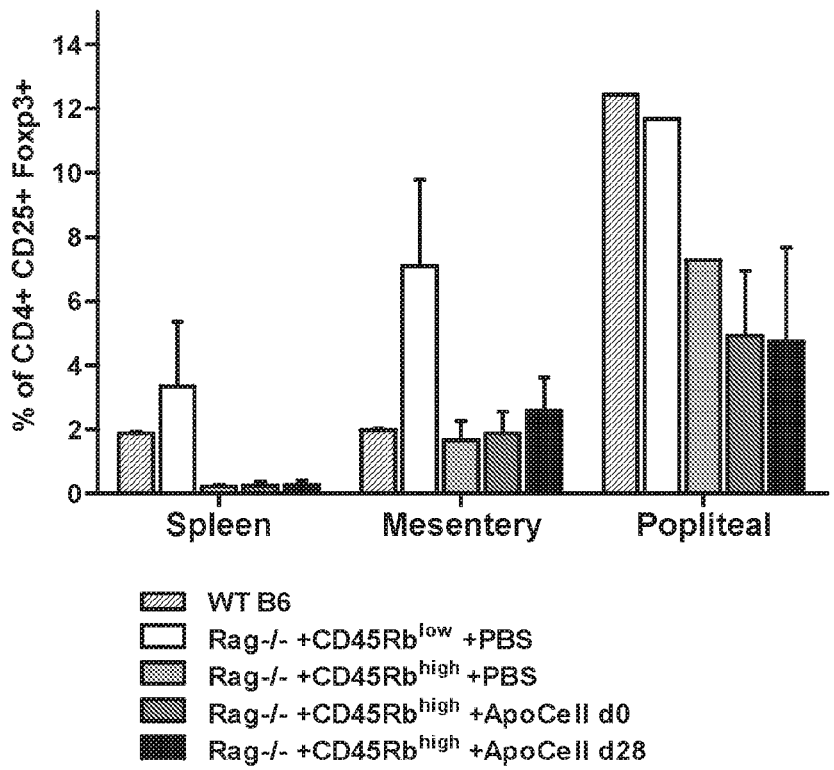

Four weeks later, mice in the PBS treated group started to develop clinical signs of IBD, namely weight loss and pasty stool discharges. However, in the group treated with apoptotic cell composition, no clinical deterioration was observed. The CD45RB$^{high}$ mice group lost 17% of their initial body weight whereas the apoptotic cell treated group gained weight (FIG. 7A, p<0.03). Similarly, the overall clinical score was significantly reduced in the group treated with apoptotic cells compared to non-treated group (FIG. 7B, p<0.02). Elevation in mesenteric T-regulatory cells in the treated group was also demonstrated in mesenteric lymph nodes (FIG. 7C).

Example 6

DSS Induces Caspase-1-Dependent Pro-IL-1β Processing Via NLRP3 Inflammasome

Enhanced production of IL-1β has been previously shown to be detected upon exposure of murine macrophages to DSS, and more recently was shown in vitro and in vivo to be NLRP3 inflammasome-dependent.

Figure 8:
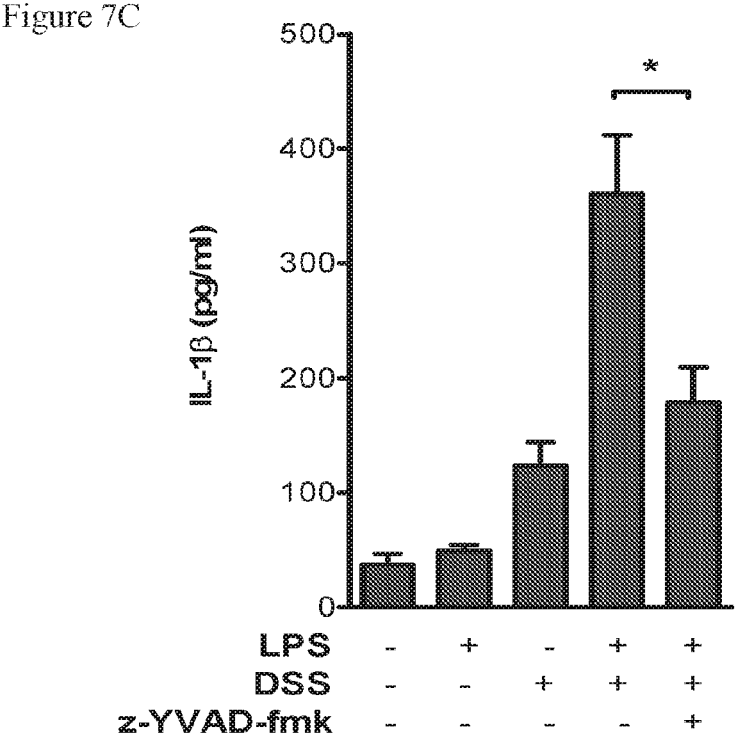
FIG. 8 is a bar graph depicting dextran sodium sulfate (DSS) induced caspase-1-mediated IL-1β release from murine macrophages. Murine primary resident peritoneal macrophages (pMΦ) were either left untreated, or treated with the depicted combinations of: lipopolysaccharide (LPS), 3% DSS and z-YVAD-fmk (10 μM). IL-1β release was determined in the supernatant by ELISA. Shown are representative data as means±SEM of 3 independent experiments done in triplicate (*p<0.02, t test).
Figure 9A:
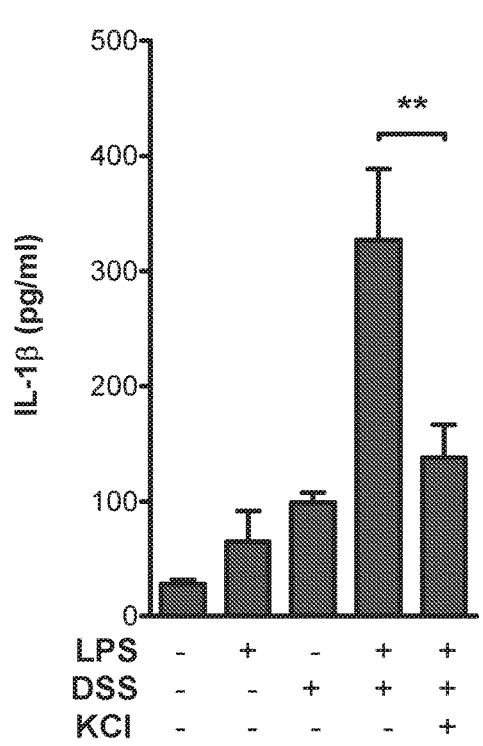
Figure 9B:
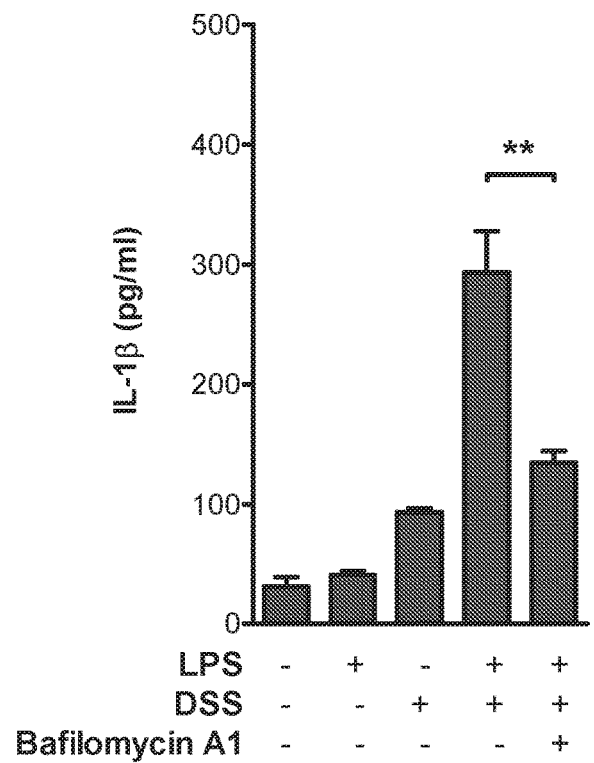

In order to investigate the possible role of apoptotic cells in negative regulation of the inflammasome, murine macrophages were generated and exposed to DSS. In agreement with previous observations, DSS was found to induce IL-1β release from murine macrophages, as can be seen in FIG. 8. A combination of Toll Like Receptor (TLR) triggering with LPS and inflammasome triggering with DSS led to a marked IL-1β secretion. As can be seen in FIG. 8, inhibition of caspase-1 by the specific inhibitor z-YVAD-fmk peptide led to an almost complete inhibition of IL-1β release (p<0.05, unpaired t test), demonstrating the role of caspase-1 in DSS-mediated IL-1β release. Activation of the NLRP3 inflammasome is $K^+$ efflux-dependent, lysosomal-dependent, and ROS-dependent. Indeed, blocking $K^+$ efflux with high concentrations of KCl inhibited DSS-mediated IL-1β release (FIG. 9A, p<0.05, unpaired t test) Similarly, blocking lysosomal acidification with bafilomycin, an inhibitor of vacuolar ATPase, inhibited IL-1β secretion (FIG. 9B, p=0.05, unpaired t test). Finally, inhibition of ROS generation by N-acetyl-L-cysteine (NAC) significantly inhibited IL-1β secretion (FIG. 9C, p<0.05, unpaired t test).

To further support the finding that DSS-mediated IL-1β secretion is caspase-1 and NLRP3 activation-dependent, wild-type and NLRP3-deficient mice were co-housed and macrophages were extracted from the mice and exposed to DSS. As can be seen in FIG. 9D, DSS-induced IL-1β secretion was significantly reduced in macrophages extracted from NLRP3-deficient mice (p<0.02, t test).

Example 7

Treatment with the Apoptotic Cell Composition Shows an Anti-Inflammatory Effect in a Dextran-Sulfate-Sodium (DSS) Model The effect of treatment using the apoptotic cell composition was further examined in a DSS-mediated intestinal inflammation model in vivo by administering 3% DSS for a period of 8-9 days to Balb/c mice within their drinking water Inflammatory bowel disease (IBD) score parameters, including body weight, the presence of latent or gross blood per rectum, and stool consistency, were determined daily.

Figure 10A:
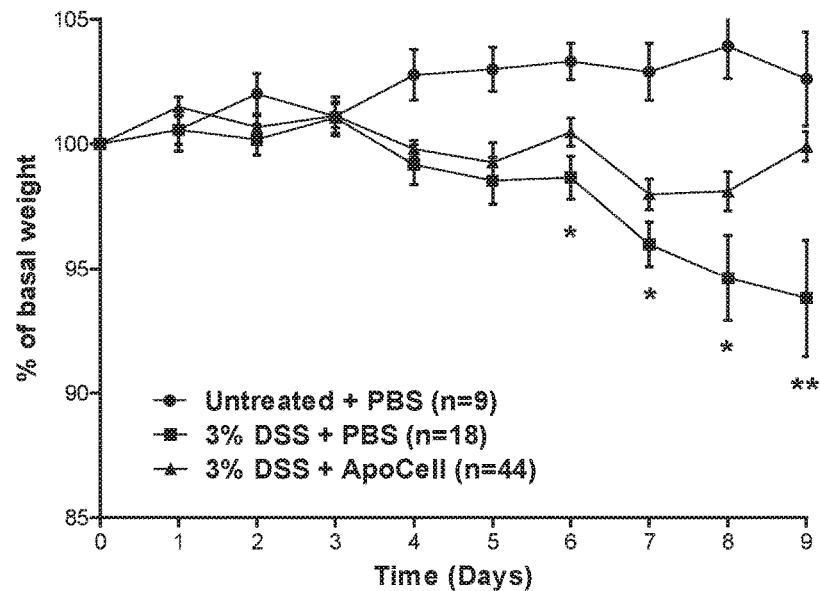
FIGS. 10A-D demonstrate the protective effect of the apoptotic cell preparation from dextran sodium sulfate (DSS)-induced colitis. Balb/c mice were offered distilled water (filled circles), or distilled water with 3% DSS orally ad libitum with treatment of PBS (filled squares) or apoptotic cell (filled triangles). (10A) Mean weight of indicated animal number per group. (10B) IBD Clinical Score. Numbers inside boxes indicate the mean score of each parameter with error bar (*p<0.001, t-test). Data is presented as mean±SEM of 3 independent experiments. Weight change, hematochezia and stool consistency were monitored daily. (10C) Macroscopic changes of colon and spleen in DSS-treated mice. Photographs of the dissected large intestines and spleens of four mice treated with 3% DSS without- (DSS+PBS) or with apoptotic cell treatment (DSS+ApoCell). (10D) IL-1β cytokine level in colonic homogenate from DSS-treated mice. Levels of IL-1β were analyzed by ELISA. Data is presented as mean±SEM, 3 mice per group (*p<0.01, **p<0.001, one way ANOVA).
Figure 10B:
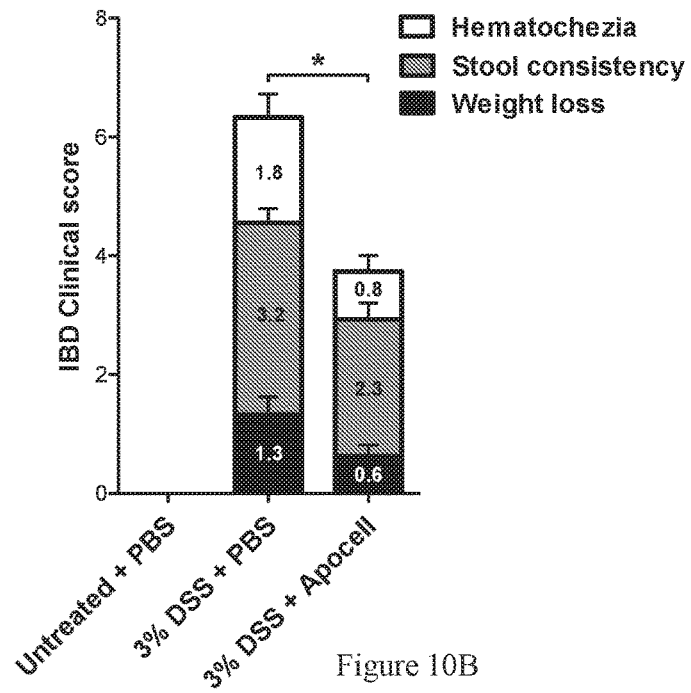
Figure 10C:
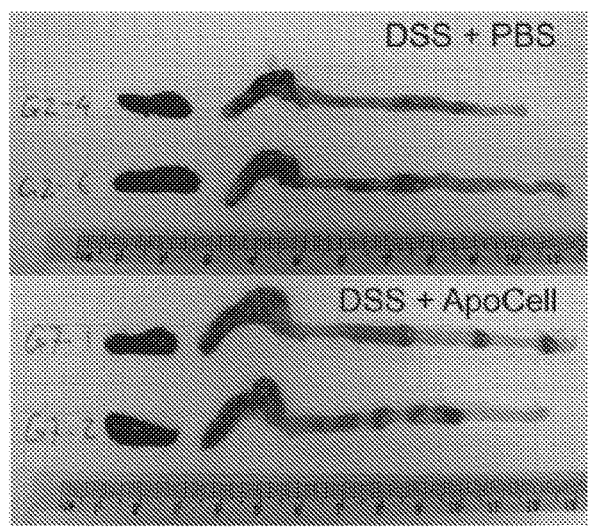

Mice treated with apoptotic cells in addition to DSS showed significantly less body weight loss starting from day 6, as compared to mice treated only with DSS (FIG. 10A, p<0.05 and 0.001, t test). Clinical score analysis revealed significantly less severe colitis in mice treated with apoptotic cells, in all parameters evaluated (FIG. 10B, p<0.01, t test). On macroscopic examination, DSS-treated colons were severely inflamed and hyperemic, and contained less feces due to massive diarrhea. When treated with apoptotic cells, colons were less affected and were longer than colons of mice treated only with DSS (9.4±0.14 cm vs. 8.9±0.2, p<0.05) (FIG. 10C).

Figure 10D:
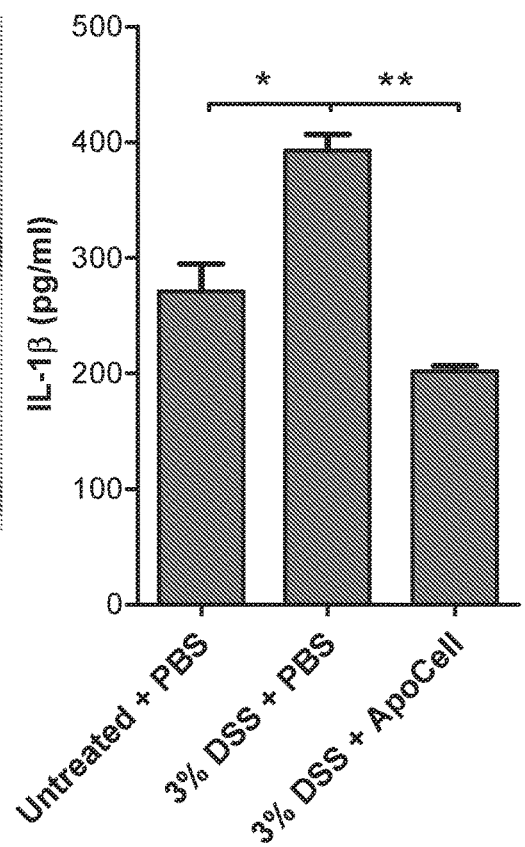

Next, IL-1β levels were measured in colonic homogenates of mice treated with DSS, either with or without treatment with the apoptotic cell composition. After 7 days of DSS intake, IL-1β levels were significantly elevated in colons of mice not treated with the apoptotic cell composition (FIG. 10D, p<0.02, t test). However, in mice treated with a single apoptotic cell injection prior to DSS intake, a similar elevation was not observed.

Figure 11B:
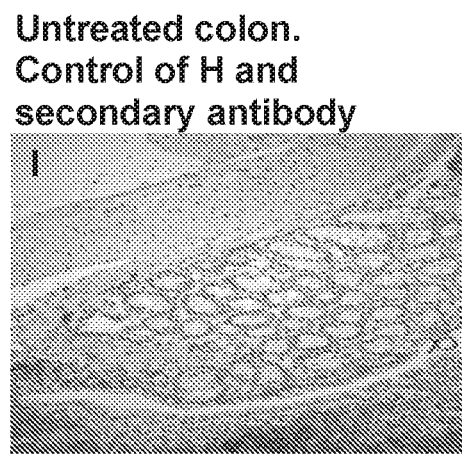
FIG. 11B demonstrates neutrophil accumulation inhibition in inflamed colon treated by the apoptotic cell preparation. Mouse colon tissue sections were stained by immunohistochemistry assay using a rabbit monoclonal antibody against mouse myeloperoxidase (MPO). After immunostaining, slides were counterstained by hematoxylin. Images show the MPO stain followed by HRP-anti rabbit secondary antibody. All images are ×200. (11B-I) Staining control. Untreated colon stained with HRP-anti rabbit secondary antibody only, without anti-MPO. (11B-II) Normal colon control. MPO-stained neutrophils in untreated colon (0% DSS+PBS). (11B-III) DSS treatment. MPO-stained neutrophils in 3% DSS treated colon (3% DSS+PBS). (11B-IV) Apoptotic cell & DSS treatment. MPO-stained neutrophils in 3% DSS-treated colon with apoptotic cell infusion (3% DSS+ApoCell).
Figure 11B:
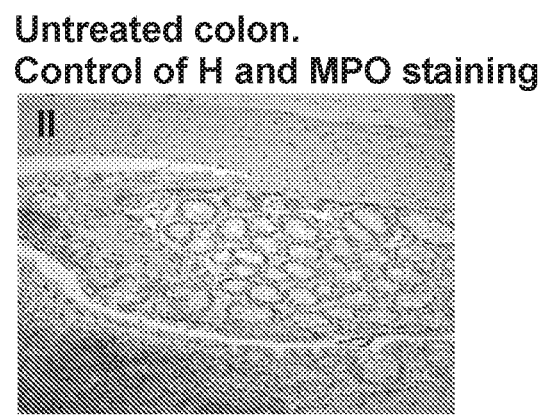
Figure 11B:
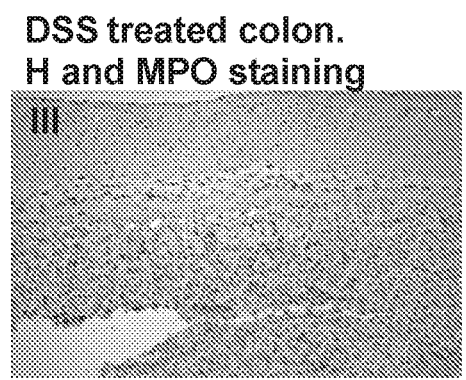
Figure 11B:
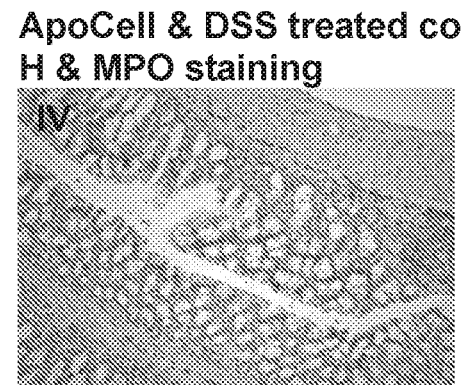

In order to further establish the exhibited observations, histological and immunohistochemical analysis of colonic tissue were obtained on day 9 following DSS intake. Biopsies showed significantly less severe mucosal infiltration by inflammatory cells and reduced tissue damage in mice treated with apoptotic cells, translating into a significantly improved histological colitis severity score (FIG. 11A I-III, p<0.05, t test). This analysis was performed by a pathologist blinded to the different groups. Since IL-1β is known to induce accumulation of neutrophils at inflammation sites, the range of neutrophils in colon inflammation was evaluated. Neutrophil infiltration was markedly higher in colon tissue of mice which did not receive apoptotic cell treatment. To further illustrate the dramatic reduction in neutrophil infiltration with apoptotic cell treatment, myeloperoxidase (MPO) staining was combined with hematoxylin staining (FIG. 11B). Indeed, DSS-treated mice showed a dramatic increase in MPO-stained neutrophils in the colon, while a single treatment with apoptotic cells markedly reduced MPO-stained neutrophil accumulation.

Figure 12:
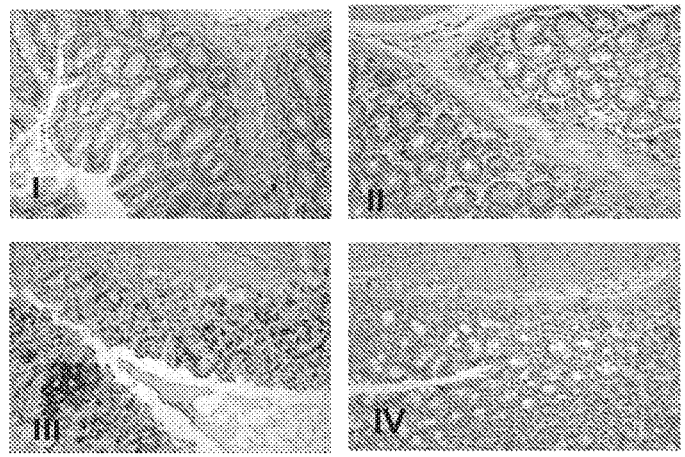
FIG. 12 shows cyclooxygenase-2 (COX-2) inhibition in DSS-induced colitis treated by the apoptotic cell preparation. Mouse colon tissue sections were stained by immunohistochemistry assay using an antibody against mouse COX-2. After immunostaining, slides were counterstained by hematoxylin. All images are ×200. (I) Staining control. Untreated colon stained with HRP-anti rabbit secondary antibody only without anti COX-2. (II) COX-2 expression in untreated colon (0% DSS+PBS). (III) COX-2 expression in 3% DSS treated colon (3% DSS+PBS). (IV) COX-2 expression in 3% DSS-treated colon with apoptotic cell infusion (3% DSS+ApoCell).

Cyclooxygenases (COXs) catalyze a key step in the formation of pro-inflammatory prostaglandins and have been shown to be induced by IL-1β. The main product of the Cox2 cascade is PGE2, which is the key mediator in the acute inflammatory response. Indeed, Cox2 immunostaining showed a dramatic elevation in the number of positive cells in DSS-treated colons compared to non-treated colons (FIG. 12). When apoptotic cell treatment was applied, a marked reduction was observed.

Example 8

In Vivo NF-κB Inhibition by Apoptotic Cells in DSS-Induced Colitis

Figure 13:
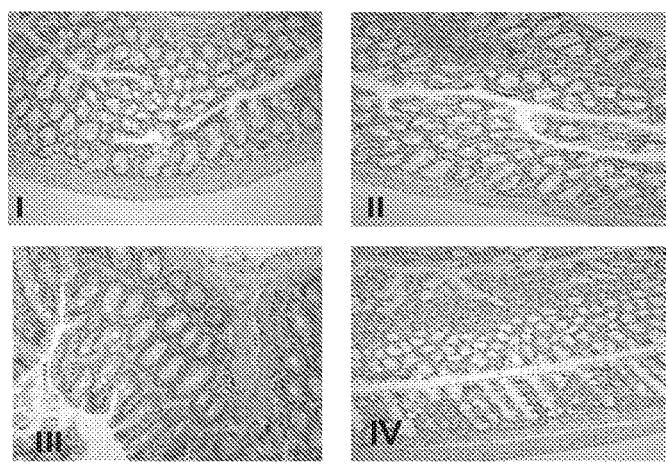
FIG. 13 shows Iκ-Bα inhibition in DSS-induced colitis treated by the apoptotic cell preparation. Mouse colon tissue sections were stained by immunohistochemistry assay using an antibody against mouse phospho-Iκ-Bα (pκ-Bα). After immunostaining, the slides were counterstained by hematoxylin. Images show pκ-Bα. All images are ×200. (I) Untreated colon stained with HRP anti-mouse secondary antibody only, without anti-pIκ-Bα. (II) pIκ-Bα staining in untreated colon (0% DSS+PBS). (III) pκ-Bα expression in 3% DSS-treated colon (3% DSS+PBS). (IV) pIκ-Bα expression in 3% DSS treated colon with apoptotic cell infusion (3% DSS+ApoCell).
Figure 14:
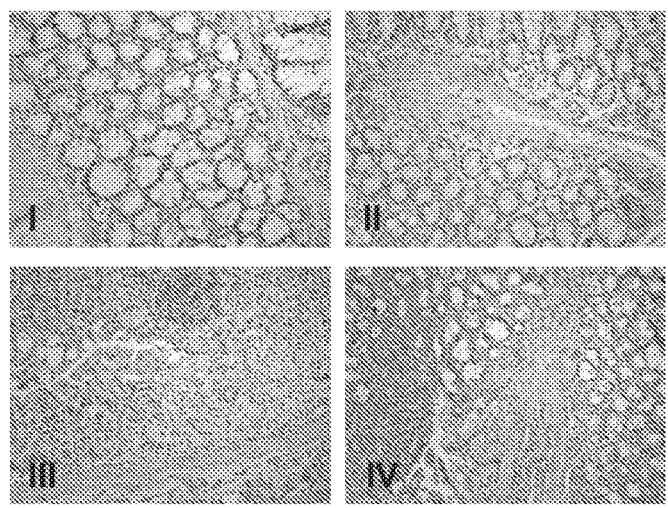
FIG. 14 shows NF-κB inhibition in DSS-induced colitis treated by the apoptotic cell preparation. Mouse colon tissue sections were stained by immunohistochemistry assay using an antibody against mouse phospho-NF-κB (pNF-κB) p65. After immunostaining, slides were counterstained by hematoxylin. Images show pNF-κB p65 staining. All images are ×200. (I) Untreated colon stained with HRP-anti rabbit secondary antibody only, without anti NF-κB. (II) pNF-κB p65 staining in untreated colon (0% DSS+PBS). (III) pNF-κB p65 expression in 3% DSS-treated colon (3% DSS+PBS). (IV) pNF-κB p65 expression in 3% DSS treated colon with apoptotic cell infusion (3% DSS+ApoCell).

NF-κB is normally sequestered in the cytoplasm by means of association with an inhibitory protein, IκBα. Activation of NF-κB involves stimulation of the IKK complex, which phosphorylates IκBα, triggering its degradation and the nuclear translocation of active NF-κB. To examine NF-κB signaling, the phosphorylation of IκBα in colonic tissue from mice with DSS-induced colitis was examined and compared to mice exposed to DSS following treatment with apoptotic cells. An appreciably higher number of pIκBα-positive cells were observed in colon treated solely with DSS compared with colon that was also treated with apoptotic cells (FIG. 13). Inhibition of NF-κB signaling was further confirmed by the reduced number of cells that were positive for nuclear phospho-p65 NF-κB, detected by immunostaining (FIG. 14).

Example 9

Apoptotic Cells Inhibit Inflammasome-Induced IL-1β Release from Macrophages

While inhibition of IL-1β release by macrophages exposed to TLR agonists has been demonstrated, it is not known whether they can inhibit secretion upon NLRP3-specific activation. In order to examine the effect of the apoptotic cell composition on inflammasome-induced IL-1β release, isolated macrophages were exposed to lipopolysaccharide (LPS) and DSS with or without earlier interaction with apoptotic cells for two hours.

Figure 15A:
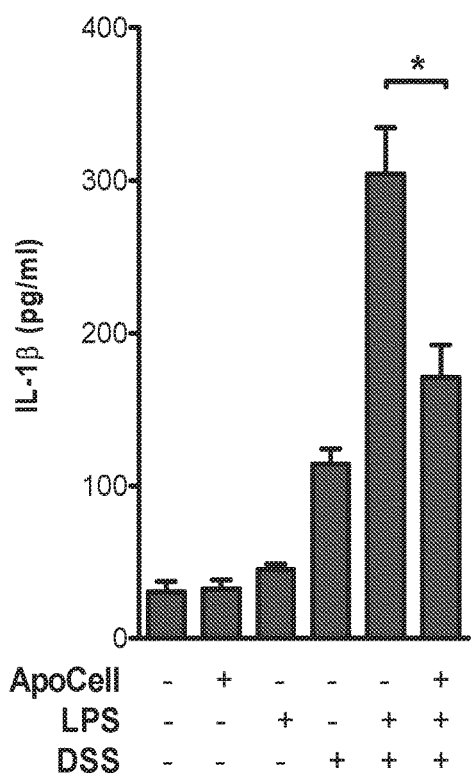
Figure 15B:
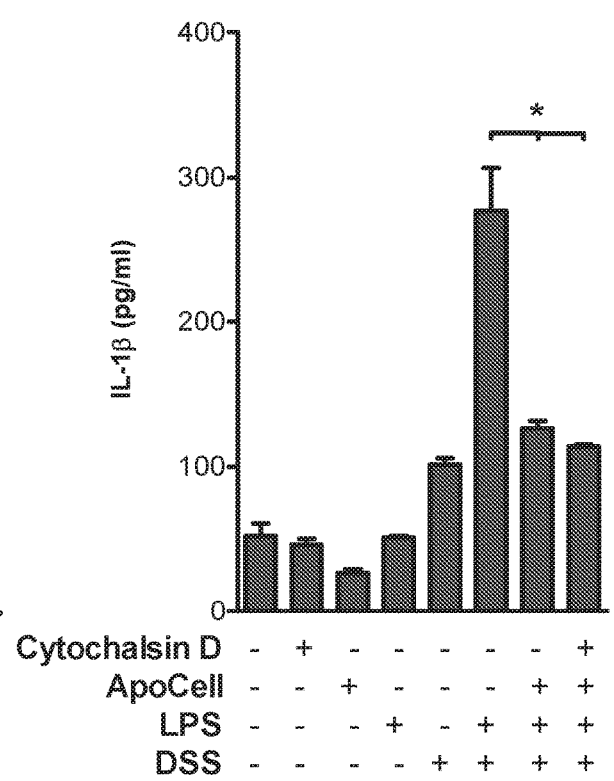

Incubating apoptotic cells with macrophages had no effect on IL-1β secretion in the absence of TLR and inflammasome triggering. However, prior apoptotic cell treatment in the presence of LPS and DSS, significantly inhibited IL-1β secretion from macrophages (FIG. 15A, p<0.01, unpaired t test), with similar inhibition rates as of z-YVAD, KCl, bafilomycin and NAC, suggesting that apoptotic cells negatively signal the inflammasome pathway. To further illustrate the level of apoptotic cells negative signaling cytochalasin D, a pharmacologic agent that inhibits actin polymerization, has been used to prevent and eliminate engulfment. Using this approach, binding of apoptotic cells to macrophages without engulfment was shown to be fully sufficient for inhibition of IL-1β secretion (FIG. 15B, *p<0.01, one way ANOVA).

Given the need for TLR triggering through NF-κB signaling, and the fact that apoptotic cells can inhibit NF-κB, and therefore inhibit IL-1β secretion in the absence of inflammasome inhibition, a set of experiments was initiated to elucidate whether IL-1β secretion is inhibited both at NF-κB and NLRP3 levels by apoptotic cells. Resident peritoneal macrophages (pMΦ) were either incubated with apoptotic cells, washed, and primed with LPS following stimulation with various inflammasome inducers, or were first primed with LPS, allowing accumulation of de novo pro-IL-1β transcription and then treated with apoptotic cells and inducers.

Figure 15E:
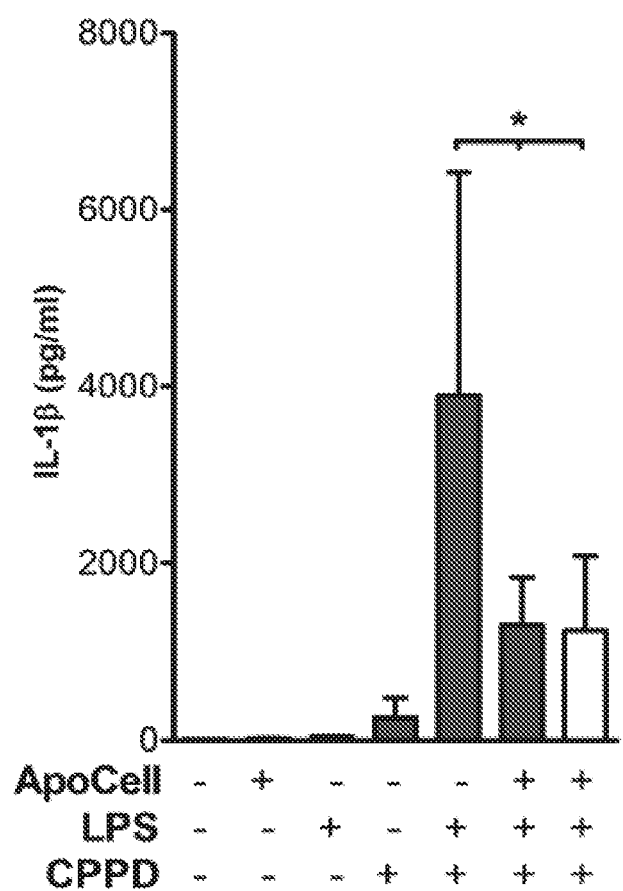

Prior apoptotic cells treatment inhibited the secretion of activated IL-1β at pre-transcription levels, attributing it to NF-κB pathway inhibition. But more importantly, the inhibition effect e.g. IL-1β secretion, was also observed after the accumulation of de novo IL-1β that is, after LPS priming. This inhibition was obtained using three different activators of the NLRP3 inflammasome triggering mechanisms; including nigericin, calcium pirophosphate (CPPD) and monosodium urate (MSU), suggesting a more robust inhibitory effect on NLRP3 inflammasome (FIG. 15C-E, $p<0.001$, one way ANOVA). Inhibition of secretion at post transcription level were also acquire using cytochalasin D, which further support inflammasome negative signaling upon recognition of apoptotic cells without engulfment (data not shown).

The results were further verified by western blot analysis against pro-IL-1β (p35) and cleaved and secreted IL-1β (p17). Macrophages (pMΦ) were incubated either in the presence of apoptotic cells for 2 h followed by LPS priming for 1 h (ApoCell delivered pre-transcription), or first primed with LPS (to promote NF-κB signaling) for 1 h and then incubated with apoptotic cells for 2 h (ApoCell delivered post-transcription). The macrophages were then optionally incubated with an inflammasome inducer—either nigericin (2.5 μM) or calcium pyrophosphate dihydrate 200 μg/mL (CPPD).

Figure 16A:
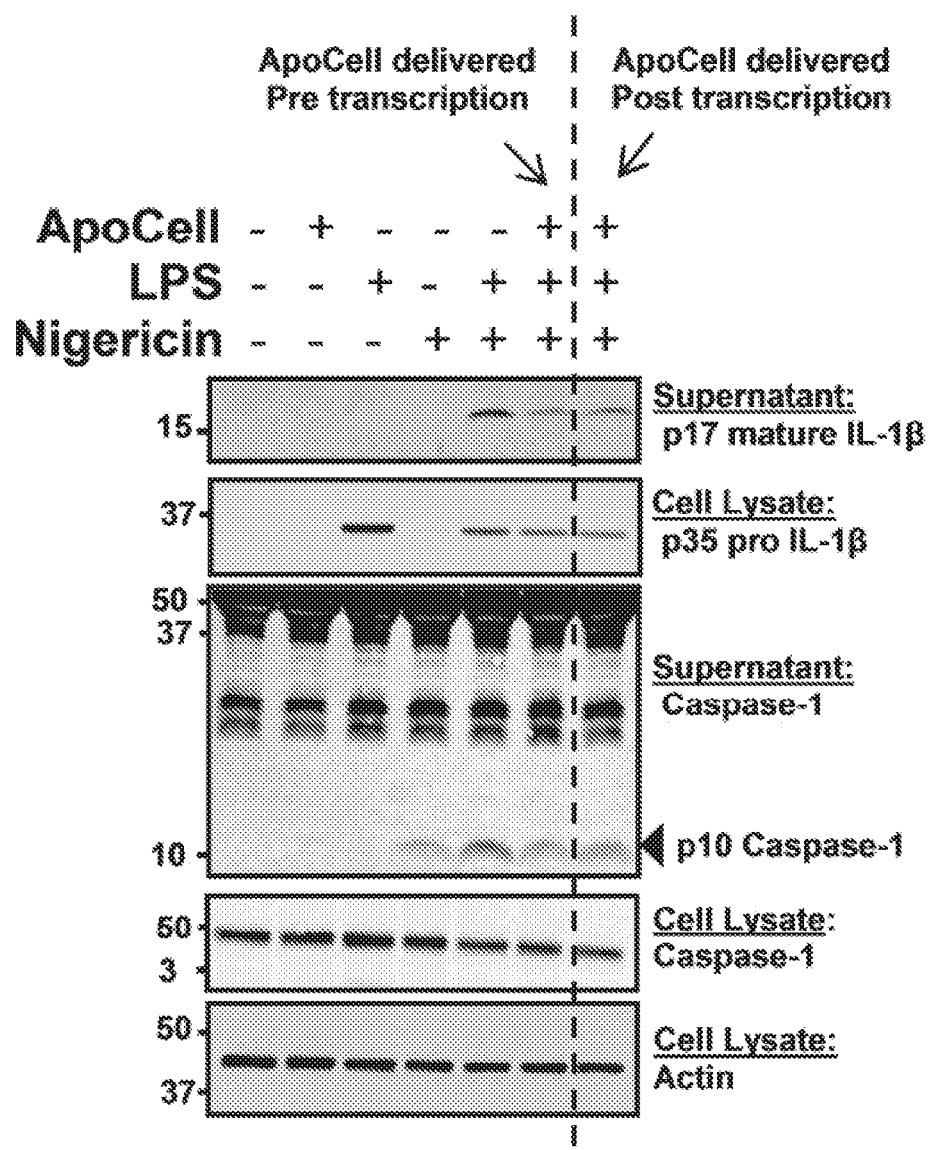
FIGS. 16A-B depict western blot analyses performed on proteins extracted from supernatant and cell lysates of pMΦ cells. Some cells were incubated either in the presence of apoptotic cells for 2 h followed by LPS priming for 1 h (sixth lane from left), or first primed with LPS (to promote NF-κB signaling) for 1 h and then incubated with apoptotic cells for 2 h (seventh lane from left). Following incubation with LPS and/or apoptotic cells, some of the pMΦ were incubated with (16A) nigericin 2.5 μM or (16B) calcium pyrophosphate dihydrate 200 μg/mL (CPPD). An anti-mouse actin served as a loading control. Shown are representative data of two experiments.
Figure 16B:
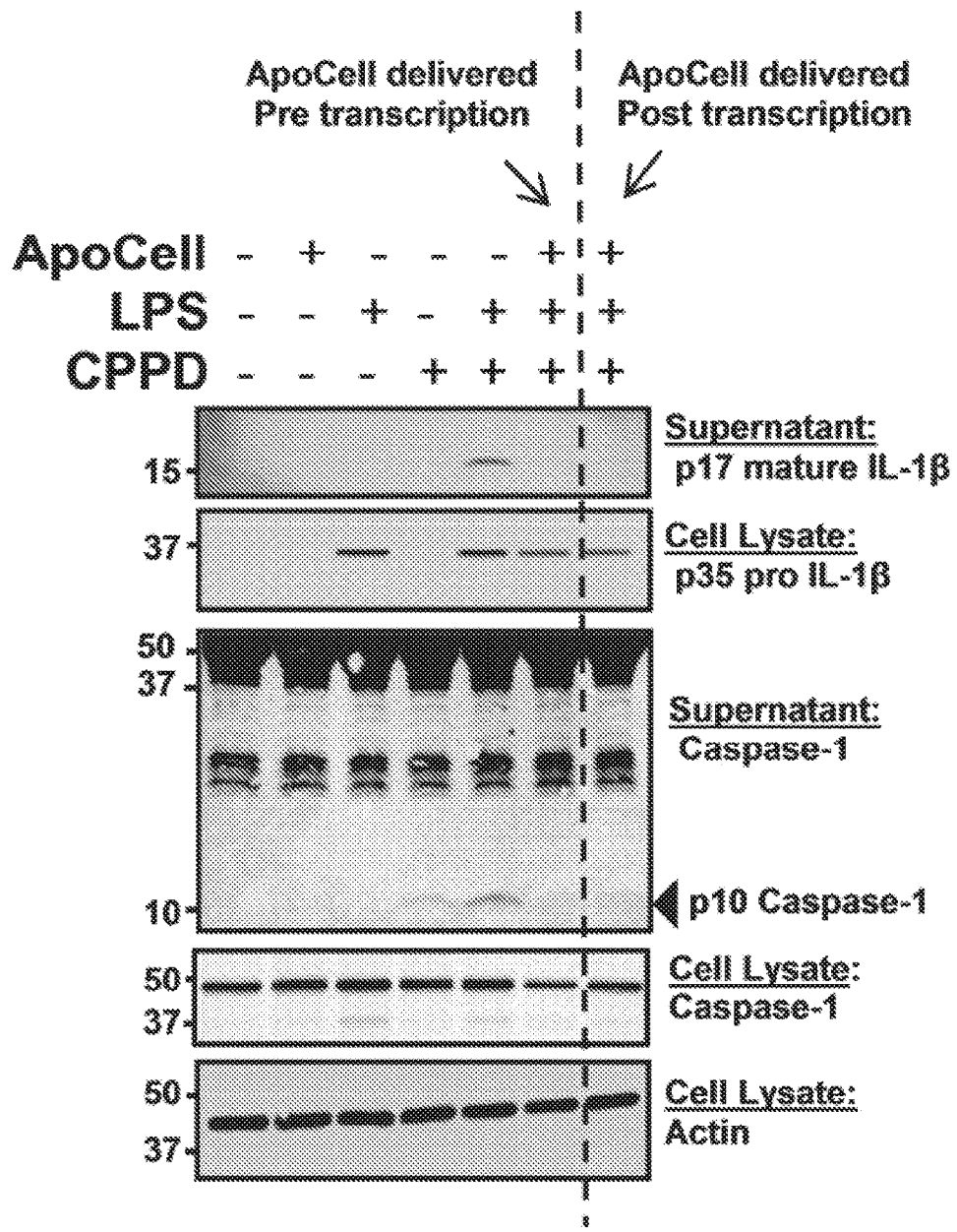

Similarly to ELISA results, a diminished cleaved IL-1β subunit in the supernatant of macrophages treated with LPS prior to apoptotic cell treatment or apoptotic cells prior to LPS was observed (FIG. 16A-B, IL-1β; upper panel). Of note, LPS priming by itself, leads to accumulation of de novo pro-IL-1β in macrophages as can be seen in the cell lysate fraction but none in the supernatant (third lane from left in FIGS. 16A-B, IL-1β; lower panel). The reduction in IL-1β levels was seen even if NF-κB triggering with LPS was allowed before exposure to apoptotic cells. Comparable results are shown with caspase-1 where less activation of caspase-1 was measured at pre- and post-transcription levels following apoptotic cells treatment in the presence of different inducers.

Figure 17A:
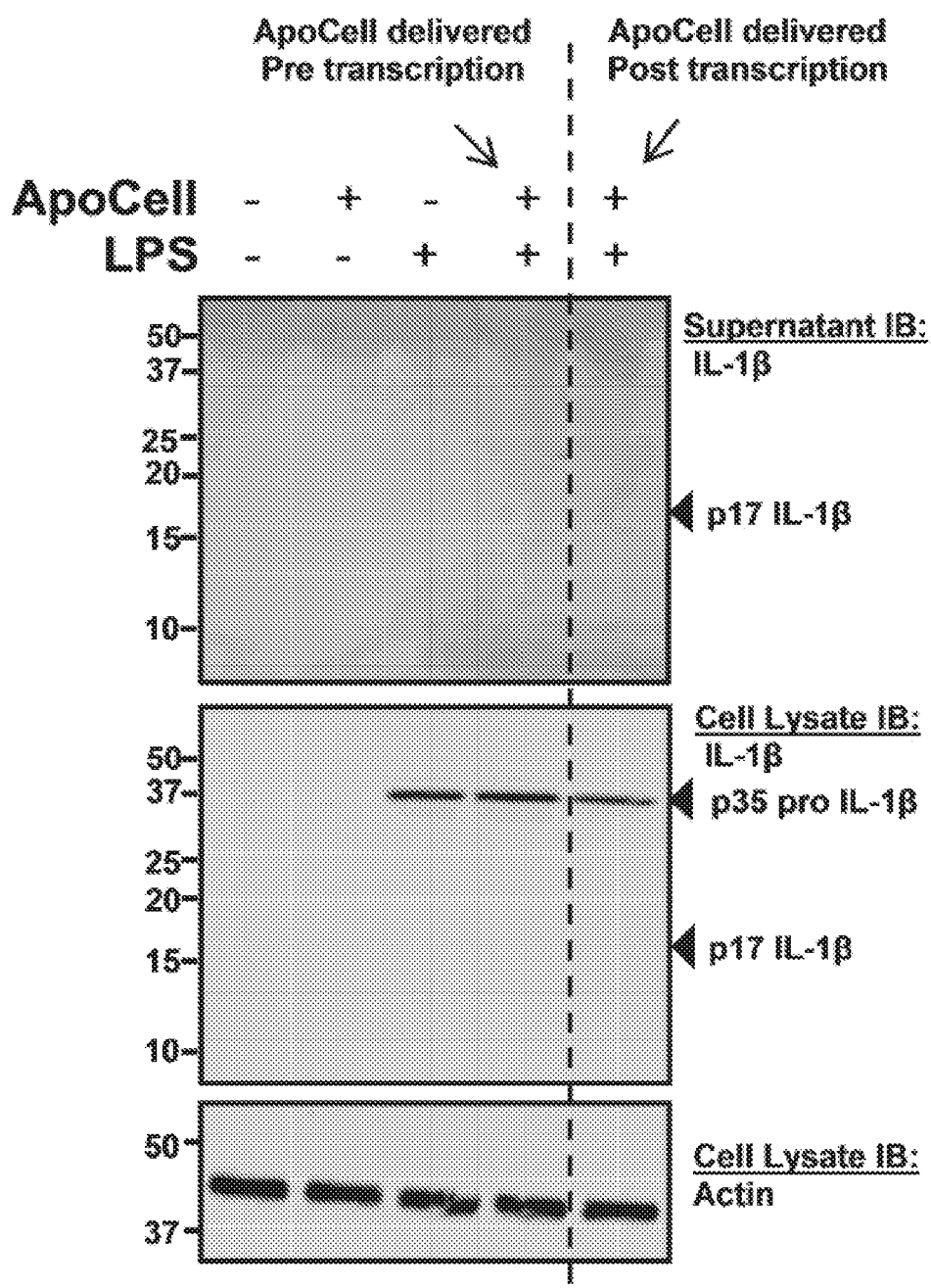
FIGS. 17A-B depict western blot analyses performed on proteins extracted from supernatant and cell lysates of pMΦ cells. The pMΦ cells were treated with either LPS, apoptotic cells or treated with apoptotic cells prior to LPS (prior to NF-κB signaling, forth lane from left) or treated with LPS prior to apoptotic cell treatment (to promote NF-κB signaling, fifth lane from left). An anti-mouse actin served as a loading control. Shown are representative data of two experiments.
Figure 17B:
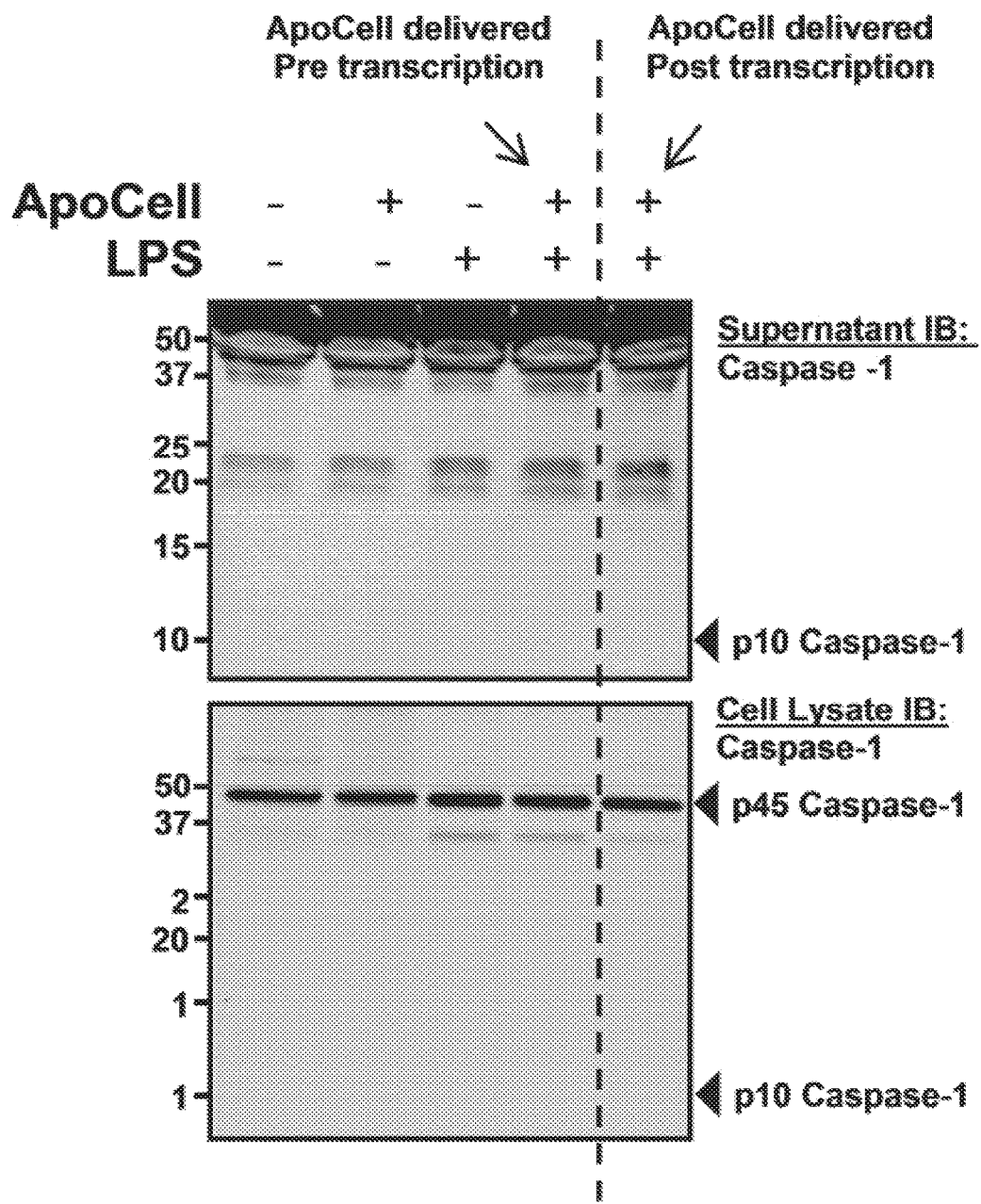
Figure 18A:
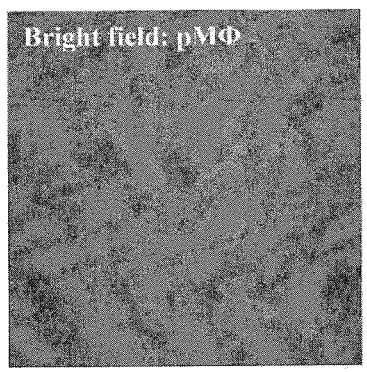
FIGS. 18A-F are micrographs depicting pMΦ cells as seen using in (18A) brightfield microscopy or (18B-F) under fluorescent microscopy stained with 1 μM of a reactive oxygen species (ROS) sensitive dye. (18B-F) Prior to staining with the ROS sensitive dye, the pMΦ cells were (18C) incubated with an ROS inhibitor (N-Acetyl-cysteine, 7.5 mM), (18D) treated with pyocyanin (0.5 mM), (18E) treated with 3% DSS or (18F) treated for 2 hours with apoptotic cells followed by a 30 min incubation with 3% DSS. Magnification in all panels is ×100. The experiments were repeated 3 times, independently; one representative experiment is shown.
Figure 18B:
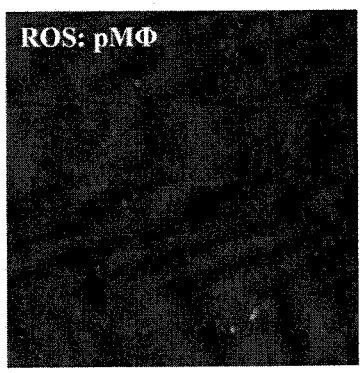
Figure 18C:
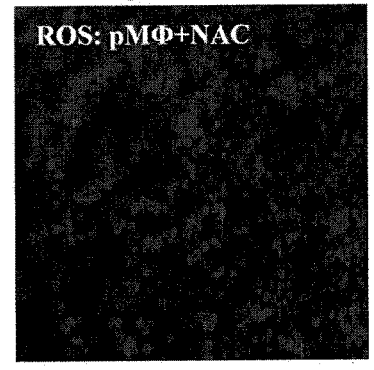
Figure 18D:
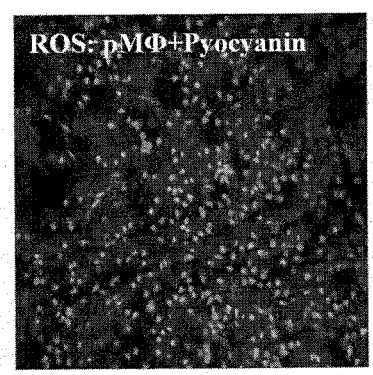
Figure 18E:
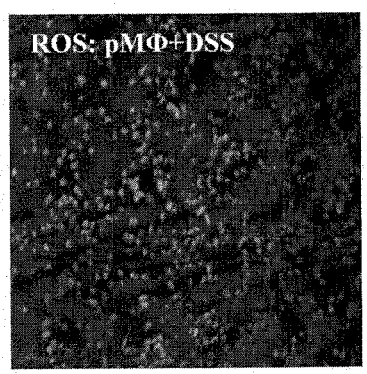
Figure 18F:
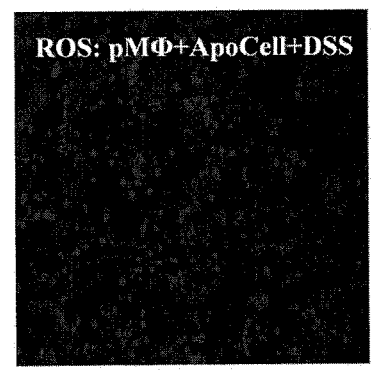

Western blot analysis was also used to verify that apoptotic cells and LPS by themselves do not affect the secretion of mature IL-1β or caspase-1 activation in the absence of inflammasome triggering. Indeed, no secretion of mature IL-1β or caspase-1 activation was observed, both at the pre- and post-transcription levels, indicating the involvement of NLRP3-inflammasome (FIG. 17A-B). Taken together, apoptotic cells appear to have a distinct inhibition effects on NF-κB and NLRP3.

Example 10

The Apoptotic Cell Anti-Inflammasome Effect is Mediated Via ROS, Lysosome Stabilization, and $K^+$ Efflux Activation of the NLRP3 inflammasome was suggested to be ROS-dependent, and indeed many NLRP3 stimulators also induce ROS generation. DSS was also found to generate ROS during NLRP3 activation and accumulation of IL-1β.

Figure 19:
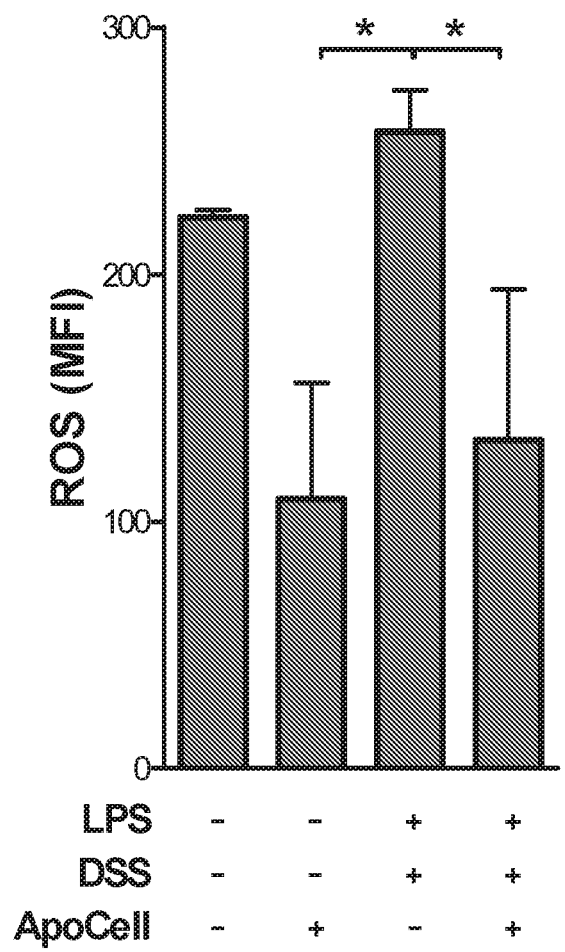
FIG. 19 is a graph demonstrating reduction in reactive oxygen species (ROS) generation in DSS-treated macrophages pretreated with apoptotic cells. Flow-cytometry analysis of pMΦ stained with ROS-sensitive dye. pMΦ were treated for 2 h with apoptotic cells and primed with LPS followed by incubation with 3% DSS for 30 min. The negative control samples were treated with media only. ROS generation was determined by flow cytometry using a fluorescence probe, excluding dead cells base on FSC/SSC parameters. Shown are means±SEM of 3 experiments done in triplicates (*p<0.05, unpaired t-test).

The effect of apoptotic cell treatment on ROS generation was examined by both fluorescent microscopy and real time flow cytometry. In agreement with the previous observations, peritoneal macrophages incubated with DSS were found to induce ROS, similarly to pyocyanin, another inducer of ROS (FIG. 18). When macrophages were pre-treated with apoptotic cells and then treated with DSS, a marked and significant reduction in ROS generation was seen (FIG. 18 and FIG. 19, $p<0.05$, one way ANOVA). The reduction is similar to the effect obtained by ROS inhibitor N-Acetyl-cysteine (NAC).

A second mechanism described as an important mechanism in NLRP3 activation is lysosomal damage, leading to cytosolic release of lysosomal content that in turn triggers the inflammasome. It was also suggested that DSS triggers inflammasomes by lysosomal damage. To test whether apoptotic cells prevent lysosomal damage, cytosolic staining was performed with acridine orange, a dye emitting green fluorescence when monomericly bonded to DNA and RNA and red fluorescence when dimerized in acidic compartments. The extent of the red fluorescence correlates with the level of intracellular acidic lysosomes.

Figures 20A, 20B:
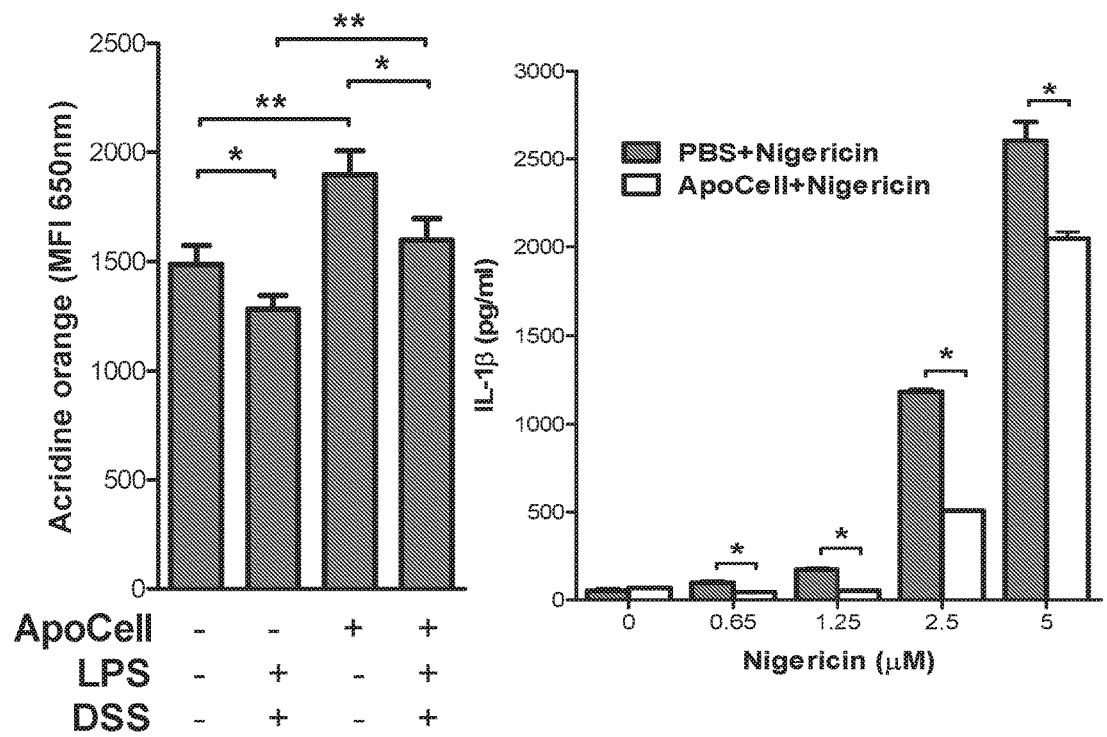
FIGS. 20 A-B is bar graphs demonstrating the effect of the apoptotic cells on lysosomal damage and K+ efflux in peritoneal macrophages (pMΦ). (20A) Flow cytometry analysis of B6 pMΦ treated for 2 h with apoptotic cells and/or 24 h with DSS were stained with fluorochrome acridine orange (AO). Loss of fluorescence, which correlates with reduced numbers of lysosomes, was analyzed by flow cytometry, excluding dead cells base on FSC/SSC parameters. Shown are means±SEM of 4 independent experiments (*p<0.05, **p<0.03 one way ANOVA). (20B) Apoptotic cell treatment inhibits nigericin-induced IL-1β secretion. B6 pMΦ cells were treated with nigericin at the indicated concentrations in the presence of LPS priming, with or without apoptotic cell treatment (*p<0.01 unpaired t-test).

DSS treatment resulted in a significant decrease in red fluorescence intensity (FIG. 20A, $p<0.05$, one way ANOVA), indicating lysosomal damage, and in agreement with previous findings for DSS and crystals. When the macrophages were treated with apoptotic cells prior to the DSS challenge, a significant increase in the number of acidic compartments was detected suggesting stabilization of the lysosomal compartment (FIG. 20A, $p<0.03$, one way ANOVA). This observation was confirmed using confocal microscopy, which showed a more diffuse cytosolic staining pattern when macrophages were treated with DSS, indicating rupture of lysosomes (data not shown). However, when treated with apoptotic cells prior to DSS challenge, the lysosomes appeared intact. Taken together, this data suggests that lysosomal compartment stabilization is involved in inflammasome regulation by apoptotic cells.

A third NLRP3 activation mechanism was suggested to involve changes in the intracellular ionic milieu, either via ATP and the $P2X_7$ receptor or by pore forming toxins, and possibly also involving pannexin-1. Blocking $K^+$ efflux or applying high concentrations of $K^+$ prevented NLRP3 inflammasome activation by many agents, including DSS.

To evaluate to role of $K^+$ efflux in the presence of apoptotic cells, the effect of macrophages pretreated with apoptotic cells on inhibiting IL-1β secretion following LPS and nigericin challenge was examined. As seen in FIG. 20B, IL-1β secretion was indeed inhibited up to 70% by apoptotic cells in a dose-dependent manner, although less competent at high concentrations.

Example 11

The ApoCell Cell Preparation Comprises Methylprednisolone

In order to determine the amount of methylprednisolone in the ApoCell final product, cell-preparations were produced according to the production method of the invention. During preparation, the cells were incubated in an incubation medium comprising 50 μg/mL of methylprednisolone for six hours. At the end of apoptosis induction the cells are washed and re-suspended in PBS. Final volume of ApoCell product after collection of quality control samples was 300 ml. The residual amount of methyl prednisolone in the supernatant of the ApoCell final product was determined on final products prepared from three runs. Methylprednisolone levels were determined using reversed-phase liquid chromatography (HPLC). Assays were qualified and performed by Spectrolab Analytical Laboratory, Rehovot, Israel. The levels of residual methyl prednisolone in the ApoCell final product are presented in Table 3 below.

The range of residual methylprednisolone concentration in the final product is 3.7 mg/L in the lowest cell dose of ApoCell product and 21.9 mg/L in the highest cell dose. The range of total methyl prednisolone in final dose is 1.11-6.57 mg in correlation to the ApoCell dose. The results demonstrate that the amount of methylprednisolone present in ApoCell, including the highest cohort, is negligible relative to the dose of methylprednisolone received by a patient as part of the general treatment protocol during Bone Marrow Transplantation.

TABLE 3

Residual Methylprednisolone in ApoCell Final Product

| Total amount of Methyl prednisolone in final dose | Residual concentration of Methyl prednisolone | Cohort No. (cells/kg) | Total number of cells in ApoCell dose | Run No. (Batch ID No.) |
|---|---|---|---|---|
| 1.11 mg | 3.7 mg/L | 1 ($3.5 \times 10^7$ cells/kg) | $2.45 \times 10^9$ | Run 1 (Batch ID: 0021) |
| 3.3 mg | 11.2 mg/L | 3 ($1.4 \times 10^8$ cells/kg) | $7 \times 10^9$ | Run 2 (Batch ID: 0024) |
| 6.57 mg | 21.9 mg/L | 4 ($2.1 \times 10^8$ cells/kg) | $11.34 \times 10^9$ | Run 3 (Batch ID: 0022) |

TABLE 4

ApoCell yield as function of plasma type

| Treatment | ApoCell yield from frozen sample (%) | Apoptosis (An$^+$ PI$^-$ %) | Necrosis (PI %) |
|---|---|---|---|
| Autologous plasma (normal TG level) | 56.2 | 50 | 1.9 |
| Heterologous plasma with normal TG level | 52 | 57 | 2.6 |
| Heterologous plasma with TG level of 23.5 millimol/liter | 39.7 | 51 | 2.8 |
| Heterologous plasma with TG level of 5.6 millimol/liter | 15.6 | 42 | 2.8 |

Example 12

Effect of Plasma Comprising a High-Triglyceride Level on ApoCell Cell-Preparation Yield In order to determine the effect of plasma containing high levels of triglycerides (TG) on the cell yield of the ApoCell composition, cells were collected from a healthy donor with normal triglyceride levels and were frozen in a freezing medium devoid of anticoagulant. Following thawing, the cells were divided into four treatment groups:

(1) Incubation in incubation medium containing autologous plasma with normal triglyceride levels.

(2) Incubation in incubation medium containing heterologous plasma with normal triglyceride levels.

(3) Incubation in incubation medium containing heterologous hyperlipidemic plasma with a TG level of 23.5 millimol/liter.

(4) Incubation in incubation medium containing heterologous hyperlipidemic plasma with a TG level of 5.6 millimol/liter.

As can be seen in the results depicted in Table 4, incubation in the presence of plasma containing a high triglyceride level resulted in lower ApoCell yield (An$^+$=cells positive for Annexin V staining, PI$^-$=cells negative for propidium iodide staining). Similarly, as can be seen in the results depicted in Table 5, preparing the cell-preparation of the invention from donors having high triglyceride levels using the same method as in Examples 1-4 herein above, resulted in low ApoCell yield.

TABLE 5

ApoCell yield as function of triglyceride level in donor's blood

| final yield of ApoCell: actual cell number $\times 10^9$ and (% of frozen cells) | Collected cell number ($\times 10^9$) | TG plasma level (mmol/l) | Collection ID# | Donor ID# |
|---|---|---|---|---|
| 0.79 (4.95%) | 16.1 | 6.6 | 406-2 | 406 |
| 2.04 (12.8%) | 15.9 | 2.6 | 406-3 | |

Example 13

Effect of Anticoagulant on ApoCell Cell-Preparation Yield in the Presence of Plasma Comprising a High-Triglyceride Level In order to determine whether addition of anticoagulant during production of ApoCell results in a high and stable cell yield, cells were collected from a healthy donor using leukapheresis and used to produce the ApoCell product as described herein. During production, the cells were frozen in freezing media and incubated in incubation media both comprising either:

1. Autologous plasma with normal triglyceride levels. No anti-coagulant in freezing or incubation media.

2. Heterologous plasma from a healthy donor with normal triglyceride levels. No anti-coagulant in freezing or incubation media.

3. Heterologous hyperlipidemic plasma with high triglyceride levels. No anti-coagulant in freezing or incubation media.

4. Heterologous hyperlipidemic plasma with high triglyceride levels (same as in clause 3) and 5% of anticoagulant solution (ACD formula A+10 U/ml heparin).

The cells from each treatment group were exposed to the same plasma that they were frozen with, throughout the experiment.

In agreement with the results presented in Example 11, the results in Table 6 demonstrate that high plasma level of triglycerides results in a low yield of the ApoCell cell-preparation, as can be seen in treatment 3 (10.4% out of frozen cells). Unexpectedly, addition of anticoagulant during the preparation process had a protective effect, thus enabling arrival at a normal cell-preparation yield, as can be seen in treatment 4 (42.6% out of frozen cells).

TABLE 6

ApoCell yield summary in different treatments

| Treatment # | Treatment description | Yield at thawing (% from frozen cells) | Yield of ApoCell preparation (% from frozen cells) |
|---|---|---|---|
| 1 | Autologous plasma | 82.1 | 49.5 |
| 2 | Heterologous plasma | 76.6 | 50.1 |
| 3 | Heterologous plasma, high TG, no anticoagulant | 11.3 | 10.4 |
| 4 | Heterologous plasma, high TG, with anticoagulant | 69.9 | 42.6 |

Example 14

The Yield of ApoCell Cell-Preparation is Affected by Addition of Anticoagulant During Various Stages of the Preparation Process In order to examine the effect of anticoagulant addition during different stages of ApoCell production on the cell-yield of the final preparation, cells were collected by leukapheresis from the same three healthy donors (denoted 0036, 0037 and 0038) at two different medical centers (denoted medical centers 1 and 2). In addition, cells were collected from two more healthy donors (denoted 0039-1 and 0040-1) at medical center 1. The cell collection at the medical centers differed in the protocol of anticoagulant addition during cell collection as follows:
1. Center 1—5000 U of Heparin (Heparin sodium, Fresenius) is injected into a bag of Acid Citrate Dextrose formula A (ACD formula A); the heparin and ACD formula A circulate in the leukapheresis machine such that a small fraction reaches the donor and the collection bags (cells and plasma).
2. Center 2—5000 U of Heparin (Heparin sodium, Fresenius) is injected directly into the cell collection bag, thus the Heparin does not circulate within the leukapheresis machine, does not reach the donor and does not reach the plasma collection bag. ACD formula A, however, circulates in the machine and reaches the donor and collection bags (cells and plasma).

Therefore, the main difference between the production method in centers 1 and 2 is the concentration of Heparin in the collection bags. The concentration of Heparin in the cell collection bag in medical center 2 is higher in comparison to the concentration of Heparin in the cell collection bag in medical center 1. Additionally, the plasma collection bag in medical center 2 is substantially devoid of heparin.

Following cell-collection at the two medical centers, ApoCell cell preparations were produced from the collected cells under 4 conditions:
1. $F^-/Inc^-$=No anti-coagulant was added during freezing, incubation or washing steps.
2. $F^-/Inc^+$=No anti-coagulant was added during freezing and washing, anticoagulant was added during incubation.
3. $F^+/Inc^+$=Anti-coagulant was added during freezing, during washing steps following freezing and during incubation.
4. $F^+/Inc^-$=Anti-coagulant was added during freezing and washing steps following freezing but was not added during incubation.

Each freezing, incubation or washing media containing an anticoagulant during this experiment, contained 5% anticoagulant. The anti-coagulant used during the experiment was ACD Formula A supplemented with 10 U/ml heparin.

As can be seen in Table 7, the average yield of ApoCell cell-preparation produced without addition of anti-coagulant during freezing or incubation was lower in medical center 2 than in medical center 1 (25.2 vs. 51.4%, respectively). Addition of anti-coagulant during incubation or during both incubation and freezing resulted in a high and stable cell yield of above 40% in both medical centers 1 and 2. Therefore, addition of anti-coagulant during incubation or during both incubation and freezing results in a high yield of the ApoCell cell-preparation, regardless of the cell collection conditions. The yield values in Table 7 refer to cells in the ApoCell composition out of frozen collected cells from which the composition derived.

TABLE 7

ApoCell yield summary as a function of anticoagulant addition at different stages in the manufacturing process in two medical centers

| Yield ApoCell at preparation (% of frozen) | | | | | | | | Experimental group |
|---|---|---|---|---|---|---|---|---|
| $F^+/Inc^-$ | | $F^+/Inc^+$ | | $F^-/Inc^+$ | | $F^-/Inc^-$ | | Medical |
| 2 | 1 | 2 | 1 | 2 | 1 | 2 | 1 | Center |
| 29.7 | 62 | 61.2 | 62.5 | 50.4 | 53.4 | 45.5 | 52.1 | Donor 0036 (collections 0036-1 &SH0036-3) |
| 23 | 63.5 | 52 | 53.5 | 42 | 36.7 | 19 | 50.5 | Donor 0037 (collections 0037-1 & SH0037-2) |
| 1.7 | 58.4 | 47.8 | 53.6 | 35.4 | 42 | 11.2 | 42.7 | Donor 0039 (collections 0038-1 &SH0038-2) |
| | 36.2 | | 34.1 | | 52 | | 57.6 | Donor 0039 (collection 0039-1) |
| | 58.8 | | 53.3 | | 49 | | 54.3 | Donor 0040 (collection 0040-1) |
| 18.1 | 55.8 | 53.7 | 52.4 | 42.6 | 46.6 | 25.2 | 51.4 | AVERAGE |

Example 15

Characterization of Polymorphonuclear Cells within ApoCell Cell Preparations

In order to evaluate the percentage of granulocytes within the ApoCell cell preparations, the percentage of polymorphonuclear cells was measured within cells collected by leukapheresis and within the ApoCell compositions which were produced from each collection (Col—the number of the cell collection examined from the same patient). As can be seen in Table 8, the percentage of granulocytes within the ApoCell composition is much lower than the percentage of polymorphonuclear cells within the leukapheresis-collected mononuclear enriched cell fraction.

TABLE 8

ApoCell polymorphonuclear cell percentage

| ApoCell (final product) Identity/Purity: $CD15^{high}$ by flow cytometry (granulocytes, %) | At leukapheresis of mononuclear enriched fraction Identity/Purity: PMNs, by Sysmex hematology analyzer (%) | Cohort and patient number |
|---|---|---|
| 0.4 | Col-1: 6.6 | Cohort 1-1 |
| 0.21 | Col-1: 5 | Cohort 1-2 |
| 0.16 | Col-1: 5.4 | Cohort 1-3 |
| 0.22 | Col-1: 4.8 | Cohort 2-1 |
| 0.58 | Col-1: 31.7 Col-2: 12.5 | Cohort 2-2 |
| 0.14 | Col-1: 8.5 | Cohort 2-3 |
| 0.11 | Col-1: 14.9 Col-2: 14.2 | Cohort 2-4 |
| 0.08 | Col-1: 10.2 Col-2: 8 Col-3: 12.3 | Cohort 3-1 |
| 0.27 | Col-1: 35 Col-2: 27.6 Col-3: 12.7 | Cohort 3-2 |
| 0.25 | Col-1: 15.9 Col-2: 15.9 Col-3: 6 | Cohort 3-3 |
| 0.2 | Col-1: 7.7 Col-2: 5.7 | Cohort 4-1 |
| 0.17 | Col-1: 16.2 Col-2: 6.2 Col-3: 10.7 | Cohort 4-2 |
| 0.08 | Col-1: 8.5 Col-2: 4.7 Col-3: 7.9 | Cohort 4-3 |
| 0.22% (0.08-0.58%) | 12.1% (4.7-35%) | Average % (range) |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A stable, high yield early-apoptotic mononuclear-enriched cell population comprising a yield of at least 30% early apoptotic mononuclear-enriched cells, wherein said early-apoptotic cell population is stable for more than 24 hours, wherein production of said cell population comprises the following steps:
    (a) freezing a mononuclear-enriched cell population in a freezing medium comprising an anticoagulant;
    (b) thawing said mononuclear-enriched cell population; and
    (c) inducing apoptosis in said thawed mononuclear-enriched cell population, said inducing comprising incubating said population in a medium comprising methylprednisolone and an anticoagulant.

2. The cell population of claim 1, wherein said mononuclear enriched cells comprise at least one cell type selected from the group consisting of lymphocytes, monocytes and natural killer cells.

3. The cell population of claim 1, wherein said mononuclear enriched cells are collected by leukapheresis.

4. The cell population of claim 1, wherein said mononuclear enriched cells are obtained from a subject in need of receiving administration of a stable early apoptotic cell population.

5. The cell population of claim 1, wherein said mononuclear enriched cells are obtained from a subject allogeneic with a subject in need of receiving administration of a stable early apoptotic cell population.

6. A pharmaceutical composition, comprising a stable early-apoptotic mononuclear-enriched cell population comprising at least 30% early apoptotic mononuclear-enriched cells wherein said early-apoptotic cell population is stable for more than 24 hours, wherein production of said cell population comprises the following steps:
    (a) freezing a mononuclear-enriched cell population in a freezing medium comprising an anticoagulant;
    (b) thawing said mononuclear-enriched cell population; and
    (c) inducing apoptosis in said thawed mononuclear-enriched cell population, said inducing comprising incubating said population in a medium comprising methylprednisolone and an anticoagulant.

7. The pharmaceutical composition of claim 6, wherein said composition further comprises an anti-coagulant.

8. A method for producing a pharmaceutical composition comprising a stable early-apoptotic mononuclear-enriched cell population comprising at least 30% early apoptotic mononuclear-enriched cells wherein said early-apoptotic cell population is stable for more than 24 hours, said method comprising a step of freezing a population of mononuclear-enriched cells in a freezing medium comprising an anticoagulant, and a step of inducing apoptosis of said mononuclear-enriched population in a medium comprising methylprednisolone and an anticoagulant, or a combination thereof.

9. The method of claim 8, wherein said mononuclear enriched cells are collected by leukapheresis.

10. The method of claim 8, wherein said mononuclear enriched cells are obtained from a subject in need of receiving administration of a stable early apoptotic cell population.

11. The method of claim 8, wherein said mononuclear enriched cells are obtained from a subject allogeneic with a subject in need of receiving administration of a stable early apoptotic cell population.

* * * * *